US012575549B2

(12) United States Patent
Zhong et al.

(10) Patent No.: US 12,575,549 B2
(45) Date of Patent: Mar. 17, 2026

(54) APPLICATION OF TPK AS A TARGET IN ALZHEIMER'S DISEASE

(71) Applicant: SHANGHAI RAISING PHARMACEUTICAL CO., LTD., Shanghai (CN)

(72) Inventors: Chunjiu Zhong, Shanghai (CN); Shaoming Sang, Shanghai (CN); Jingjing Wang, Shanghai (CN); Huan Zhang, Shanghai (CN)

(73) Assignee: SHANGHAI RAISING PHARMACEUTICAL CO., LTD., Shanghai (CN)

( * ) Notice: Subject to any disclaimer, the term of this patent is extended or adjusted under 35 U.S.C. 154(b) by 716 days.

(21) Appl. No.: 17/591,379

(22) Filed: Feb. 2, 2022

(65) Prior Publication Data

US 2022/0330531 A1 Oct. 20, 2022

Related U.S. Application Data

(63) Continuation-in-part of application No. PCT/CN2020/105353, filed on Jul. 29, 2020.

(51) Int. Cl.
| | |
|---|---|
| A61P 25/28 | (2006.01) |
| A01K 67/0276 | (2024.01) |
| A61K 35/76 | (2015.01) |
| A61K 38/45 | (2006.01) |
| C07K 14/47 | (2006.01) |
| C12N 7/00 | (2006.01) |
| C12N 9/12 | (2006.01) |
| C12N 15/86 | (2006.01) |

(52) U.S. Cl.
CPC .......... *A01K 67/0276* (2013.01); *A61P 25/28* (2018.01); *C12N 15/86* (2013.01); *A01K 2217/075* (2013.01); *A01K 2227/105* (2013.01); *A01K 2267/0312* (2013.01); *A61K 35/76* (2013.01); *A61K 38/45* (2013.01); *C07K 14/4711* (2013.01); *C12N 7/00* (2013.01); *C12N 9/1235* (2013.01); *C12N 2830/008* (2013.01); *C12N 2830/48* (2013.01); *C12Y 207/06* (2013.01); *C12Y 207/06002* (2013.01)

(58) Field of Classification Search
None
See application file for complete search history.

(56) References Cited

U.S. PATENT DOCUMENTS 6,248,559 B1 6/2001 Takashima et al.

FOREIGN PATENT DOCUMENTS

| CN | 101884646 A | 11/2010 | |
|---|---|---|---|
| CN | 108567792 A | 9/2018 | |
| RU | 2542445 C2 | 2/2015 | |
| WO | WO-2016156574 A1 * | 10/2016 | ........... C07K 14/705 |

OTHER PUBLICATIONS

Rafii, et al. A phase1 study of stereotactic gene delivery of AAV2-NGF for Alzheimer's disease. Alzheimer's & Dementia. Sep. 2014;10(5):571-81.*
Matsuzaki, et al. Generation of a neurodegenerative disease mouse model using lentiviral vectors carrying an enhanced synapsin I promoter. Journal of Neuroscience Methods. 223; 133-43. 2014.*
Hèroux, et al. Alterations of thiamine phosphorylation and of thiamine-dependent enzymes in Alzheimer's disease. Metabolic Brain Disease. 1996. 11; 81-8.*
Brevini et al., (2010) "Embryonic Stem Cells Domestic Animals No shortcuts to pig embryonic stem cells," Theriogenology vol. 74; pp. 544-550.
Cao et al., (2009) "Isolation and Culture of Primary Bovine Embryonic Stem Cell Colonies by a Novel Method," Journ. Exper. Zoo. vol. 311A. pp. 368-376.
DaSilva et al., (2006) "Vaccine Development for Alheimer's Disease," Curr. Pharma. Design vol. 12; pp. 4283-4293.
Dennis (2002) "Welfare Issued Genetically Modified Animals," ILAR Journal; vol. 43; pp. 100-109.
Gibson et al., (2013) "Abromal thiamine-dependent processes in Alzheimer's Disease. Lessons from diabetes," Mol. And Cell. Neuro.vol. 55; pp. 17-25.
Houdebine et al., (2009) "Methods to Generate Transgenic Animals," pp. 31-48.
Office Action corresponding to Chinese Application No. 202080055745.1 dated Feb. 21, 2023.
Pan et al. (2017) "Enhanced Activities of Blood Thiamine Diphosphatase and Monophospha Alzheimer's Disease," PLOS One; DOI: 10.1371/journal.pone.0167273; 13 Pages.
Paris et al., (2010) "Equine embryos and embryonic stem cells: Defining reliable markers of pluripotency." Theriogenology vol. 74; pp. 516-524.
Zhou et al., (2009) "Developing tTA Transgenic Rats for Inducible and Reversible Gene Expression," Inter. Journ. Bio. Scienc. vol. 5; pp. 171-181.
Baburamani et al., (2017) "Effect of Trp53 gene deficiency on brain injury after neonatal hypoxia-ischemia," Oncotarget, vol. 8, pp. 12081-12092.
Chen et al. (2013) "Decoding Alzheimer's disease from perturbed cerebral glucose metabolism: Implications for diagnostic and therapeutic strategies," Progress in Neurobiology, vol. 108, pp. 21-43.
Church et al. (2009) "Lineage-Specific Biology Revealed by a Finished Genome Assembly of the Mouse," PLOS Biology, vol. 7, No. 5, 16 pages.
Devan et al. (2019) "Challenges of gene delivery to the central nervous system and the growing use of biomaterial vectors," Brain Research Bulletin, 150, pp. 216-230.

(Continued)

*Primary Examiner* — Allison M Fox
*Assistant Examiner* — Gina Pronzati

(57) ABSTRACT

Provided is use of thiamine pyrophosphokinase TPK as a target in the treatment of Alzheimer's disease; and AD symptoms due to the inhibited TPK can be prevented by promoting the kinase activity and/or expression level of TPK protein in brain with TPK as a target.

5 Claims, 56 Drawing Sheets

Specification includes a Sequence Listing.

(56) References Cited

OTHER PUBLICATIONS

Drummond et al., (2016) "Alzheimer's disease: experimental models and reality," Acta Neuropathol, pp. 1-21.

Extended European Search Report corresponding to European Application No. 20850268.2-1112 dated May 3, 2023.

Hall et al. (2009) "Overview: Generation of Gene Knockout Mice," Author manuscript, 23 pages, published in final edited form as: Curr Protoc Cell Biol, vol. 44, No. 1, pp. 1934-2500.

Karuppagounder et al. (2009) "Thiamine deficiency induces oxidative stress and exacerbates the plaque pathology in Alzheimer's mouse model," Neurobiology of Aging, vol. 30, No. 10, pp. 1587-1600.

Office Action corresponding to Japanese Application No. 2022-506763 dated Mar. 3, 2023.

Office Action corresponding to Russian Application No. 2022105436 dated Apr. 4, 2023.

Office Action corresponding to Russian Application No. 2022105436 dated Nov. 11, 2022.

Oganov et al. (2010) "The importance of evidence-based medicine for clinical practice," Fundamentals of evidence-based medicine, Silicea-Polygraph, 390 pages, p. 11, paragraphs 2-3.

Search Report corresponding to Russian Application No. 2022105436 completed Nov. 11, 2022.

Pavlova et al. (2016) "Dependence of Vitamin B1 Metabolism and the State of Astroglia in the Rat Brain on the Supply with this Vitamin," Neurophysiology, vol. 48, No. 5, pp. 336-345, 10 pages.

Puhl et al., (2019) "Challenges of gene delivery to the central nervous system and the growing use of biomaterial vectors," Brain Research Bullletin vol. 150, pp. 216-230.

Sang et al. (2015) "Reduced Thiamine Diphosphate Level Contributes to Brain Glucose Hypometabolism and Neurodegeneration in Alzheimer's Disease," Alzheimer's & Dementia, vol. 11, No. 7, 1 page.

Tsien et al. (1996) "Subregion- and Cell Type-Restricted Gene Knockout in Mouse Brain," Cell, vol. 87, No. 7, pp. 1317-1326.

Yu et al., (2018) "Thiamine deficiency contributes to synapse and neural circuit defects," Biological Research vol. 51:35 pp. 1-9.

Crosson et al., "Helper-free Production of Laboratory Grade AAV and Purification by Iodixanol Density Gradient Centrifugation." Mol. Ther. Methods Clin. Dev., vol. 10, pp. 1-7 (2018).

International Preliminary Report on Patentability Corresponding to International Application No. PCT/CN 2020/105353 dated Feb. 8, 2022.

Sang et al., "Thiamine Diphosphate Reduction Strongly Correlates with Brain Glucose Hypometabolism in Alzheimer's Disease, Whereas Amyloid Deposition Does Not." Alzheimer's Research & Therapy, No. 10 (2018).

Sang et al., "Thiamine Pyrophosphokinase Deficiency Induces Alzheimer's Pathology." BioRxiv, No. 10 (2020).

Translation of the International Search Report Corresponding to International Application No. PCT/CN 2020/105353 dated Nov. 4, 2020.

Translation of the Written Opinion of the International Searching Authority Corresponding to International Application No. PCT/CN 2020/105353 dated Nov. 4, 2020.

Wang et al., "High Thiamine Diphosphate Level as a Protective Factor for Alzheimer's Disease." Neurological Research, vol. 40(8), pp. 658-665 (2018).

Office Action corresponding to Canadian Patent Application No. 3,149,107dated Aug. 5, 2024.

Office Action corresponding to Korean Application No. 10-2022-7006712 dated Dec. 23, 2024 (with translation).

Liu et al., "Thiamine Metabolism is Critical for Regulating Correlated Growth of Dendrite Arbors and Neuronal Somata", Scientific Reports, vol. 07, Issue. 1, 5342, Jul. 13, 2017.

Huang et al. (2019) "Reduced thiamine binding is a novel mechanism for TPK deficiency disorder," Molecular Genetics and Genomics, vol. 294, pp. 409-416.

Office Action corresponding to European Application No. 20850268.2 dated Oct. 15, 2025.

* cited by examiner

TPK $^{fl/fl}$ MICE          CaMKII-CreERT2
                                    MICE

WT: TPK $^{fl/fl}$ MICE
CaMKII-KO: TPK $^{fl/fl}$; CaMKII-CreERT2

WILDTYPE ALLELE 1  2      3                            4                    5      9

CONDITIONAL KO ALLELE
(AFTER FLP RECOMBINATION)

LoxP_F   Neo_delete_F

LoxP_R   Neo_delete_R

▷LoxP SITE      ▯EXON      ▭ CKO REGION   ▭ HOMOLOGY ARM   ▯ FRT SITE

CORTEX

WT                    CamKII-KO

TPK

ACTIN

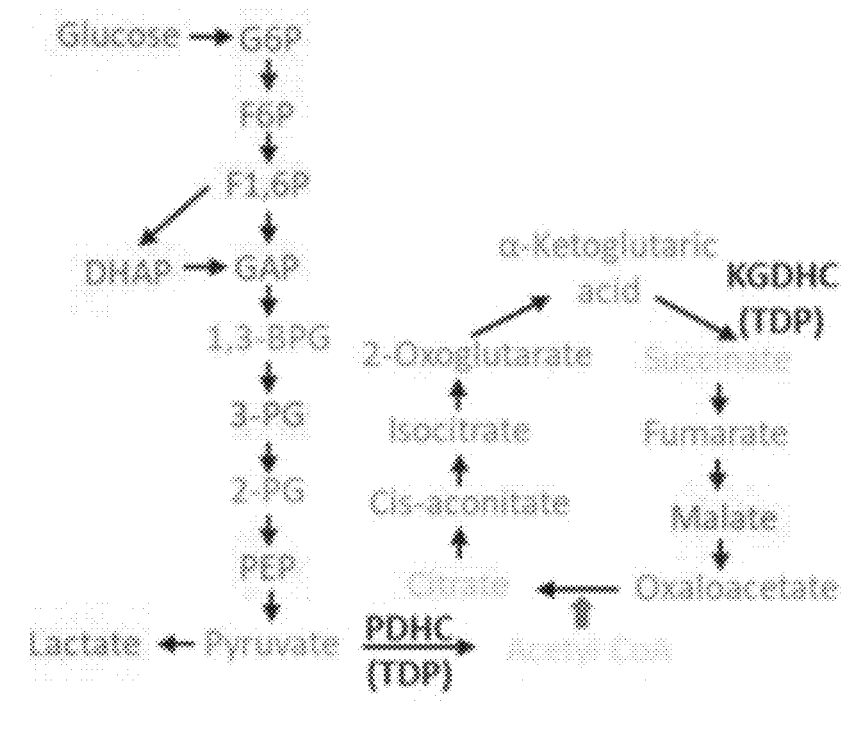
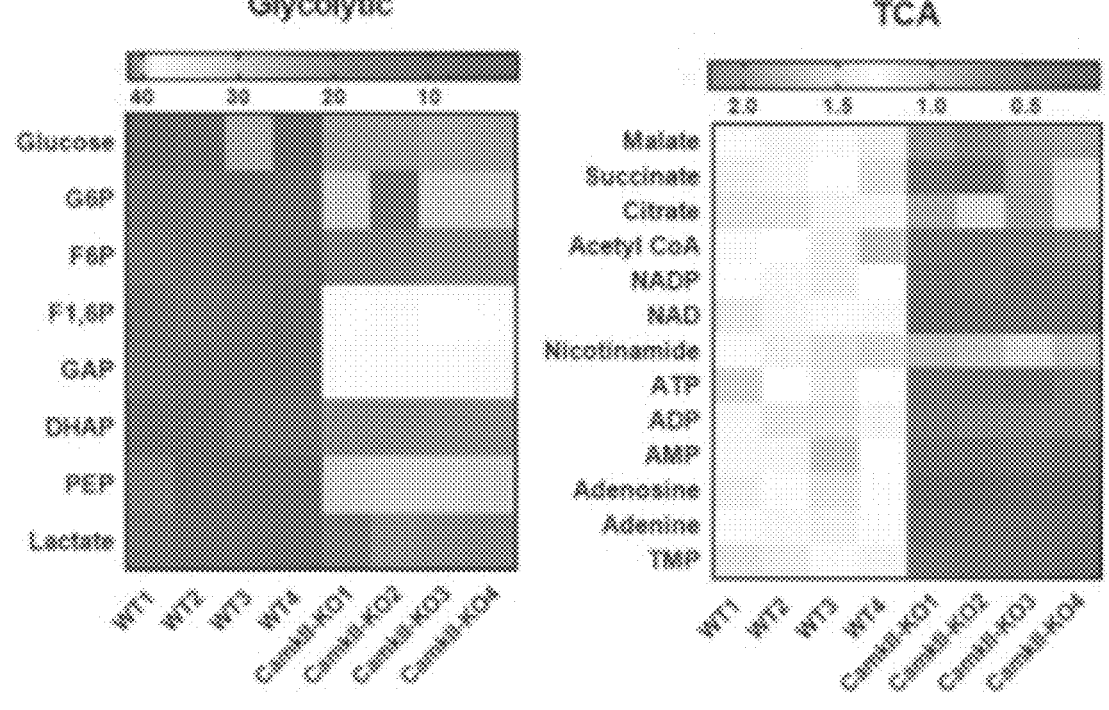
FIG. 8

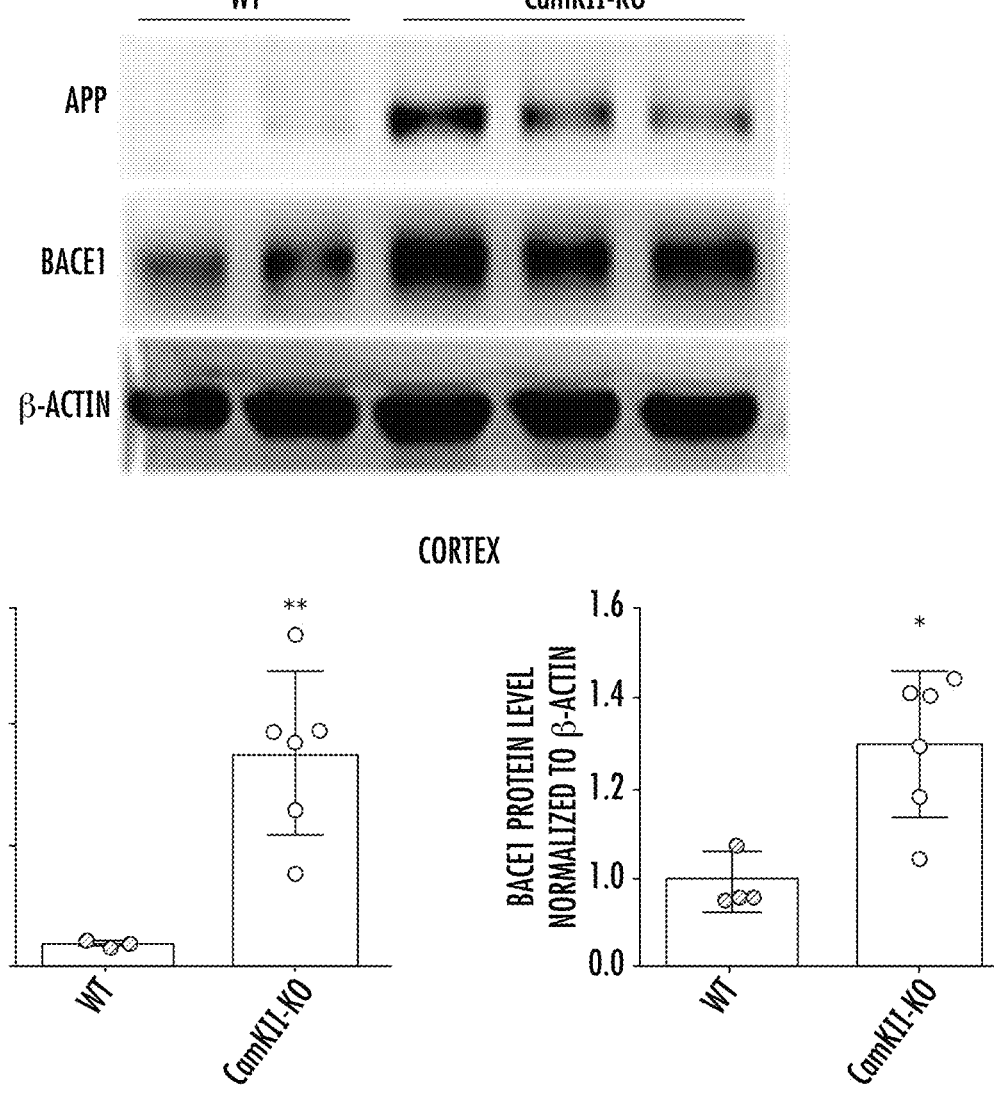
CORTEX
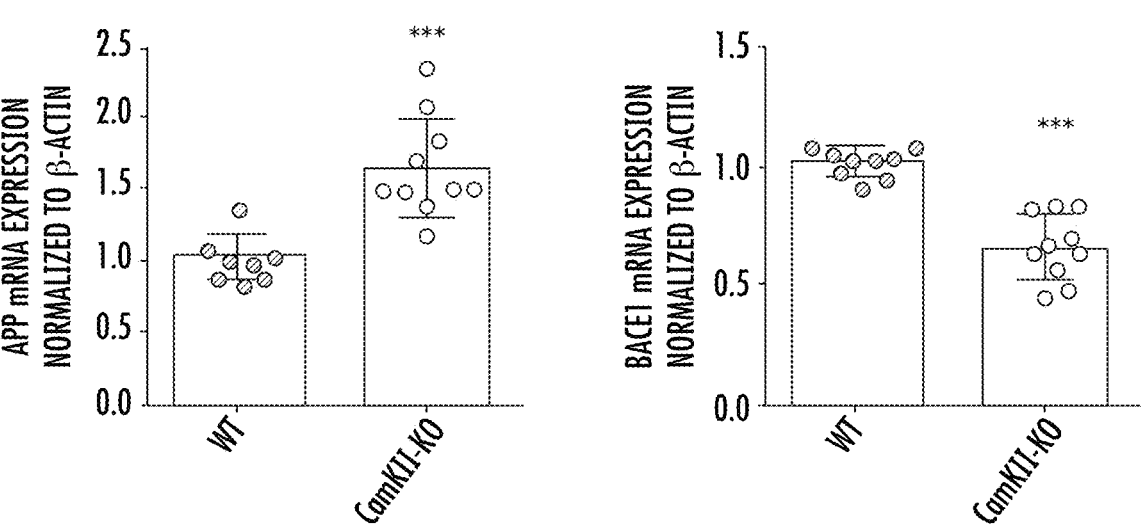
FIG. 10D

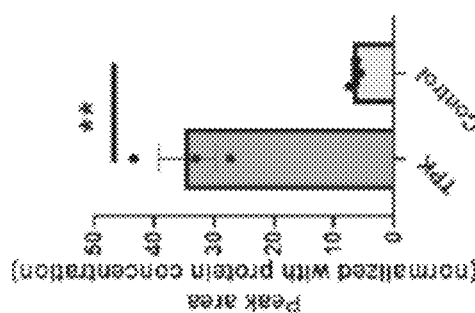
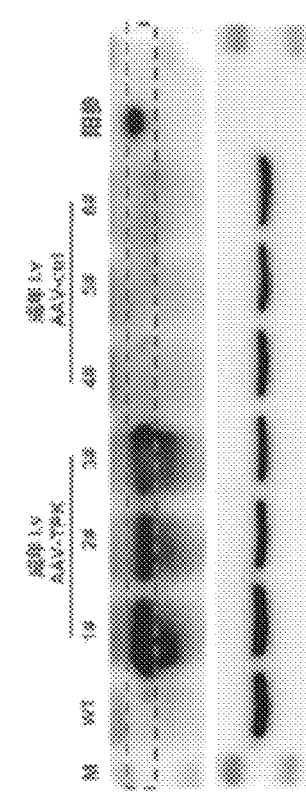
FIG. 20

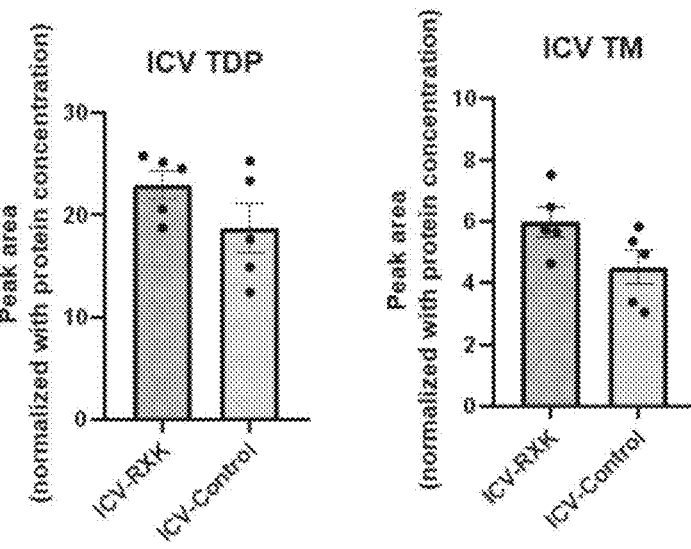
FIG. 26
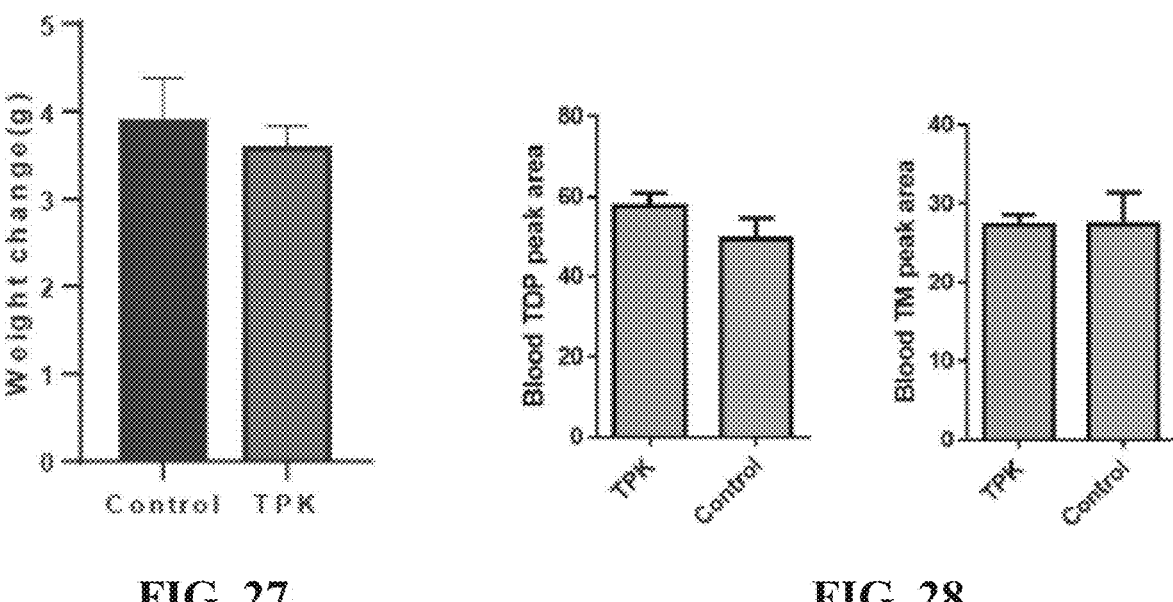
FIG. 27                    FIG. 28

AAV-TPK

AAV- CTRL

TDP/TM content in brain tissue
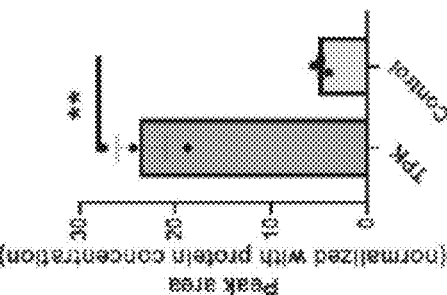
TPK expression in brain tissue
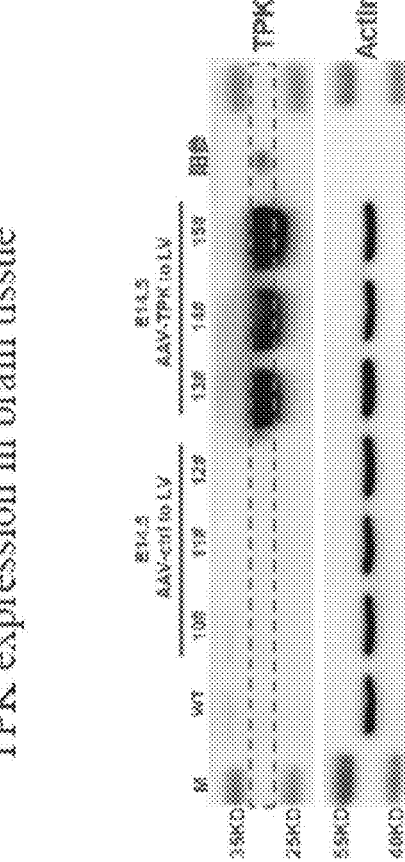
FIG. 30

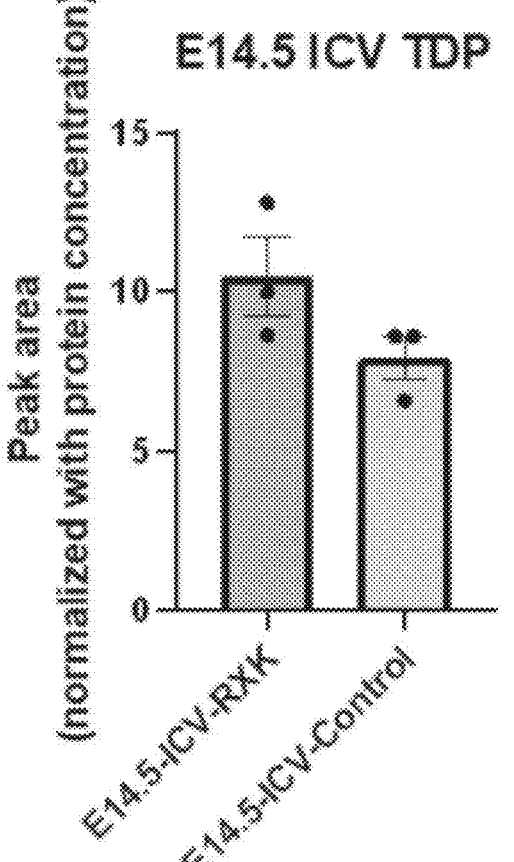
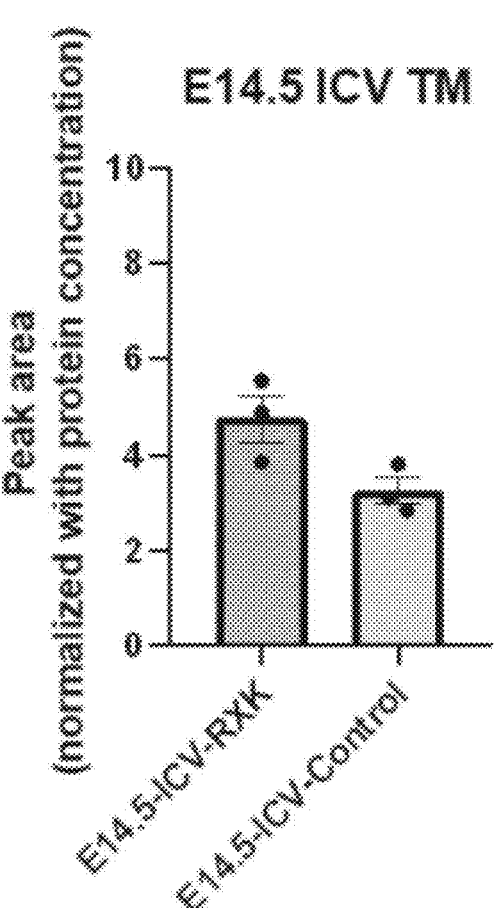
FIG. 31

APPLICATION OF TPK AS A TARGET IN ALZHEIMER'S DISEASE

CROSS REFERENCE TO RELATED APPLICATIONS

The application claims the benefit of PCT International Patent Application Serial No. PCT/CN2020/105353, filed Jul. 29, 2020, which itself claims the benefit of Chinese Patent Application No. 201910711540.3 filed before the China Patent Office on Aug. 2, 2019 and entitled "A method for constructing an animal model and the use of the corresponding model" and Chinese Patent Application No. 202010038537.2 filed before the China Patent Office on Jan. 14, 2020 and entitled "Use of TPK as a target in Alzheimer's disease", the entire contents of each of which is incorporated herein by reference.

REFERENCE TO SEQUENCE LISTING SUBMITTED ELECTRONICALLY

The content of the electronically submitted sequence listing in ASCII text file (Name: 1547_40_PCT_US_CIP_ST25_ST25.txt; Size: 28 kilobytes; and Date of Creation: Feb. 2, 2022) filed with the application is incorporated herein by reference in its entirety.

TECHNICAL FIELD

The invention relates to the field of medicine, in particular to the use of TPK as a target in Alzheimer's disease.

BACKGROUND

Alzheimer's disease (AD) is the most common type of dementia, mainly characterized by chronic and progressive regression in cognition and memory, and change in personality. By 2015, there were more than 50 million AD patients worldwide, and the incidence increased with the age of people more than 65 years old. Along with the continuous development of global ageing progress, AD has brought a heavy economic and mental burden to the society and families.

AD is a disease with various pathophysiological changes, including the loss of neuron, the activation of glial cells, characteristic senile plagues formed by the extracellular deposit of amyloid beta-protein (Aβ), and neurofibrillary tangles caused by the hyperphosphorylation of intracellular Tau protein, etc. In addition, the loss of synapse, cerebral glucose metabolism disorders, oxidative stress and the like are also constant pathologic changes in AD brains, and the reduction of cerebral glucose metabolism in patients is closely related to the cognition disorder.

Since the pathogenesis is unclear, there still lacks an effective method for the treatment of AD. The classic "Aβ cascade hypothesis" is always the most mainstream theory for explaining the AD pathogenesis. On this basis, various transgenic animal models have been developed, and the experiments for developing medicaments have been performed, all of which, however, were currently terminated at Phase II/III clinical trials or failed. Other novel medicaments such as that inhibiting abnormal accumulation of Tau protein, have not achieved desired results, either. There are multiple factors limiting the progress of the research about AD mechanism and medicament, first of which is the selection of the target for the medicament. AD is a disease with various pathophysiological changes, a medicament against a single target cannot completely stop the progression of disease, and it's necessary to develop new therapeutic targets. Furthermore, the existing animal models for AD research are mainly established based on genetic background, and to be more exact, they are models of Aβ cascade hypothesis, rather than animal models for AD, and cannot completely simulate the multiple pathophysiological changes in AD brain; and the medicaments which are verified to be effective in existing animal models could not achieve expected results in clinic trials. It is now an urgent problem to find suitable animal models for AD.

SUMMARY

In view of this, a particular embodiment of the invention provides the use of TPK as a novel target in treating or preventing Alzheimer's disease, the particular technical solutions thereof are as follows:

Use of TPK gene or protein as a target in treating or preventing Alzheimer's disease.

Optionally, with TPK gene or protein as a target, the kinase activity and/or expression level of TPK protein in brain are promoted.

Use of TPK gene or protein as a target in a medicament for preventing or treating Alzheimer's disease, or in the screening or preparing the medicament.

Optionally, the medicament, with TPK gene or protein as a target, promotes the kinase activity and/or expression level of TPK protein in brain.

Use of a reagent promoting the kinase activity and/or expression level of TPK protein in brain in the preparation of a medicament for preventing or treating Alzheimer's disease.

Optionally, the reagent promoting the kinase activity and/or expression level of TPK protein in brain is a reagent regulating TPK protein and/or a reagent regulating TPK gene.

A medicament for preventing or treating Alzheimer's disease, the medicament, with TPK gene or protein as a target, promotes the kinase activity and/or expression level of TPK protein in brain.

Use of TPK gene or protein as a target in constructing an animal model of Alzheimer's disease.

A method for the construction of an animal model, the animal model is constructed by TPK gene knockout in a target animal.

Optionally, the target animal is a rodent.

Optionally, the rodent is a mouse.

Optionally, the exon 4 in TPK gene is knocked out.

Optionally, the method comprises the following steps: constructing a targeting vector TPK-loxp for gene knockout, introducing the targeting vector into a target animal to obtain TPK-loxP+/+ target animal.

Optionally, the sequence of the targeting vector is set forth in SEQ ID NO: 1.

Optionally, the method further comprises the steps of: crossing the TPK-loxP+/+ target animal with CamK2α-Cre/ERT2+/− target animal, obtaining CamK2α-Cre/ERT2+/−; TPK-loxP+/+ target animal with the conditional knockout of TPK gene.

Use of the animal model obtained by the above method for the construction of an animal model in a research of a neurodegenerative disease with non-disease-treatment purpose.

Optionally, the neurodegenerative disease is Alzheimer's disease.

A method for the construction of a targeting vector for an animal model, a Bacterial Artificial Chromosome is used as a vector, direct loxP sequences are inserted at both ends of a sequence homologous to an exon of TPK gene together with a neomycin resistance gene sequence.

Optionally, the exon is exon 4.

Optionally, the sequence of the targeting vector is set forth in SEQ ID NO: 1.

A targeting vector constructed by the above method for the construction of a targeting vector for an animal model.

In one aspect, the present invention provides an isolated polynucleotide comprising an expression cassette comprising a polynucleotide encoding thiamine pyrophosphokinase (TPK) operably linked to a promoter.

In some embodiments, the TPK is a mouse TPK or human TPK. In some embodiments, the promoter is a eukaryotic promoter. In some embodiments, the promoter is a neuron-specific promoter.

In another aspect, the present invention provides a vector comprising the polynucleotide of the present invention.

In another aspect, the present invention provides a host cell comprising the polynucleotide of the present invention.

In another aspect, the present invention provides a recombinant adeno-associated virus (rAAV) or recombinant Lentivirus comprising the polynucleotide of the present invention.

In another aspect, the present invention provides a pharmaceutical composition comprising the polynucleotide or the rAAV or recombinant Lentivirus of the present invention.

In another aspect, the present invention provides a method of promoting glucose metabolism, or preventing or treating a glucose metabolism disorder, preferably glucose metabolism disorder in the brain, or comprising increasing the TPK activity, preferably in brain.

In another aspect, the present invention provides a method of treating or preventing Alzheimer's disease, comprising increasing the TPK activity in brain.

In another aspect, the present invention provides a method of promoting glucose metabolism, or preventing or treating a glucose metabolism disorder, preferably glucose metabolism disorder in the brain, comprising administering the polynucleotide, vector, rAAV, recombinant Lentivirus, or the pharmaceutical composition of the present invention to a subject or patient in need thereof.

In another aspect, the present invention provides a method of treating or preventing Alzheimer's disease, comprising administering the polynucleotide, vector, rAAV, recombinant Lentivirus, or the pharmaceutical composition of the present invention to a subject or patient in need thereof.

The invention provides a novel therapeutic target for AD, a particular embodiment of the invention can, by promoting kinase activity and/or expression level of TPK protein in brain, treat or prevent AD symptoms caused by the inhibition to TPK protein level, such as thiamine metabolism disorder, glucose metabolism disorder, causing cognition regression, loss of neuron, activation of glial cell, synapse dysfunction, increased deposition of Aβ, increased abnormal phosphorylation of Tau protein, etc. With respect to the limitation of the existing animal models for AD research and the drawbacks of present thiamine-deficient animal models, the method for the construction of an animal model of the particular embodiment of the invention constructs a novel cerebral thiamine-deficient animal model by TPK gene knockout, in which the reduction of cerebral glucose metabolism can be induced, causing cognition regression, loss of neuron, activation of glial cell, synapse dysfunction, increased deposition of Aβ, increased abnormal phosphorylation of Tau protein, etc. The animal model can simulate AD-like chronic, multiple pathophysiological changes, and can be used to study the role of TDP deficiency and glucose metabolism disorder in AD occurrence and development as well as the correlation between different AD pathophysiological changes, has very important scientific significance and application value for broading the AD research, investigating AD pathogenesis, seeking novel molecular markers for the diagnosis of the disease and therapeutic targets for medicaments, etc.

BRIEF DESCRIPTION OF THE FIGURES

In order to illustrate the Examples of the invention or technical solutions of the prior art more clearly, the drawings to be used in the Examples are briefly presented as follows.

FIG. 1A is a graph of TDP levels in whole blood, FIG. 1B is a graph of TDP levels in kidney, FIG. 1C is a graph of TDP levels in liver, FIG. 1D is a graph of TDP levels in brain, FIG. 1E is a graph of TMP levels in whole blood, FIG. 1F is a graph of TMP levels in kidney, FIG. 1G is a graph of TMP levels in liver, FIG. 1H is a graph of TMP levels in brain, FIG. 1I is a graph of TM levels in whole blood, FIG. 1J is a graph of TM levels in kidney, FIG. 1K is a graph of TM levels in liver, and FIG. 1L is a graph of TM levels in brain.

FIG. 2A is a graph of TDP levels in whole blood, FIG. 2B is a graph of TDP levels in kidney, FIG. 2C is a graph of TDP levels in liver, FIG. 2D is a graph of TDP levels in brain, FIG. 2E is a graph of TMP levels in whole blood, FIG. 2F is a graph of TMP levels in kidney, FIG. 2G is a graph of TMP levels in liver, FIG. 2H is a graph of TMP levels in brain, FIG. 2I is a graph of TM levels in whole blood, FIG. 2J is a graph of TM levels in kidney, FIG. 2K is a graph of TM levels in liver, and FIG. 2L is a graph of TM levels in brain.

FIGS. 6A-6I show the influence of TPK gene knockout on TPK and TDP expression, in which FIG. 6A shows comparative mouse model in the experiments, in which WT mice are TPK$^{fl/fl}$ mice, i.e., TPK-loxP+/+ mice, CamkII-KO mice are CamK2α-Cre/ERT2+/−; Tpk-loxP+/+ mice are TPK knockout mice; FIG. 6B shows gene knockout structure of TPK-flox mice; FIGS. 6C and 6D show the comparison of expression levels of TPK enzyme in CamkII-KO mice and WT mice; FIGS. 6E and 6F are the comparisons of TDP, TMP, and TM levels in CamkII-KO mice and WT mice; and FIGS. 6G-6I show CamK2α-Cre/ERT2+/− obtained by crossing CamK2α-Cre/ERT2+/− mice with luciferase reporter mice Ai9; Cre is mainly expressed in cortex and hippocampus in Ai9 mouse, but not in cerebellum and brain stem.

FIGS. 7A-7L show the results of FDG-PET tests, impaired glucose tolerance as well as changes in body weight and fasting blood glucose performed 1, 2, 2.5 months after Tomaxifen induced TPK gene knockout in Example 2, respectively, in which FIGS. 7A-7F are FDG-PET evaluations of changes in glucose metabolism in brain areas 1 (FIGS. 7A and 7D), 2 (FIGS. 7B and 7E), and 2.5 (FIGS. 7C and 7F) months after Tomaxifen induced TPK gene knockout and FIGS. 7G-7J are graphs of impaired glucose tolerances 1 (FIG. 7G), 2 (FIG. 7H), 2.5 (FIG. 7I+−) months after Tomaxifen induced TPK gene knockout, with FIG. 7J being a bar graph of the area under the curve for each of the graphs shown in FIGS. 7G-7I; FIGS. 7K and 7L are bar graphs showing changes in body weight (FIG. 7K) and fasting blood glucose (FIG. 7L) 1, 2, and 2.5 months after Tomaxifen induced TPK gene knockout.

FIG. 8 shows the results of glycolysis and tricarboxylic acid cycle disorder after TPK gene knockout in Example 2.

FIGS. 9A-9F show the results pathological test before and after TPK gene knockout in Example 2, in which FIGS. 9A-9C show the changes in cortical surface area and weight of TPK gene-knockout mice; FIG. 9D shows the change in neuron in TPK gene-knockout mice; FIG. 9E shows the result of the change in Tunel-positive cell in TPK-knockout mice; and FIG. 9F shows the Y-maze evaluation of cognition impairment results in TPK-knockout mice.

FIGS. 10A-10F show the results of the pathologic changes in Aβ and tau caused before and after TPK gene knockout in Example 2, in which FIGS. 10A-10C show the ELISA detections of total (FIG. 10A), soluble (FIG. 10B), and insoluble (FIG. 10C) Aβ40 and Aβ42 levels as well as Aβ40/Aβ42 ratio before and after TPK gene knockout; FIGS. 10E and 10F show of the changes in protein expression level and mRNA level of APP and Bacel in hippocampus (FIG. 10E) and cortex (FIG. 10F) before and after TPK gene knockout by WB and RT-PCR detections; and FIG. 10F shows the changes in phosphorylated Tau level in cortex and hippocampus before and after TPK gene knockout by immunofluorescent staining detection.

FIGS. 11A-11J show the result of neuroinflammation response and dysfunction of blood vessel caused before and after TPK gene knockout in Example 2, in which FIGS. 11A-11D show the activation and proliferation of microglial cell (FIGS. 11A and 11B) and astrocyte (FIGS. 11C and 11D) in mouse cortex (FIGS. 11A and 11C) and hippocampus (FIGS. 11B and 11B) before and after TPK gene knockout by IHC detection; FIGS. 11E and 11F show the Ibal and GFAP mRNA levels in mouse hippocampus and cortex before and after TPK gene knockout by RT-PCR detections; and FIGS. 11G-11J show blood vessel morphology and blood vessel IgG leakage in mouse cortex and hippocampus before and after TPK gene knockout by immunofluorescent staining detections.

FIG. 19A shows the results with the AAV-TPK vector and FIG. 19B shows the results with a negative control AAV vector AAV-ctrl.

FIG. 20 shows the TPK expression (left panel) and TDP and TM contents (right panel) in the brains of mice with tail vein injection of rAAV.

FIG. 24A shows the results with the AAV-TPK vector and FIG. 24B shows the results with a negative control AAV vector AAV-ctrl.

FIG. 26 shows the TDP (left panel) and TM (right panel) contents in the liver of mice with intracerebral ventricular injection of rAAV.

FIG. 27 shows the changed body weights of the mice developed from embryos with intracerebral ventricular injection of rAAV in two weeks after ablactation.

FIG. 28 shows TDP (left panel) and TM (right panel) contents in the blood of 21-day postnatal mice developed from embryos with intracerebral ventricular injection of rAAV.

FIG. 29A shows the results with the AAV-TPK vector and FIG. 29B shows the results with a negative control AAV vector AAV-ctrl.

FIG. 30 shows the TPK expression (left panel) and TDP and TM contents (right panel) in the brains of 21-day postnatal mice developed from embryos with intracerebral ventricular injection of rAAV.

FIG. 31 shows the TDP (left panel) and TM (right panel) contents in the liver of 21-day postnatal mice developed from embryos with intracerebral ventricular injection of rAAV.

FIG. 34A shows the results with the AAV-TPK vector and FIG. 34B shows the results with a negative control AAV vector AAV-ctrl.

FIG. 38A shows the results with the AAV-TPK vector and FIG. 38B shows the results with a negative control AAV vector AAV-ctrl.

DETAILED DESCRIPTION OF THE INVENTION

I. Particular Embodiments

Figures 1A, 1B:
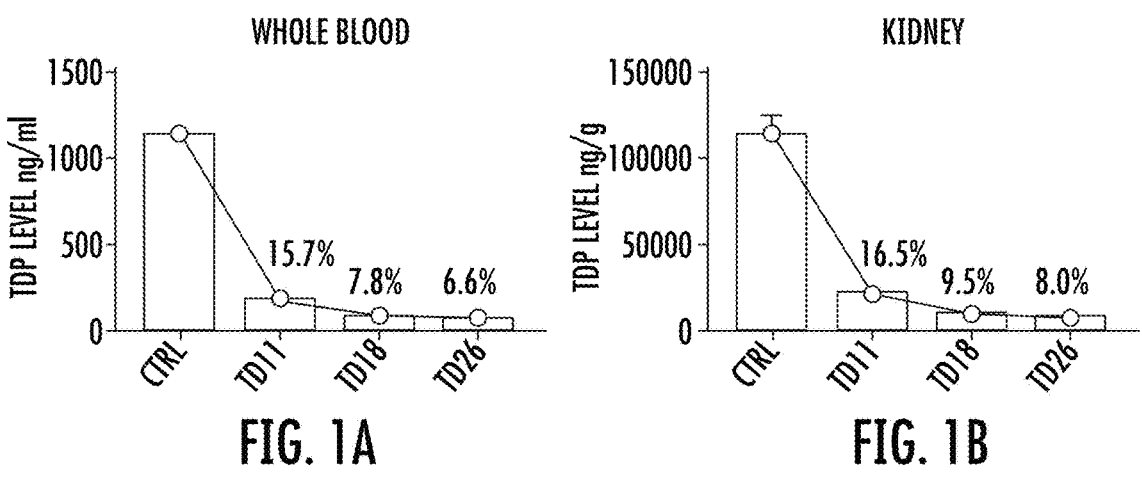
FIGS. 1A-1L show the comparison of TDP, TMP, and TM levels in brain, blood, liver, and kidney in mice of TD model in Example 1. More particularly.
Figures 1C, 1D:
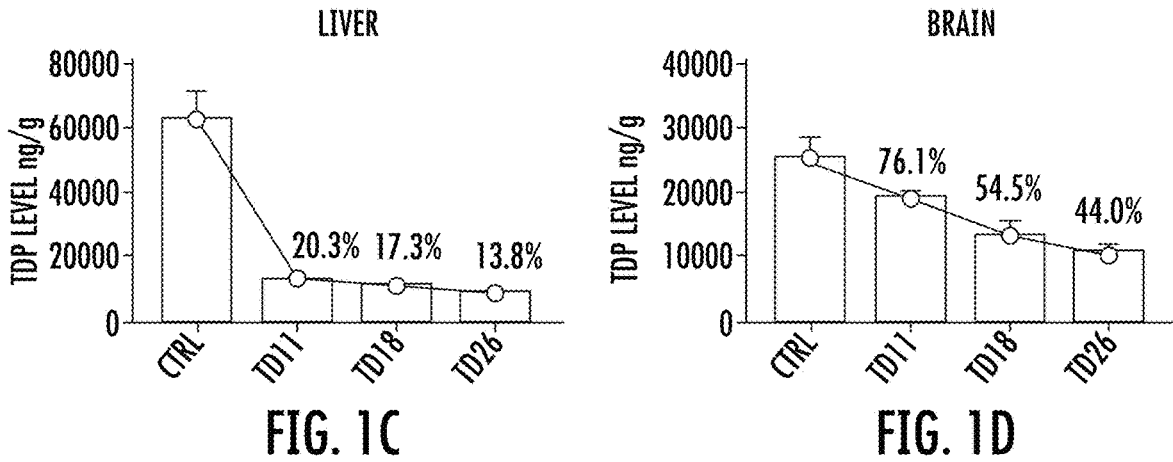
Figures 1E, 1F:
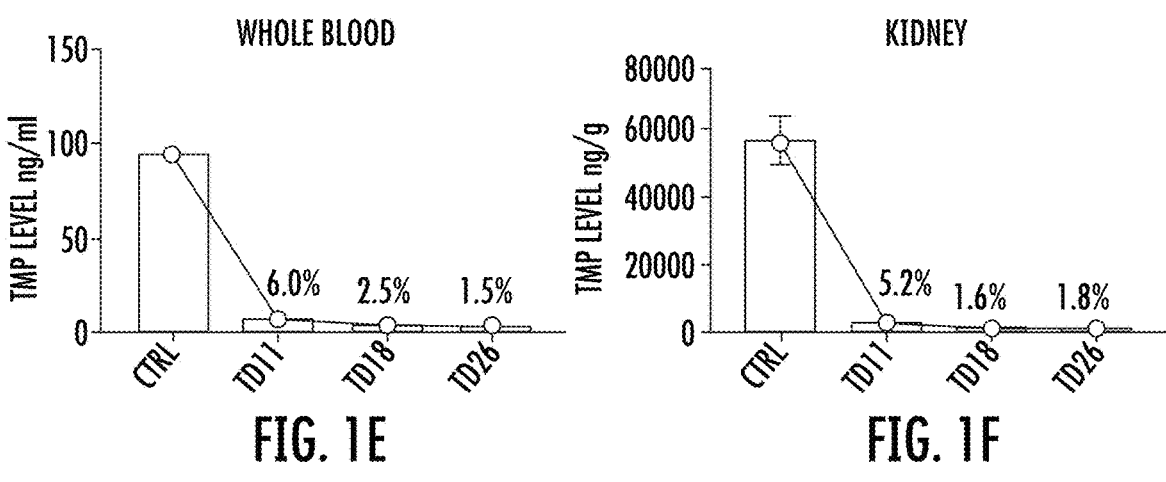
Figures 1G, 1H, 1I, 1J, 1K, 1L:
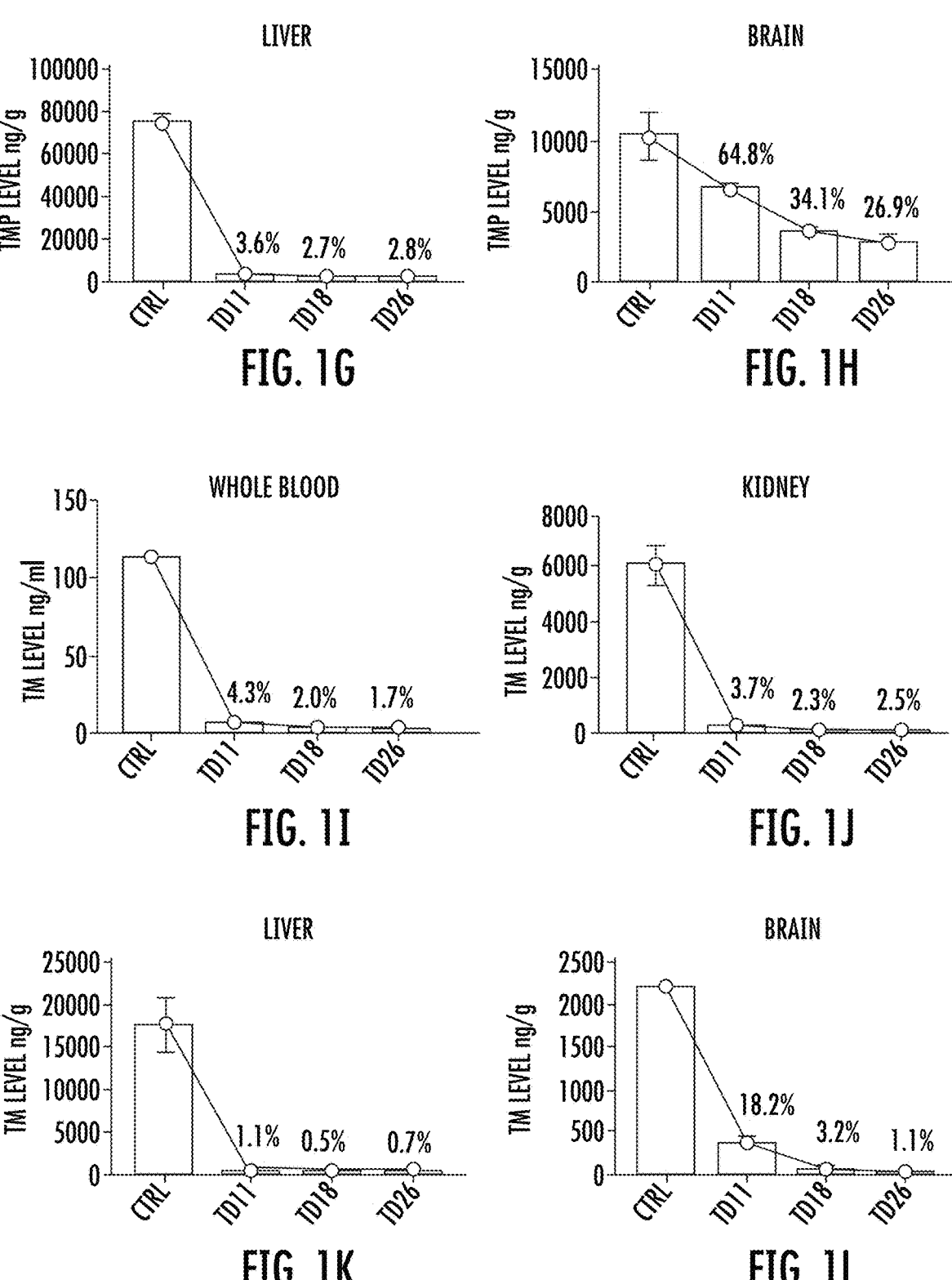
Figure 2A:
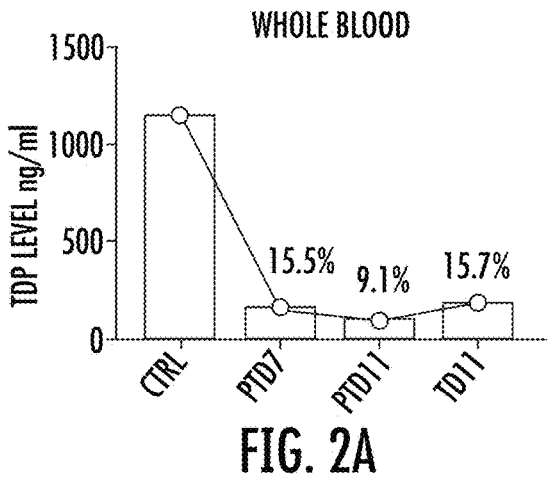
FIGS. 2A-2L show the comparison of TDP, TMP, and TM levels in brain, blood, liver, and kidney in mice of PTD model in Example 1. More particularly.
Figure 2B:
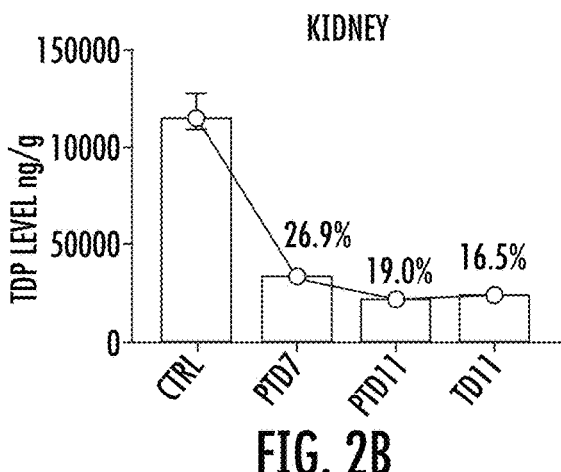
Figure 2C:
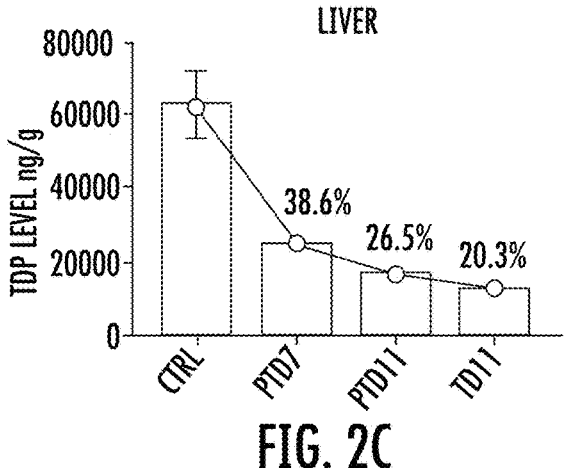
Figure 2D:
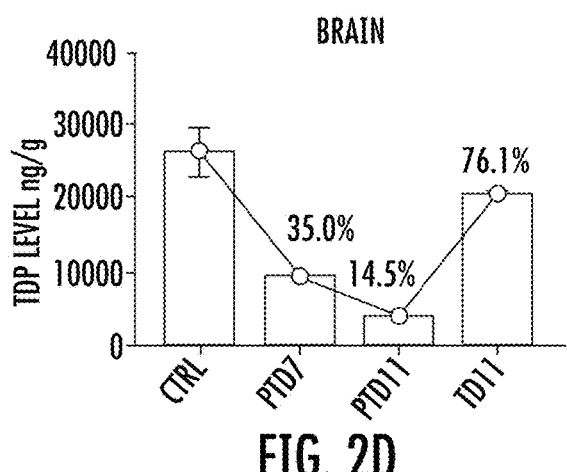
Figure 2E:
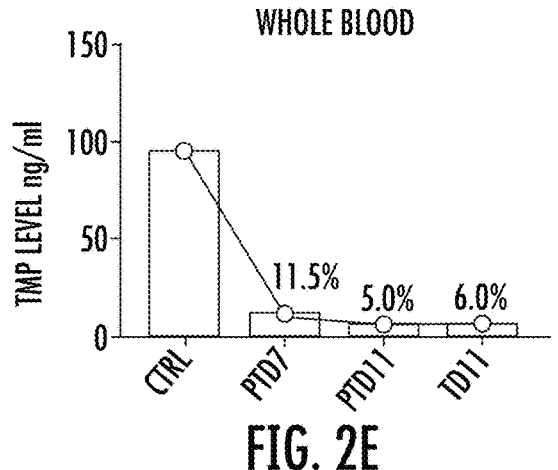
Figure 2F:
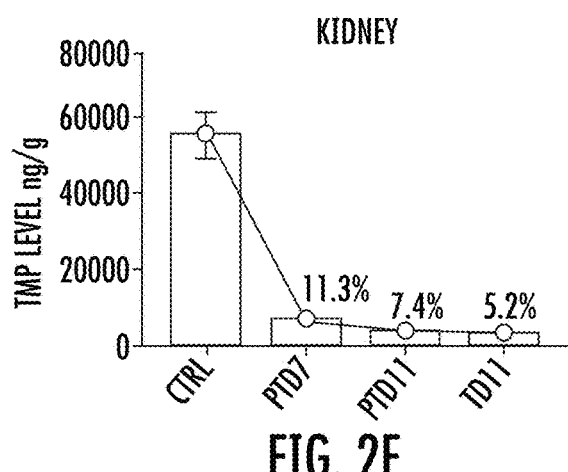
Figure 2G:
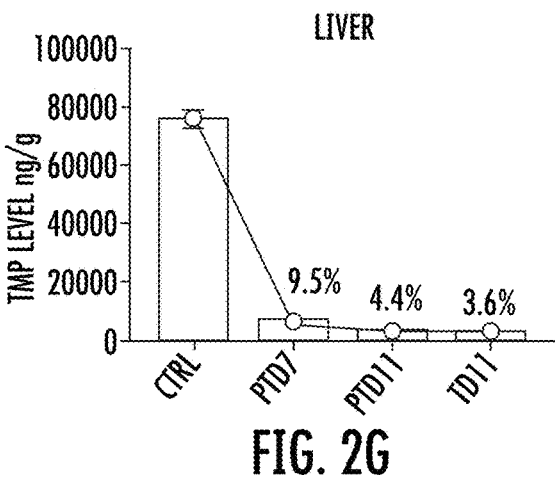
Figure 2H:
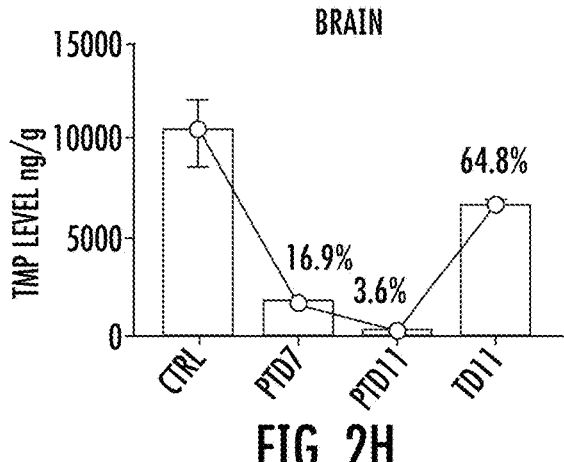
Figure 2I:
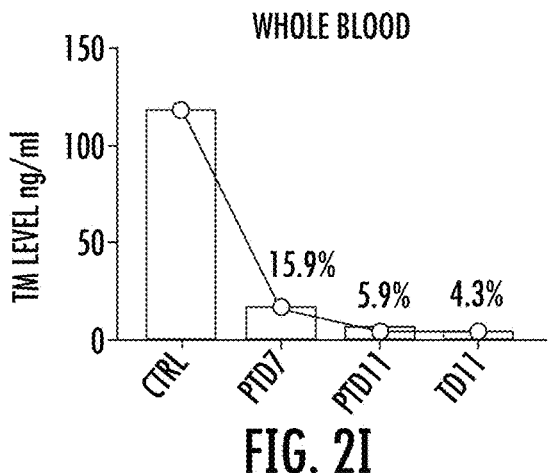
Figure 2J:
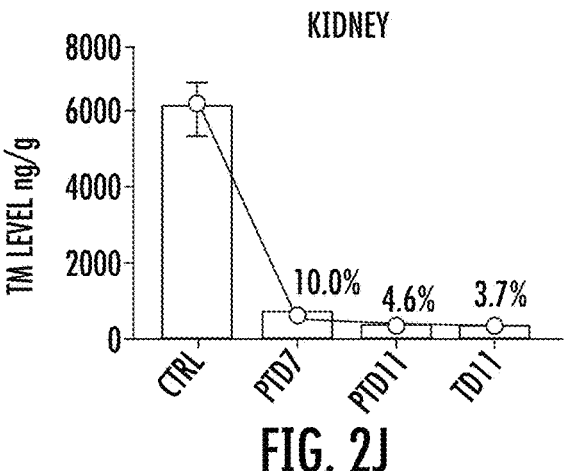
Figure 2K:
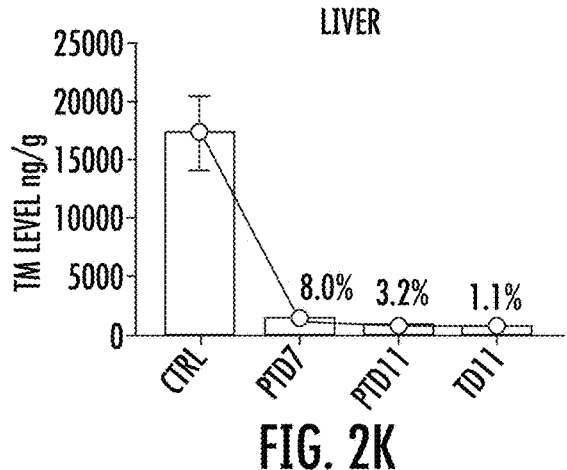
Figure 2L:
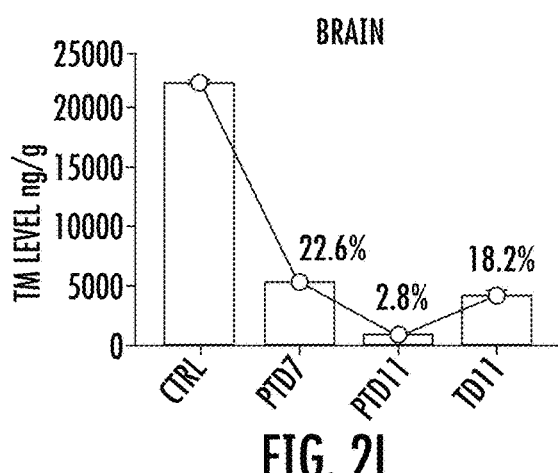

AD patients have multiple cascade pathophysiological changes in brain, wherein cerebral glucose metabolism disorder is the consistent pathological feature thereof, which is closely related to cognition regression, and appears many years before the clinical symptoms. Glucose is the primary energy substrate for cells in brain, and the intermediate products of glucose metabolism also provide substrates for the synthesis of neurotransmitter. Cerebral glucose metabolism mainly includes two processes, which are the trans-membrane transport and the intracellular metabolism of glucose, respectively. The intracellular glucose utilization disorder in AD patients is mainly caused by the decreased activities of key enzymes in glucose metabolism, i.e., decreased activities of transketolase, pyruvate dehydrogenase and α-ketoglutarate dehydrogenase. Thiamine diphosphate (TDP), the primary active form of thiamine, is the common coenzyme for these three key enzymes, and plays an important role in glucose metabolism. The decrease activities of three key enzymes above and the significant lack of TDP are specific and universal in AD patients, which are not present in patients with vascular dementia, fronto-temporal dementia and Parkinson. Thiamine pyrophosphate (TPK) is not only the key enzyme for TDP synthesis, but also the crucial factor for maintaining the homeostasis of TDP level in brain. The inventor of the invention, through further research, found that decrease in cerebral glucose metabolism caused by TDP deficiency is associated with the occurrence of AD, and AD is associated with the expression of TPK protein. Furthermore, the inhibition of TPK protein level in brain by TPK gene knockout can distinctly result in thiamine metabolism disorder, glucose metabolism disorder, and more importantly, can surprisingly induce AD-like neu-rodegenerative disease, encephalatrophy, pathological changes in Aβ and tau, neuroinflammation and neurovascu-lar disorder. Therefore, TPK gene or protein plays a very important role in AD, and thus, is a new target for treating and preventing AD. AD caused by TPK protein inhibition can be prevented by promoting the kinase activity and/or expression level of TPK protein in brain with TPK gene or protein as a target, thereby preventing. The animal model obtained with a method for the construction of an animal model by TPK gene knockout in a target animal can be used in the research of neurodegenerative diseases, particularly research of Alzheimer's disease, including research for disease-treatment and non-disease-treatment purposes. The research for non-disease-treatment in the animal model can specifically include, e.g., 1) investigating and/or studying the mechanism of neurodegenerative diseases; 2) preparing and/or screening the products capable of treating neurode-generative diseases; 3) seeking and verifying molecular markers capable of diagnosing and/or suggesting neurode-generative diseases.

In a particular embodiment of the invention, the promo-tion of the expression level of TPK protein in brain includes but not limited to preventing the expression of TPK protein from inhibition, increasing the expression level of TPK protein, increasing the activity of TPK protein or increasing the stability of TPK protein.

In a particular embodiment of the invention, the reagent promoting the expression level of TPK protein in brain may be a reagent regulating TPK protein, and may also be a reagent regulating TPK gene. The reagent includes but not limited to an accelerant, agonist, activator for promoting the expression level of TPK protein in brain. The reagent can be a compound, a chemical small molecule, a biomolecule and the like, specifically e.g., reagents regulating TPK protein, such as TPK binding protein, chemical agonist for TPK or enzymes for modifying TPK and the like, reagents regulat-ing TPK gene, such as a substance activating the replication or transcription of TPK gene, a substance increasing the expression of TPK gene, an up-regulating agent promoting the promoter of TPK gene, a protein for the specific over-expression of TPK gene.

In a particular embodiment of the invention, the medica-ment may contain a safe and effective dose of the reagent promoting the expression level of TPK protein in brain and a pharmaceutically acceptable carrier. The pharmaceutical preparation usually matches the administration, the dosage form of the preparation may be an injection, an oral prepa-ration (tablet, capsule, oral solution), a transdermal prepa-ration or a sustained-release preparation.

In a particular embodiment of the invention, the target animal is a non-human animal, including primate or rodent, etc., and further, mouse. The exon 4 in TPK gene is knocked out in the method, for mouse, the TPK gene has 9 exons in total, the ATG is located in exon 2, the termination codon is located in exon 9, and exon 4 is selected as the target for knockout, on one hand, the knocked-out exon sequence is not an integer multiple of three, and is capable resulting in frameshift mutations in the downstream reading frame; on the other hand, the closer the selected exon is located to the initiation site for translation, the less function of the gene can be retained.

A particular embodiment of the invention, in which modi-fied Cre-loxP recombinase system can be used to establish an animal model for the conditional knockout of TPK gene, includes the steps of: constructing a targeting vector for TPK-loxP gene knockout, introducing the targeting vector into a target animal to obtain a TPK-loxP+/+ target animal, crossing the TPK-loxP+/+ target animal with CamK2α-Cre/ERT2+/– target animal, obtaining CamK2α-Cre/ERT2+/–; TPK-loxP+/+ target animal with the conditional knockout of TPK gene. In particular, a Bacterial Artificial Chromosome can be used as the vector, and direct loxP sequences and the sequence of neomycin resistance gene can be inserted flanking the homologous sequence of a suitable exon; the targeting vector is transformed to an embryonic stem (ES) cell by electrotransformation; the ES cell transformed with correct sequence located at the correct site is identified by screening for antibiotic resistance, PCR and Southern blot; the positive clone is microinjected into the blastocyst of the target animal; and the successfully injected blastocyst is implanted to the uterus of the target animal to produce a chimeric target animal integrated with the ES cell; the obtained chimeric target animal is crossed with Flp tool target animal, the sequence of neomycin resistant gene is cut by induction, and TPK-loxP+/+ target animal with knockout potential can be obtained upon purification; Cre tool target animal with CamK2α in combination with mutant estrogen receptor element (LBD-ER) is selected for crossing with the above TPK-loxP+/+ target animal; and upon identification, the stably inherited CamK2α-Cre/ERT2+/–; TPK-loxP+/+ target animal is obtained.

In a particular embodiment of the invention, provided is a method for the construction of a targeting vector for an animal model, in which a Bacterial Artificial Chromosome is used as a vector, and direct loxP sequences are inserted at both ends of a sequence homologous to an exon of TPK gene together with a neomycin resistance gene sequence.

In a particular embodiment of the method for the construction of a targeting vector for an animal model of the invention, the exon is exon 4, and the following target sequence is constructed: "5'-homologous arm-loxP-exon 4-frt-Neo-frt-loxP-homologous arm-3'".

In a particular embodiment of the method for the construction of a targeting vector for an animal model of the invention, the sequence of the targeting vector is set forth in SEQ ID NO: 1.

In a particular embodiment of the invention, also provided is a targeting vector for an animal model obtained by the method for the construction of a targeting vector for an animal model above.

II. Definitions

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

"Thiamine pyrophosphokinase" or "TPK" is an enzyme catalyzing the reaction of converting thiamine (TM) into thiamine diphosphate (TDP).

"AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector"). The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

The genomic sequences of various serotypes of AAV, as well as the sequences of the native terminal repeats (TRs), Rep proteins, and capsid subunits are known in the art. Such sequences may be found in the literature or in public databases such as GenBank. See e.g., GENBANK® Accession Numbers NC_002077 (AAV-1), AF063497 (AAV-1), NC_001401 (AAV-2), AF043303 (AAV-2), NC_001729 (AAV-3), NC_001829 (AAV-4), U89790 (AAV-4), NC_006152 (AAV-5), AF513851 (AAV-7), AF513852 (AAV-8), and NC_006261 (AAV-8); the disclosures of which are incorporated by reference herein for teaching AAV nucleic acid and amino acid sequences.

An "rAAV vector" used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two, AAV inverted terminal repeat sequences (ITRs). The term rAAV vector encompasses both rAAV vector particles and rAAV vector plasmids. An rAAV vector may either be single-stranded (ssAAV) or self-complementary (scAAV).

"Packaging" refers to a series of intracellular events that result in the assembly and encapsidation of an AAV particle.

AAV "rep" and "cap" genes refer to polynucleotide sequences encoding replication and encapsidation proteins of adeno-associated virus. AAV rep and cap are referred to herein as AAV "packaging genes."

A "helper virus" for AAV refers to a virus that allows AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

"Helper virus function(s)" refers to function(s) encoded in a helper virus genome which allow AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans. For example, a plasmid or other expression vector comprising nucleotide sequences encoding one or more adenoviral proteins is transfected into a producer cell along with an rAAV vector.

Lentiviral vector is a viral vector derived from HIV-1. "Recombinant lentiviral vector" or "recombinant lentiviral vector particles" refers to the recombinant viral particles or virus-like particles generated in a host cell or production cells following transfection by the plasmid vectors consisting of the transfer vector, the envelope vector encoding the selected envelope protein and the packaging vector providing lentiviral proteins in trans (such as lentiviral GAG and POL proteins, in particular mutated POL protein for the avoidance of integration) according to methods well-known in the art.

Virus-like particles result from incomplete assembly of the proteins present for encapsidation of the recombinant lentiviral genome in a way that does not enable the formation of true viral particles.

The term "polynucleotide" refers to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

Nucleic acid hybridization reactions can be performed under conditions of different "stringency". Conditions that increase stringency of a hybridization reaction of widely known and published in the art. See, e.g., Sambrook et al. Molecular Cloning, A Laboratory Manual, 2nd Ed., Cold Spring Harbor Laboratory Press, Cold Spring Harbor, N.Y., 1989, herein incorporated by reference.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wisconsin, USA, a wholly owned subsidiary of Oxford Molecular Group, Inc.

A "gene" refers to a polynucleotide containing at least one open reading frame that is capable of encoding a particular protein after being transcribed and translated.

"Recombinant," as applied to a polynucleotide means that the polynucleotide is the product of various combinations of cloning, restriction or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

"Operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

An "expression vector" is a vector comprising a region which encodes a polypeptide of interest, and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

"Heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. Thus, for example, an rAAV that includes a heterologous nucleic acid encoding a heterologous gene product is an rAAV that includes a nucleic acid not normally included in a naturally-occurring, wild-type AAV, and the encoded heterologous gene product is a gene product not normally encoded by a naturally-occurring, wild-type AAV.

The terms "polypeptide," "peptide," and "protein" are used interchangeably herein to refer to polymers of amino acids of any length. The terms also encompass an amino acid polymer that has been modified; for example, disulfide bond formation, glycosylation, lipidation, phosphorylation, or conjugation with a labeling component.

The modification also comprises the modification to the sequence of the polypeptide, including, but not limited to, the substitution, deletion, insertion and/or addition of one or more amino acids.

An "isolated" plasmid, nucleic acid, vector, virus, virion, host cell, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, i.e., arresting its development; and (c) relieving the disease, i.e., causing regression of the disease.

The terms "individual," "host," "subject," and "patient" are used interchangeably herein, and refer to a mammal, including, but not limited to, human and non-human primates, including simians and humans; mammalian sport animals (e.g., horses); mammalian farm animals (e.g., sheep, goats, etc.); mammalian pets (dogs, cats, etc.); and rodents (e.g., mice, rats, etc.).

III. Isolated Polynucleotides

The present invention provides an isolated polynucleotide comprising an expression cassette comprising a polynucleotide encoding TPK operably linked to a promoter.

The TPK can be a TPK from human or a non-human animal, such as a non-human mammal. Examples of a TPK from a non-human mammal include, but are not limited to, a TPK from a non-human primate such as monkey, horse, bovine, sheep, goat, pig, dog, cat, mouse, and rat.

In some embodiments, the TPK is a wild-type TPK. In some embodiments, the TPK is a mouse TPK or human TPK.

In some embodiments, the TPK comprises the amino acid sequence of SEQ ID NO: 17.

In some embodiments, the polynucleotide encoding the TPK comprises the nucleotide sequence of SEQ ID NO: 18. In some embodiments, the TPK consists of the amino acid sequence of SEQ ID NO: 17. In some embodiments, the polynucleotide encoding the TPK consists of the nucleotide sequence of SEQ ID NO: 18.

In some embodiments, the TPK is a modified TPK comprising the substitution, insertion, deletion and/or addition of one or more amino acids compared to the initial TPK, wherein the activity of the modified TPK is at least 10%, 20%, 30%, 40%, 50%, 60%, 70%, 80%, 90%, 100%, 110%, 120%, 130%, 140%, 150%, 200%, 250%, 300% or higher of that of the initial TPK. In some embodiments, the modified TPK comprises substitution, insertion, deletion and/or addition of 1, 2, 3, 4, 5, 6, 7, 8, 9, 10 or more amino acids compared to the initial TPK. In some embodiments, the modified TPK has an identity of at least 80%, 90%, 95%, 96%, 97%, 98%, 99% or more to the initial TPK.

The initial TPK can be a wild-type TPK or a modified TPK. In some embodiments, the initial TPK is a wild-type mouse TPK or a wild-type human TPK.

In some embodiments, the initial TPK comprises the amino acid sequence of SEQ ID NO: 17. In some embodiments, the initial TPK consists of the amino acid sequence of SEQ ID NO: 17.

In some embodiments, the promoter is a neuron-specific promoter. In some embodiments, the promoter comprises the nucleotide sequence of SEQ ID NO: 19. In some embodiments, the promoter consists of the nucleotide sequence of SEQ ID NO: 19. In some embodiments, the promoter comprises a nucleotide sequence which has an identity of at least 70%, 80%, 90%, 95%, 96%, 97%, 98%, 99% or more to SEQ ID NO: 19. In some embodiments, the promoter consists of a nucleotide sequence which has an identity of at least 70%, 80%, 90%, 95%, 96%, 97%, 98%, 99% or more to SEQ ID NO: 19.

In some embodiments, the promoter is a eukaryotic strong promoter, e.g., a cytomegalovirus (CMV) promoter. In some embodiments, the promoter comprises the nucleotide sequence of SEQ ID NO: 23. In some embodiments, the promoter consists of the nucleotide sequence of SEQ ID NO: 23. In some embodiments, the promoter comprises a nucleotide sequence which has an identity of at least 70%, 80%, 90%, 95%, 96%, 97%, 98%, 99% or more to SEQ ID NO: 23. In some embodiments, the promoter consists of a nucleotide sequence which has an identity of at least 70%, 80%, 90%, 95%, 96%, 97%, 98%, 99% or more to SEQ ID NO: 23.

The expression cassette can further comprise an additional control sequence, such as an enhancer, an intron, a mRNA stabilizing sequence, and a polyadenylation signal sequence.

In some embodiments, the expression cassette further comprises an mRNA stabilizing sequence, such as a WPRE element. In some embodiments, the WPRE element comprises the nucleotide sequence of SEQ ID NO: 20. In some embodiments, the WPRE element consists of the nucleotide sequence of SEQ ID NO: 20. In some embodiments, the WPRE element comprises a nucleotide which has an identity of at least 70%, 80%, 90%, 95%, 96%, 97%, 98%, 99% or more to SEQ ID NO: 20. In some embodiments, the WPRE element consists of a nucleotide which has an identity of at least 70%, 80%, 90%, 95%, 96%, 97%, 98%, 99% or more to SEQ ID NO: 20.

In some embodiments, the WPRE element is downstream of the polynucleotide encoding the TPK.

In some embodiments, the expression cassette further comprises a polyadenylation signal sequence, for example, but not limited to, the polyadenylation signal sequence of human growth factor gene and the polyadenylation signal sequence of rabbit globulin gene. In some embodiments, the expression cassette further comprises a polyadenylation signal sequence of human growth factor gene. In some embodiments, the polyadenylation signal sequence comprises the nucleotide sequence of SEQ ID NO: 21. In some embodiments, the polyadenylation signal sequence consists of the nucleotide sequence of SEQ ID NO: 21. In some embodiments, the polyadenylation signal sequence comprises a nucleotide sequence which has an identity of at least 70%, 80%, 90%, 95%, 96%, 97%, 98%, 99% or more to SEQ ID NO: 21. In some embodiments, the polyadenylation signal sequence consists of a nucleotide sequence which has an identity of at least 70%, 80%, 90%, 95%, 96%, 97%, 98%, 99% or more to SEQ ID NO: 21.

In some embodiments, the polyadenylation signal sequence is downstream of the WPRE element.

The polynucleotide can comprise the genome of an rAAV. Therefore, in some embodiments, the expression cassette is flanked by the ITRs of AAV. Non-limiting examples of the ITRs include ITRs derived from AAV-1, AAV-2, AAV-3, AAV-4, AAV-5, AAV-6, AAV-7, AAV-8, AAV-9, avian AAV, bovine AAV, canine AAV, equine AAV, primate AAV, non-primate AAV, and ovine AAV. In some embodiments, the ITR is the ITR of AAV-2. In some embodiments, the 5' ITR is identical to the 3' ITR. In some embodiments, the 5' ITR is different from the 3' ITR.

In some embodiments, both the 5' ITR and the 3' ITR are ITR130, e.g., comprising the nucleotide sequence of SEQ ID NO: 22. In some embodiments, the 5' ITR and the 3' ITR 3' consist of SEQ ID NO: 22, respectively. In some embodiments, the 5' ITR and the 3' ITR comprises a nucleotide sequence having an identity of at least 70%, 80%, 90%, 95%, 96%, 97%, 98%, 99% or more to SEQ ID NO: 22, respectively. In some embodiments, the 5' ITR and the 3' ITR consist of a nucleotide sequence having an identity of at least 70%, 80%, 90%, 95%, 96%, 97%, 98%, 99% or more to SEQ ID NO: 22, respectively.

In some embodiments, the polynucleotide comprises, from 5' to 3', SEQ ID NO: 19, SEQ ID NO: 18, SEQ ID NO: 20, and SEQ ID NO: 21. In some embodiments, the polynucleotide comprises, from 5' to 3', SEQ ID NO: 22, SEQ ID NO: 19, SEQ ID NO: 18, SEQ ID NO: 20, SEQ ID NO: 21, and SEQ ID NO: 22.

In some embodiments, the polynucleotide comprises, from 5' to 3', SEQ ID NO: 23, SEQ ID NO: 18, SEQ ID NO: 20, and SEQ ID NO: 21.

The present invention also provides a vector comprising the polynucleotide of the present invention. In some embodiments, the vector is a eukaryotic expression vector.

In some embodiments, the vector is a vector that provides the rAAV genome in the packaging of an rAAV, i.e., a transgene plasmid.

In some embodiments, the vector is a vector that provides the Lentivirus genome in the packaging of a Lentivirus, i.e., a transgene plasmid.

IV. Recombinant Viruses

The present invention provides a recombinant adeno-associated virus (rAAV) or a recombinant Lentivirus comprising in the genome an expression cassette comprising a polynucleotide encoding TPK operably linked to a promoter.

The TPK can be a TPK from human or a non-human animal, such as a non-human mammal. Examples of a TPK from a non-human mammal include, but are not limited to, a TPK from a non-human primate such as monkey, horse, bovine, sheep, goat, pig, dog, cat, mouse, and rat.

In some embodiments, the TPK is a wild-type TPK. In some embodiments, the TPK is a mouse TPK or human TPK.

In some embodiments, the TPK comprises the amino acid sequence of SEQ ID NO: 17. In some embodiments, the polynucleotide encoding the TPK comprises the nucleotide sequence of SEQ ID NO: 18. In some embodiments, the TPK consists of the amino acid sequence of SEQ ID NO: 17. In some embodiments, the polynucleotide encoding the TPK consists of the nucleotide sequence of SEQ ID NO: 18.

In some embodiments, the TPK is a modified TPK comprising the substitution, insertion, deletion and/or addition of one or more amino acids compared to the initial TPK, wherein the activity of the modified TPK is at least 10%, 20%, 30%, 40%, 50%, 60%, 70%, 80%, 90%, 100%, 110%, 120%, 130%, 140%, 150%, 200%, 250%, 300% or higher of that of the initial TPK. In some embodiments, the modified TPK comprises substitution, insertion, deletion and/or addition of 1, 2, 3, 4, 5, 6, 7, 8, 9, 10 or more amino acids compared to the initial TPK. In some embodiments, the modified TPK has an identity of at least 80%, 90%, 95%, 96%, 97%, 98%, 99% or more to the initial TPK.

The initial TPK can be a wild-type TPK or a modified TPK. In some embodiments, the initial TPK is a wild-type mouse TPK or a wild-type human TPK.

In some embodiments, the initial TPK comprises the amino acid sequence of SEQ ID NO: 17. In some embodiments, the initial TPK consists of the amino acid sequence of SEQ ID NO: 17.

In some embodiments, the promoter is a neuron-specific promoter. In some embodiments, the promoter comprises the nucleotide sequence of SEQ ID NO: 19. In some embodiments, the promoter consists of the nucleotide sequence of SEQ ID NO: 19. In some embodiments, the promoter comprises a nucleotide sequence which has an identity of at least 70%, 80%, 90%, 95%, 96%, 97%, 98%, 99% or more to SEQ ID NO: 19. In some embodiments, the promoter consists of a nucleotide sequence which has an identity of at least 70%, 80%, 90%, 95%, 96%, 97%, 98%, 99% or more to SEQ ID NO: 19.

In some embodiments, the promoter is a eukaryotic strong promoter, e.g., a cytomegalovirus (CMV) promoter. In some embodiments, the promoter comprises the nucleotide sequence of SEQ ID NO: 23. In some embodiments, the promoter consists of the nucleotide sequence of SEQ ID NO: 23. In some embodiments, the promoter comprises a nucleotide sequence which has an identity of at least 70%, 80%, 90%, 95%, 96%, 97%, 98%, 99% or more to SEQ ID NO: 23. In some embodiments, the promoter consists of a nucleotide sequence which has an identity of at least 70%, 80%, 90%, 95%, 96%, 97%, 98%, 99% or more to SEQ ID NO: 23.

The expression cassette can further comprise an additional control sequence, such as an enhancer, an intron, a mRNA stabilizing sequence, and a polyadenylation signal sequence.

In some embodiments, the expression cassette further comprises an mRNA stabilizing sequence, such as a WPRE element. In some embodiments, the WPRE element comprises the nucleotide sequence of SEQ ID NO: 20. In some embodiments, the WPRE element consists of the nucleotide sequence of SEQ ID NO: 20. In some embodiments, the WPRE element comprises a nucleotide which has an identity of at least 70%, 80%, 90%, 95%, 96%, 97%, 98%, 99% or more to SEQ ID NO: 20. In some embodiments, the WPRE element consists of a nucleotide which has an identity of at least 70%, 80%, 90%, 95%, 96%, 97%, 98%, 99% or more to SEQ ID NO: 20.

In some embodiments, the WPRE element is downstream of the polynucleotide encoding the TPK.

In some embodiments, the expression cassette further comprises a polyadenylation signal sequence, for example, but not limited to, the polyadenylation signal sequence of human growth factor gene and the polyadenylation signal sequence of rabbit globulin gene. In some embodiments, the expression cassette further comprises a polyadenylation signal sequence of human growth factor gene. In some embodiments, the polyadenylation signal sequence comprises the nucleotide sequence of SEQ ID NO: 21. In some embodiments, the polyadenylation signal sequence consists of the nucleotide sequence of SEQ ID NO: 21. In some embodiments, the polyadenylation signal sequence comprises a nucleotide sequence which has an identity of at least 70%, 80%, 90%, 95%, 96%, 97%, 98%, 99% or more to SEQ ID NO: 21. In some embodiments, the polyadenylation signal sequence consists of a nucleotide sequence which has an identity of at least 70%, 80%, 90%, 95%, 96%, 97%, 98%, 99% or more to SEQ ID NO: 21.

In some embodiments, the polyadenylation signal sequence is downstream of the WPRE element.

The polynucleotide can comprise the genome of an rAAV. Therefore, in some embodiments, the expression cassette is flanked by the ITRs of AAV. Non-limiting examples of the ITRs include ITRs derived from AAV-1, AAV-2, AAV-3, AAV-4, AAV-5, AAV-6, AAV-7, AAV-8, AAV-9, avian AAV, bovine AAV, canine AAV, equine AAV, primate AAV, non-primate AAV, and ovine AAV. In some embodiments, the ITR is the ITR of AAV-2. In some embodiments, the 5' ITR is identical to the 3' ITR. In some embodiments, the 5' ITR is different from the 3' ITR.

In some embodiments, both the 5' ITR and the 3' ITR are ITR130, e.g., comprising the nucleotide sequence of SEQ ID NO: 22. In some embodiments, the 5' ITR and the 3' ITR 3' consist of SEQ ID NO: 22, respectively. In some embodiments, the 5' ITR and the 3' ITR comprises a nucleotide sequence having an identity of at least 70%, 80%, 90%, 95%, 96%, 97%, 98%, 99% or more to SEQ ID NO: 22, respectively. In some embodiments, the 5' ITR and the 3' ITR consist of a nucleotide sequence having an identity of at least 70%, 80%, 90%, 95%, 96%, 97%, 98%, 99% or more to SEQ ID NO: 22, respectively.

In some embodiments, the rAAV genome comprises, from 5' to 3', SEQ ID NO: 19, SEQ ID NO: 18, SEQ ID NO: 20, and SEQ ID NO: 21. In some embodiments, the polynucleotide comprises, from 5' to 3', SEQ ID NO: 22, SEQ ID NO: 19 SEQ ID NO: 18, SEQ ID NO: 20, SEQ ID NO: 21, and SEQ ID NO: 22.

In some embodiments, the Lentivirus genome comprises, from 5' to 3', SEQ ID NO: 23, SEQ ID NO: 18, SEQ ID NO: 20, and SEQ ID NO: 21.

The rAAV can be an AAV-1, an AAV-2, an AAV-3, an AAV-4, an AAV-5, an AAV-6, an AAV-7, an AAV-8, an AAV-9, an avian AAV, a bovine AAV, a canine AAV, an equine AAV, a primate AAV, a non-primate AAV, and an ovine AAV. In some embodiments, the rAAV is an rAAV of serotype AAV_PHP eB.

It is known in the art to package rAAV with a system comprising three plasmids: i) a transgene plasmid comprising the rAAV genome encoding a gene product of interest; ii) a packaging plasmid encoding REP and/or CAP proteins; and iii) a helper plasmid (see e.g., Crosson S M et al., Helper-free Production of Laboratory Grade AAV and Purification by Iodixanol Density Gradient Centrifugation. Mol Ther Methods Clin Dev. 2018; 10:1-7). The packaging involves the introduction of the system into a host cell.

The packaging system for Lentivirus is known in the art, consisting of the plasmid vectors consisting of the transfer vector (transgene plasmid), the envelope vector encoding the selected envelope protein and the packaging vector providing lentiviral proteins in trans (such as lentiviral GAG and POL proteins, in particular mutated POL protein for the avoidance of integration) according to methods well-known in the art. The packaging of Lentivirus involves the introduction of the system into a host cell.

The present invention further provides a host cell comprising the polynucleotide, vector, rAAV or recombinant Lentivirus of the present invention. When the host cell of the present invention is used to package the rAAV or recombinant Lentivirus of the present invention, it is referred to as a "packaging cell". In some embodiments, the host cell is stably genetically modified with the nucleic acid or vector of the present invention. In other embodiments, the host cell is transiently genetically modified with the nucleic acid or vector of the present invention.

The polynucleotide or the vector of the present invention can be introduced into the host cell stably or transiently using defined techniques including, but not limited to, electroporation, calcium phosphate precipitation, liposome-mediated transfection, and the like. For stable transformation, the subject nucleic acid will typically be operably linked to a selectable marker, such as neomycin resistance gene and the like.

The host cell of the present invention can be derived from mammalian cells. Suitable mammalian cells include, but are not limited to, primary cells and cell lines, wherein suitable cell lines include, but are not limited to, 293 cells, COS cells, HeLa cells, Vero cells, 3T3 mouse fibroblasts, C3H10T1/2 fibroblasts, CHO cells, etc. Non-limiting examples of suitable host cells include, for example, HeLa cells (e.g., American Type Culture Collection (ATCC) No. CCL-2), CHO cells (e.g., ATCC No. CRL9618, CCL61, CRL9096), 293 cells (e.g., ATCC No. CRL-1573), Vero cells, NIH3T3 cells (eg, ATCC No. CRL-1658), Huh-7 cells, BHK cells (e.g., ATCC No. CCL10), PC12 cells (ATCC No. CRL1721) COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

V. Pharmaceutical Compositions

The present invention provides a pharmaceutical composition comprising: the polynucleotide, vector, rAAV or recombinant Lentivirus of the present invention; and a pharmaceutically acceptable carrier, diluent, excipient or buffer. In some embodiments, a pharmaceutically acceptable carrier, diluent, excipient or buffer is suitable for use in humans.

Such excipients, carriers, diluents, and buffers include any agent that can be administered without abnormal toxicity. Pharmaceutically acceptable excipients include, but are not limited to, liquids such as water, saline, glycerol, and ethanol. Included therein may be pharmaceutically acceptable salts such as mineral acid salts such as hydrochlorides, hydrobromides, phosphates, sulfates, and the like; and salts of organic acids such as acetates, propionates, malonates, Benzoate and the like. In addition, auxiliary substances such as wetting or emulsifying agents, pH buffering substances and the like may be present in such vehicles. A wide variety of pharmaceutically acceptable excipients are known in the art and need not be discussed in detail herein. Pharmaceutically acceptable excipients have been described in detail in various publications including, for example, A. Gennaro (2000) "Remington: The Science and Practice of Pharmacy," 20th Edition, Lippincott, Williams, & Wilkins; Pharmaceutical Dosage Forms and Drug Delivery Systems (1999) Editing by H C Ansel et al, 7th edition, Lippincott, Williams, & Wilkins; and Handbook of Pharmaceutical Excipients (2000) A H Kibbe et al., 3rd edition, Amer. Pharmaceutical Assoc.

VI. Prevention and Treatment of Diseases

The present invention provides a method of promoting glucose metabolism, or preventing or treating a glucose metabolism disorder, preferably glucose metabolism disorder in the brain, comprising increasing the TPK activity, preferably in brain. The present invention provides a method of treating or preventing Alzheimer's disease, comprising increasing the TPK activity in brain.

The present invention provides a method of promoting glucose metabolism, or preventing or treating a glucose metabolism disorder, preferably glucose metabolism disorder in the brain, comprising administering the polynucleotide, vector, rAAV, recombinant Lentivirus or pharmaceutical composition of the present invention to a subject or patient in need thereof. The present invention provides a method of treating or preventing Alzheimer's disease, comprising administering the polynucleotide, vector, rAAV, recombinant Lentivirus or pharmaceutical composition of the present invention to a subject or patient in need thereof. In some embodiments, the polynucleotide, vector, rAAV, recombinant Lentivirus or pharmaceutical composition is administered intravenously, intracerebrally, or intrathecally. In some embodiments, the subject of patient is a human.

The present invention also provides the use of the polynucleotide, vector, rAAV, recombinant Lentivirus or pharmaceutical composition of the present invention in the preparation of a medicament for promoting glucose metabolism, or preventing or treating a glucose metabolism disorder, preferably glucose metabolism disorder in the brain.

The present invention also provides the use of the polynucleotide, vector, rAAV, recombinant Lentivirus or pharmaceutical composition of the present invention in the preparation of a medicament for treating or preventing Alzheimer's disease. In some embodiments, the medicament is administered intravenously, intracerebrally, or intrathecally. In some embodiments, the medicament is administered to a human.

Provided in the present invention is also the polynucleotide, vector, rAAV, recombinant Lentivirus or pharmaceutical composition of the present invention for use in promoting glucose metabolism, or preventing or treating a glucose metabolism disorder, preferably a glucose metabolism disorder in the brain. Provided in the present invention is also the polynucleotide, vector, rAAV, recombinant Lentivirus or pharmaceutical composition of the present invention for use in treating or preventing Alzheimer's disease. In some embodiments, the polynucleotide, vector, rAAV, recombinant Lentivirus or pharmaceutical composition is administered intravenously, intracerebrally, or intrathecally. In some embodiments, the rAAV, recombinant Lentivirus or pharmaceutical composition is administered to a human.

The prevention or treatment of Alzheimer's disease includes the prevention, alleviation or elimination of AD symptoms, such as AD-like neurodegenerative disease, encephalatrophy, pathological changes in Aβ and tau, neuroinflammation and neurovascular disorder, or slowing the progression of AD.

AD involves the damage to various brain areas. The viruses of the present invention can specifically and effectively penetrate the blood-brain barrier, and acts widely on various brain areas. In clinical application, the rAAV of the present invention can be administered by direct injection across the blood-brain barrier (e.g., intracerebral injection or intrathecal injection), or an effect equivalent to that of direct brain injection can also be achieved by peripherally intravenous injection. In addition, the present invention differs from other gene therapy in only introducing the compensatory expression of foreign TPK without involving the endogenous TPK, much less the editing of other genes, which can greatly reduce additional risks. More importantly, the present invention introduces exogenous TPK with a high activity, and achieves beneficial therapeutic effects.

EXAMPLES

The invention is further illustrated in view of the following Examples. The present invention will be more clearly understood by the skilled in the art through the following Examples. It should be understood that the following Examples are intended to exemplify the embodiments of the present invention, but not to limit the scope of the present invention. Unless otherwise specified, the methods used in the present invention are conventional methods in the art, and the experimental materials used are also commercially available.

Example 1

Figure 3:
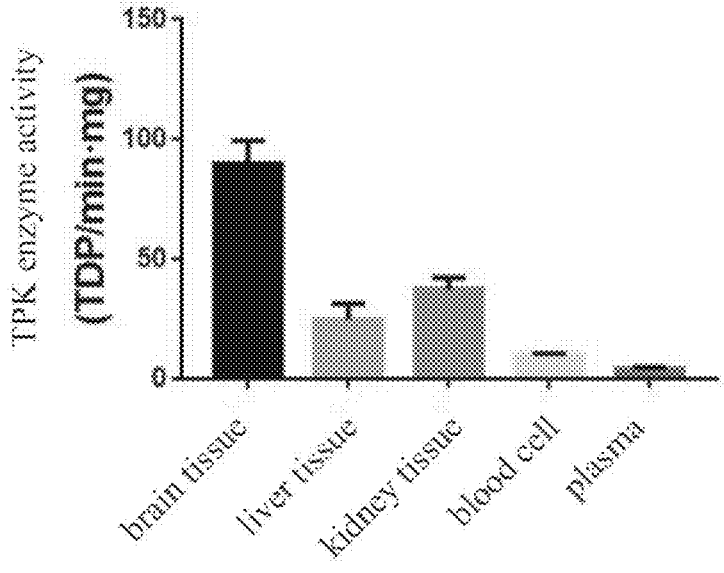
FIG. 3 shows the comparison of the activities of TPK enzyme in the brain and blood, liver, and kidney in normal mice in Example 1.

Experiments were performed in simple Thiamine diet-deprivation (TD) model and Thiamine diet-deprivation in combination with pyrithiamine injection (PTD) model, respectively. The dynamic changes in TD and PTD models were followed. Six groups (n=4) including TD 11 days, 18 days, 26 days and PTD 7 days, 11 days, were set for comparison. 3-month-old C57 mice born on the same day and having similar body weights were selected. Different time points for starting modeling were selected depending on the grouping, and the modelings were finally completed on the same day as well as the sampling. TD models: modeling for 11 days, 18 days and 26 days, respectively, with normal drinking water, and Thiamine-deficient diet; PTD models: modeling for 7 days and 11 days, respectively, with normal drinking water, Thiamine-deficient diet, and daily intraperitoneal injection of 0.1 mg/mL PT (pyrithiamine) at a dose of 500 μg/(kg·d); control group: normal drinking water, normal feed, and intraperitoneal injection of normal saline. Once the modeling was completed, the mice were anesthetized by the inhalation of isoflurane, the eyes were removed, the blood was sampled into tubes with heparin anticoagulant, which were then overturned rapidly for blending. Equal volume of 7.5% PCA was added to 150 μL whole blood, which were blended on vortex. The mice were rapidly sacrificed by cervical dislocation on ice, and the brain, kidney, liver tissues and the like, were sampled, and weighed. The weights of the tissues were recorded. The tissues were mixed with $KH_2PO_4$ at a ratio of tissue (mg): $KH_2PO_4$ (μL)=100:900, ground for 90 seconds with a tissue grinder, at 70 Hz, subjected to ice bath after full crushing for 30 minutes, and stored at −80° C. until use. TDP, TMP, and TM (Thiamine) levels were determined by high performance liquid chromatography. In TD and PTD models, the comparisons of TDP, TMP, and TM activities in brain, blood, liver, and kidney in mice were shown in FIGS. 1A-1L and FIGS. 2A-2L, and the comparison of TPK activities in brain, blood, liver, and kidney in normal mice was shown in FIG. 3.

According to the above experiments, it was found in TD models that as compared with blood, liver and kidney, a feature of significantly slower reduction of TDP level was exhibited in brain, indicating the protection against the loss of TDP in brain (see FIGS. 1A-1L). In PTD models, PT, a specific inhibitor to TPK, can damage homeostasis of TDP in the body, especially TDP level in brain (see FIGS. 2A-2L). It was found by further detections of TPK activities in different tissues of normal mice that TPK activity was the highest in brain (FIG. 3), and thus, it can be presumed that the high activity of TPK specific for brain tissue was the key for maintaining TDP homeostasis in brain.

Example 2

1. Construction of the Targeting Vector

Figure 4:
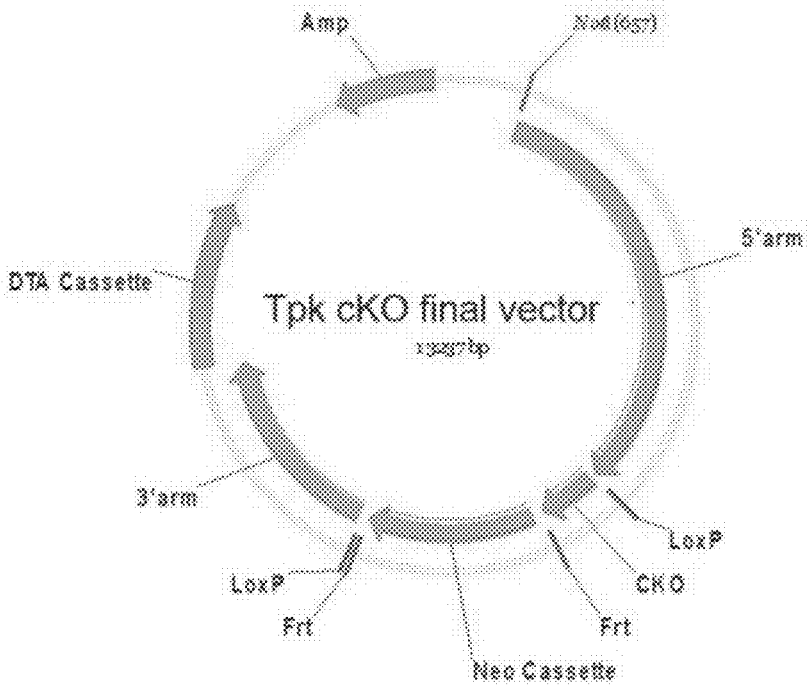
FIG. 4 shows plasmid map of the targeting vector used in Example 2, in which Amp is Ampicillin resistance gene sequence, NotI is restriction endonuclease target site, 3'-arm and 5'-arm are homologous sequences flanking exon 4, Neo Cassette is neomycin resistance gene coding sequence, loxP sequence is for locating and targeting the fragment to be knocked out, Frt is the recognition site for Flp to cut Neo sequence.

Bacterial Artificial Chromosome (BAC) was used as the vector, and the target sequence "5'-homologous arm-loxP-exon 4-frt-Neo-frt-loxP-homologous arm-3'", constructed with introns flanking exon 4 as homologous arms, is inserted to construct a targeting vector for gene knockout (see FIG. 4).

Figure 5:
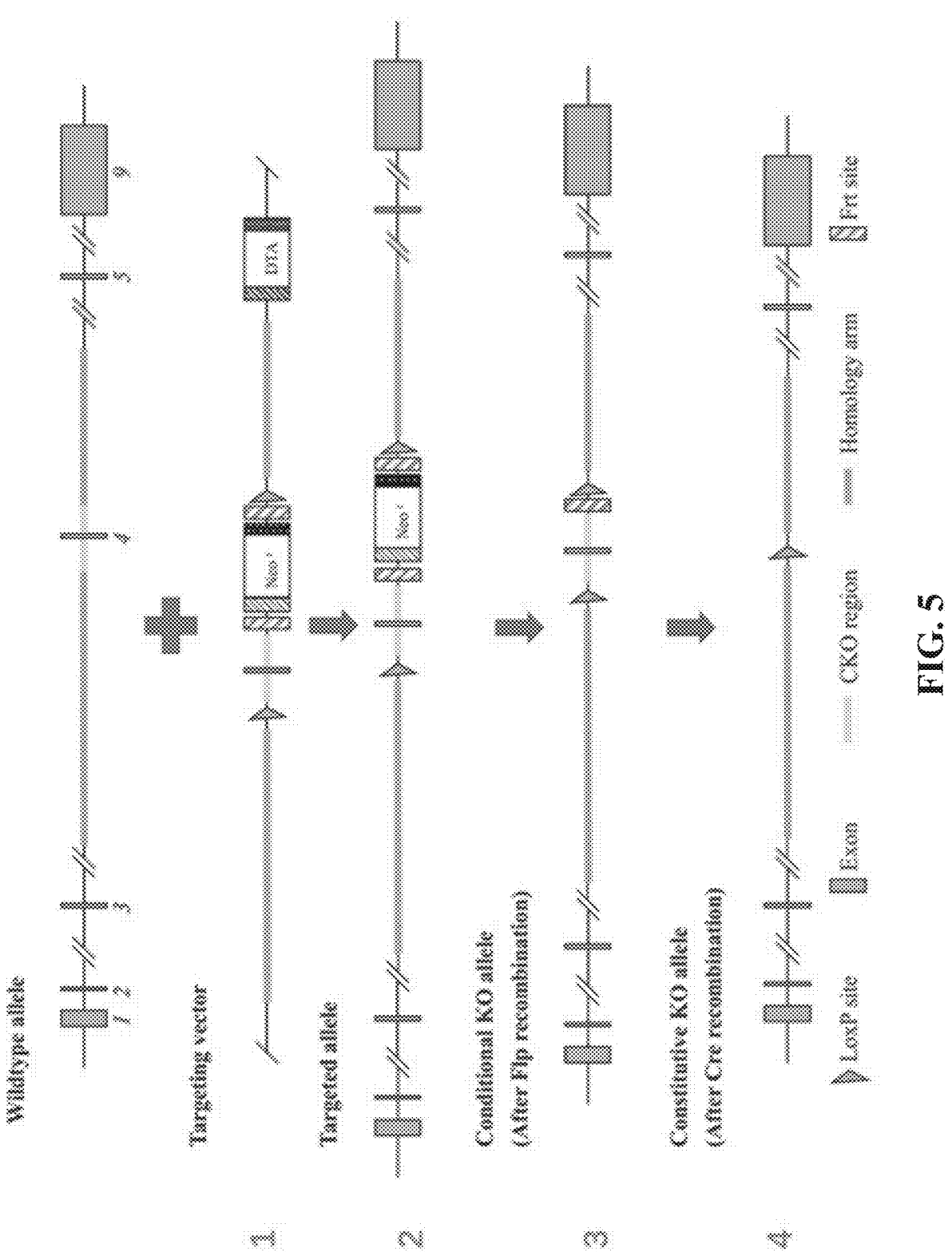
FIG. 5 shows a brief flow chart for the preparation of CamK2α-Cre/ERT2+/−; TPK-loxP+/+ mice in Example 2, in which 1 is the electro-transformation of the obtained targeting vector into an embryonic stem cell; 2 is selecting the correct positive clones; 3 is crossing with Flp mice to remove Neo sequence and obtain CamK2α-Cre/ERT2+/−; Tpk-loxP+/+ mice.
Figures 6A, 6B:
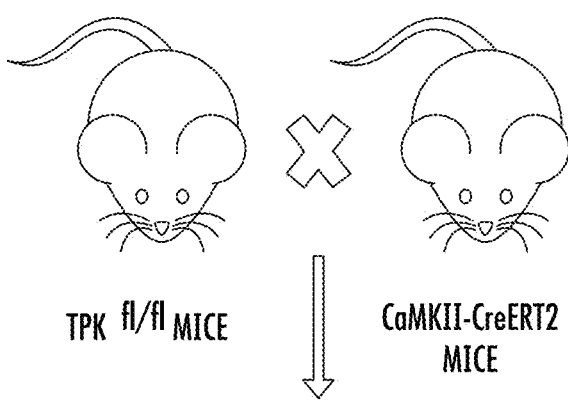
Figure 6C:
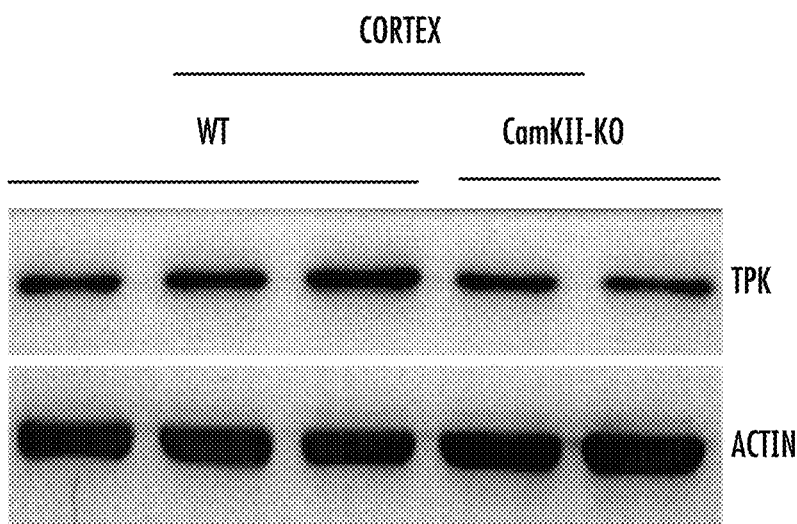
Figure 6D:
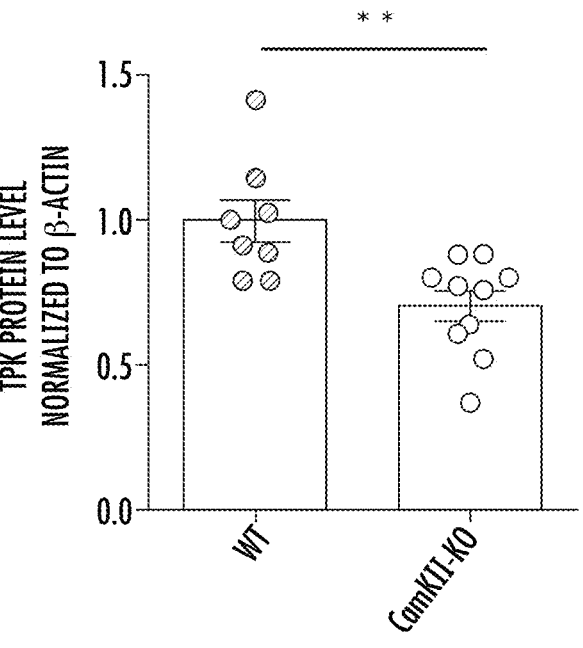
Figure 6E:
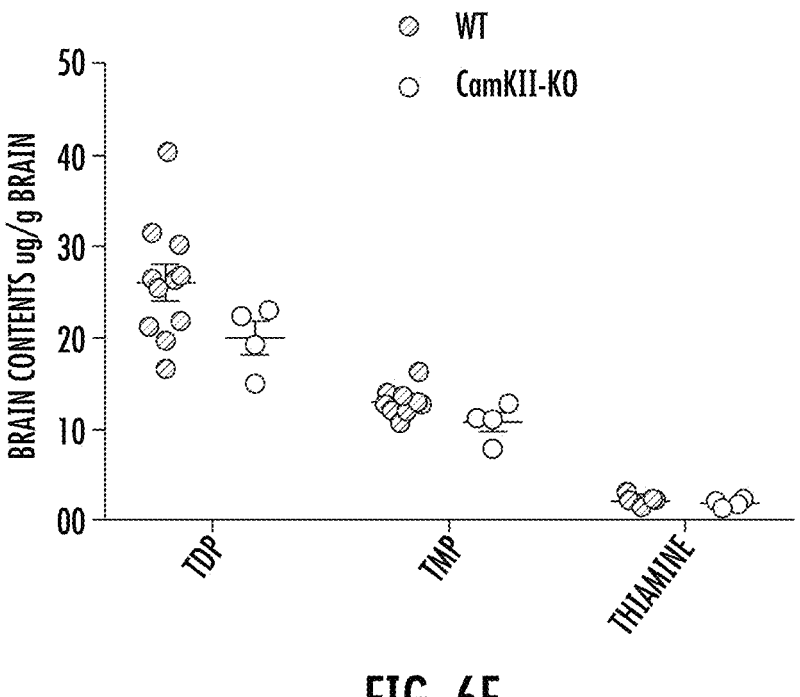
Figure 6F:
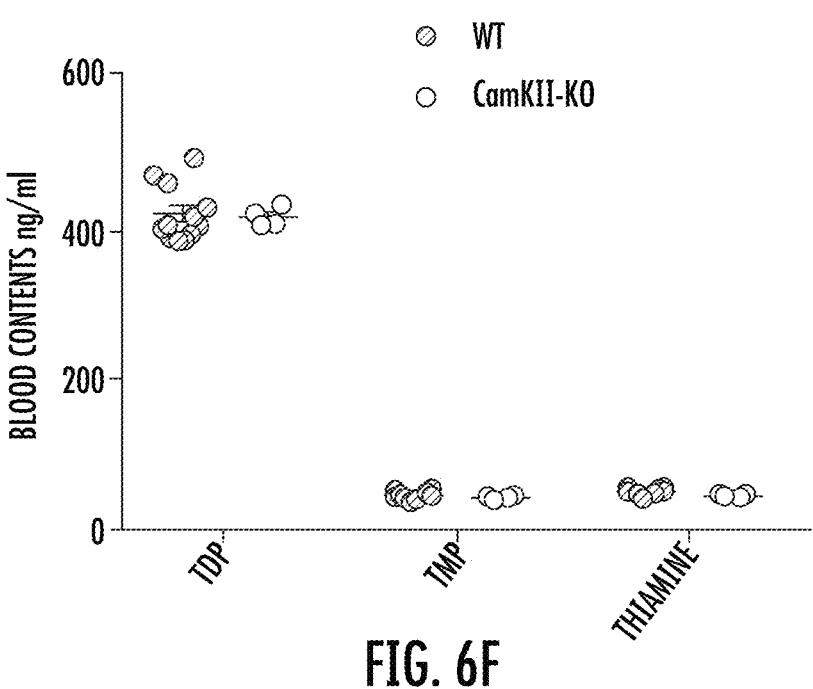
Figure 6G:
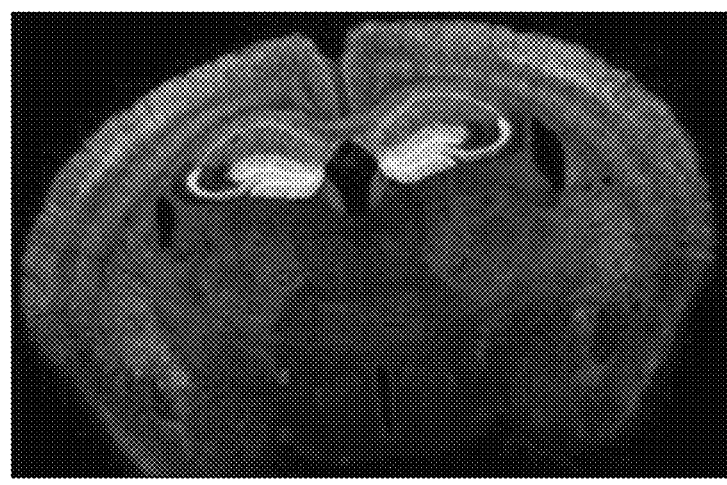
Figure 6H:
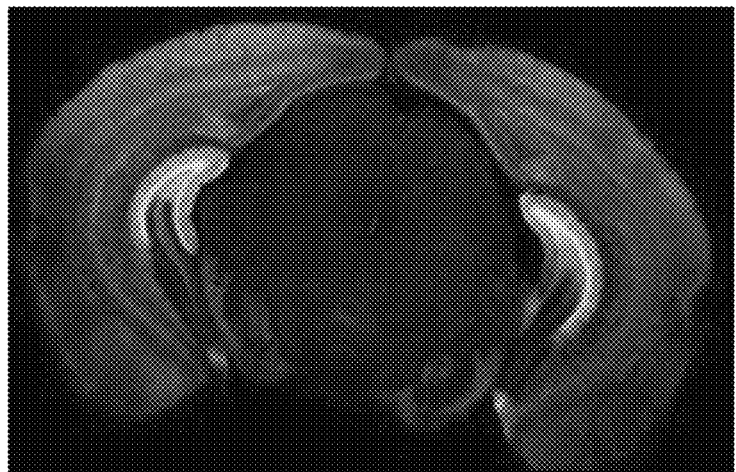
Figure 6I:
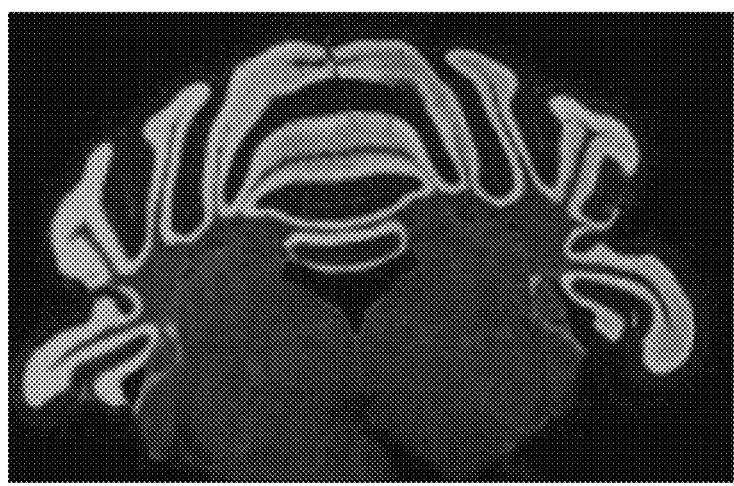
Figure 7A:
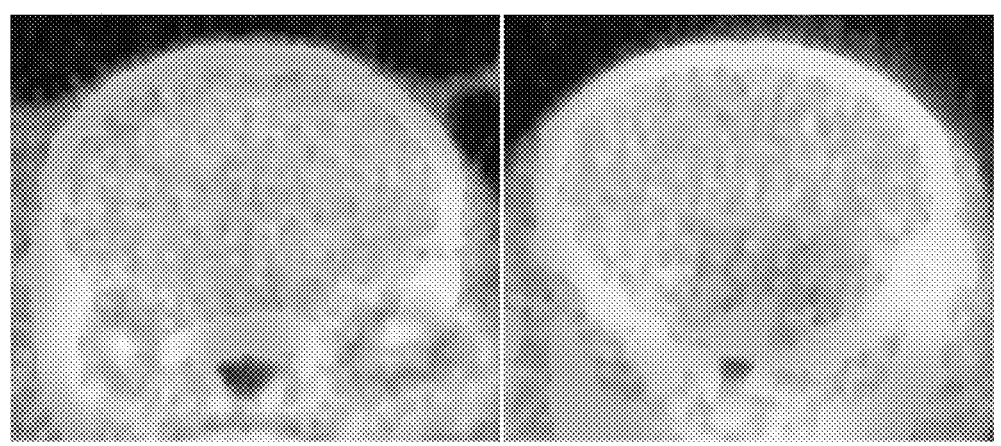
Figure 7B:
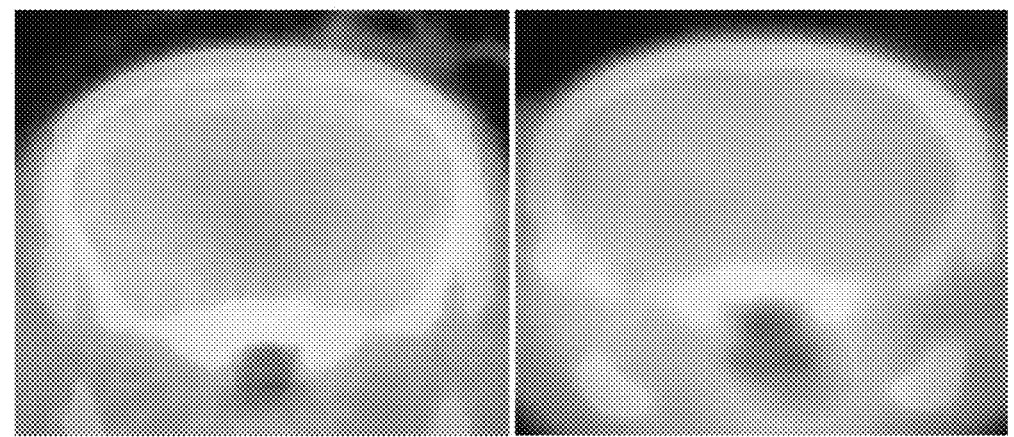
Figure 7C:
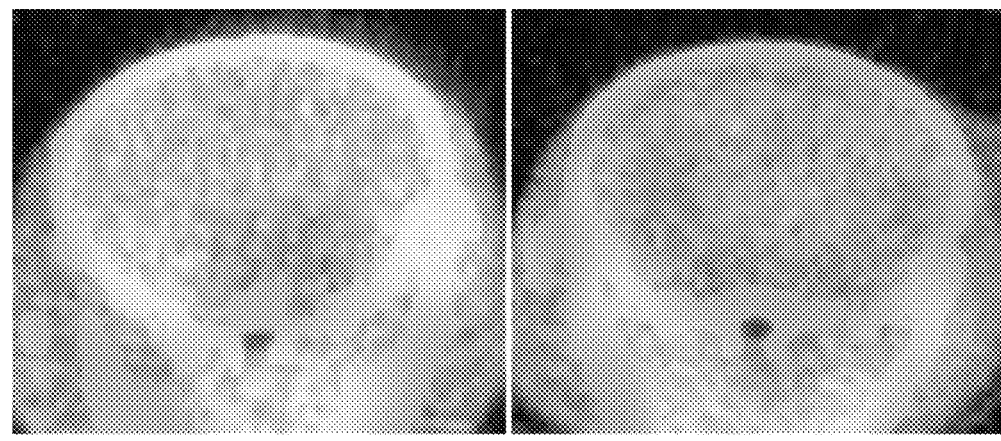
Figure 7D:
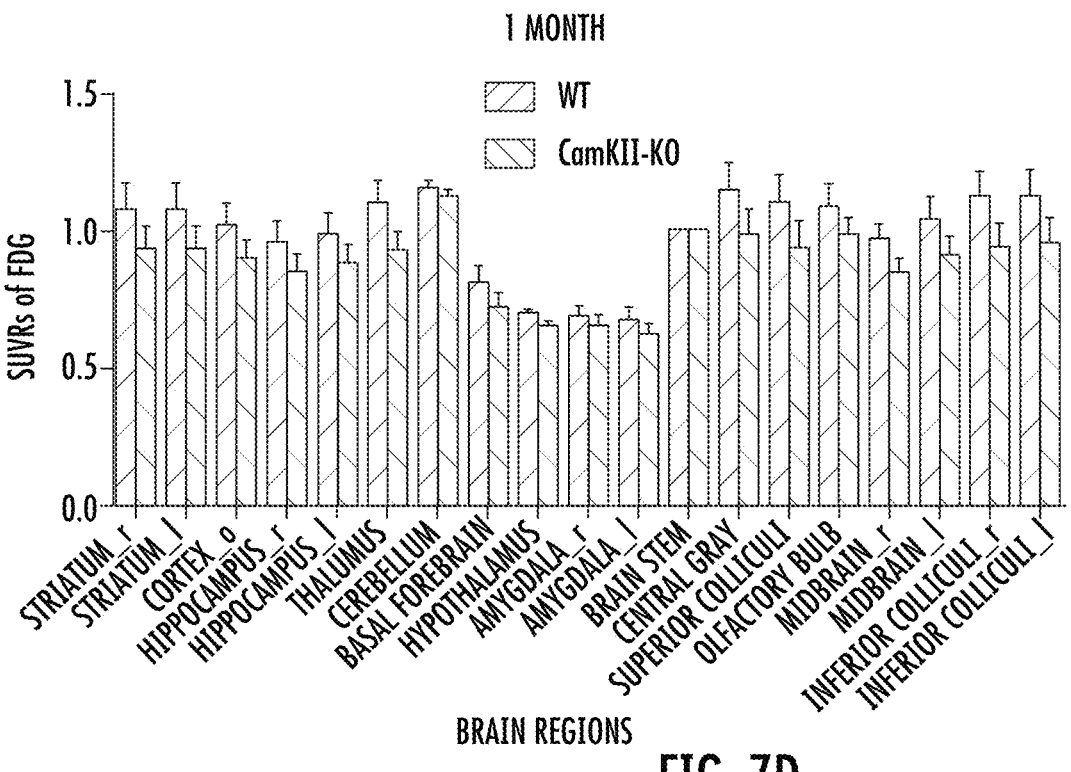
Figure 7E:
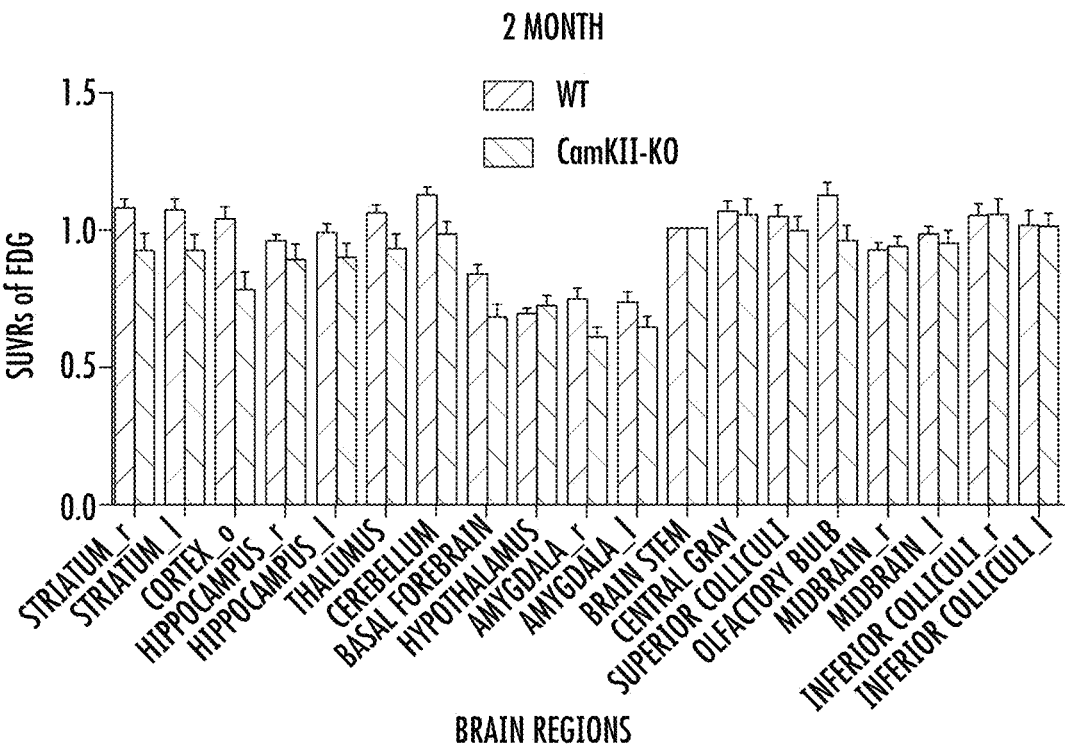
Figure 7F:
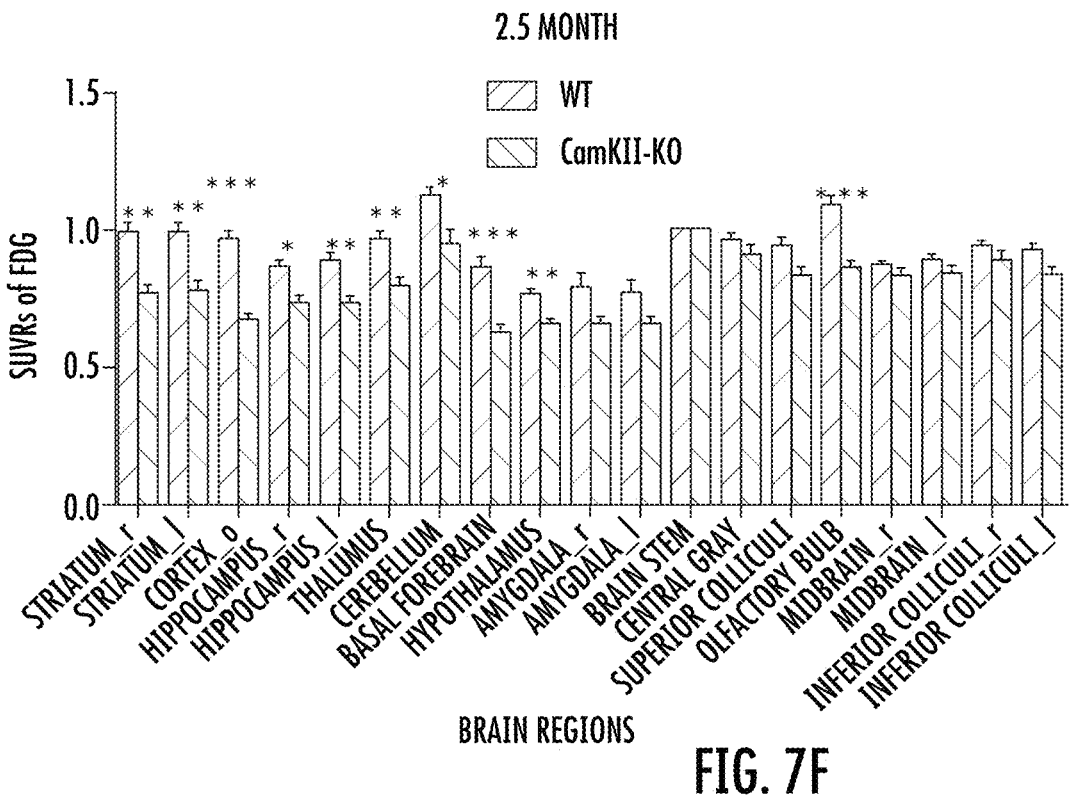
Figure 7G:
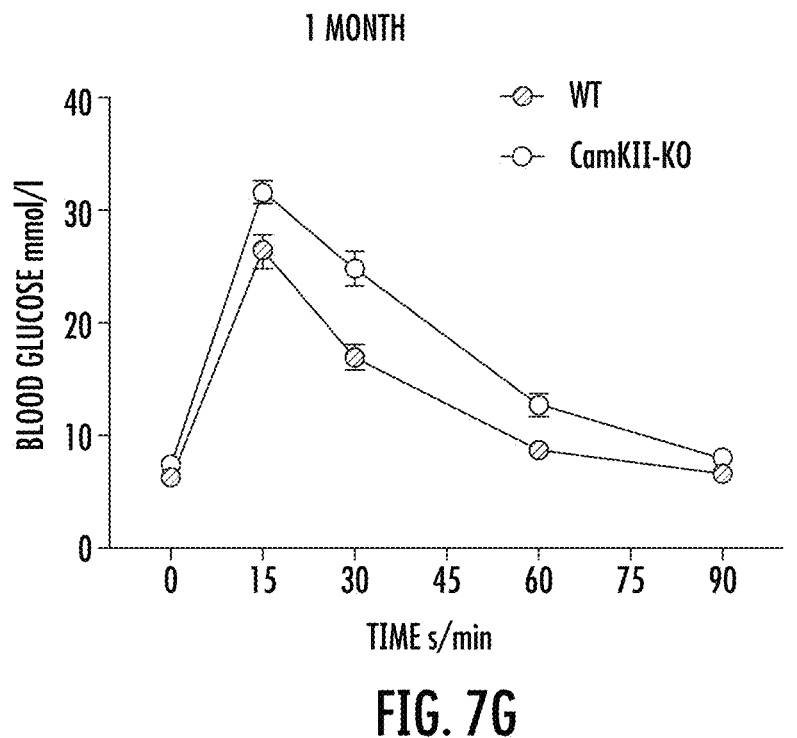
Figure 7H:
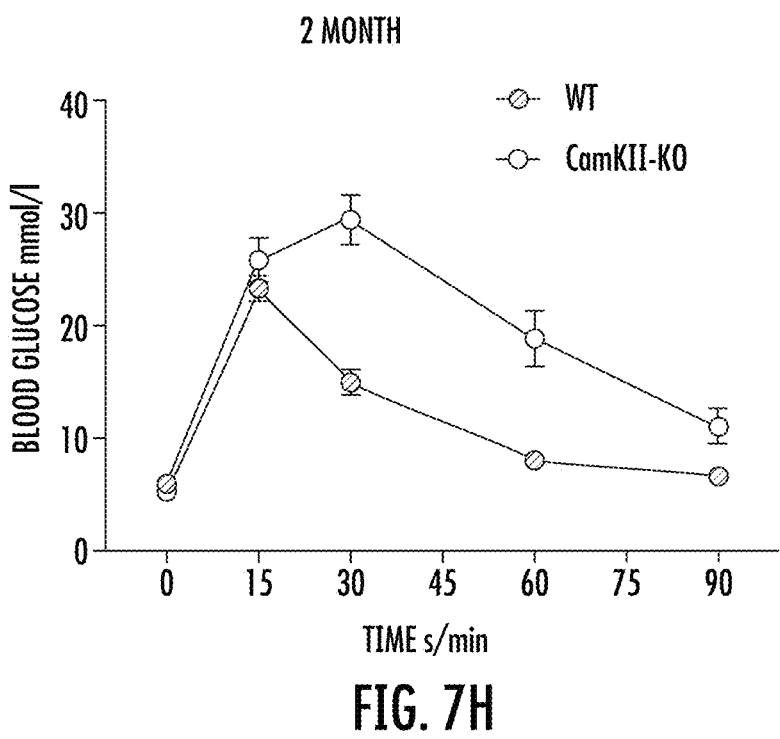
Figure 7I:
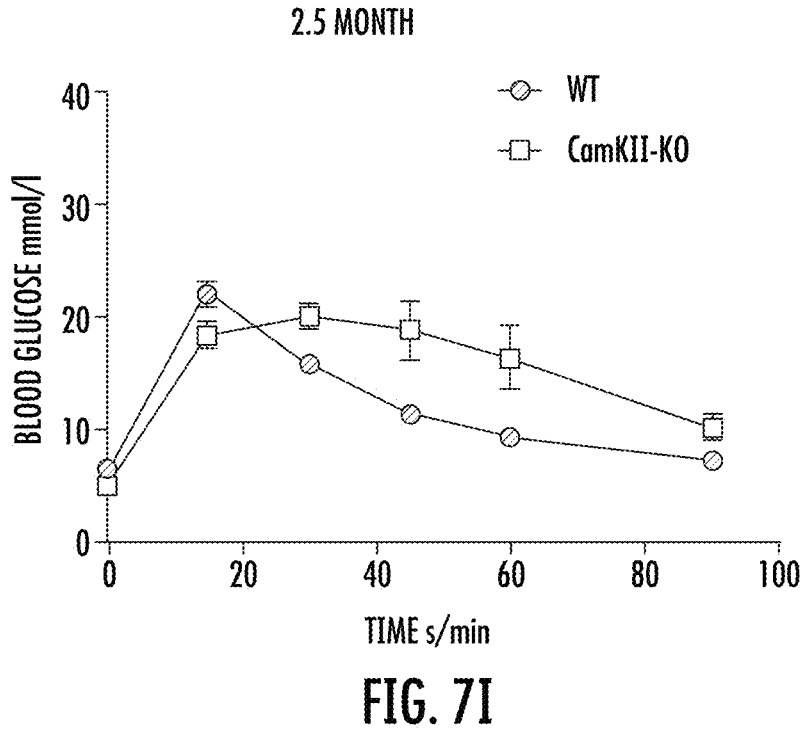
Figure 7J:
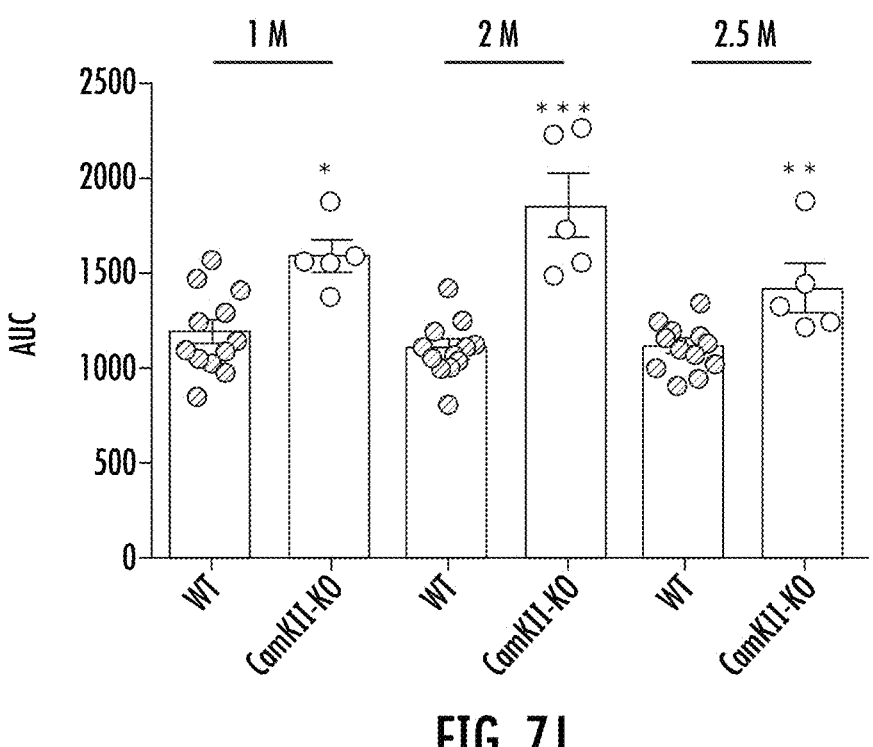
Figure 7K:
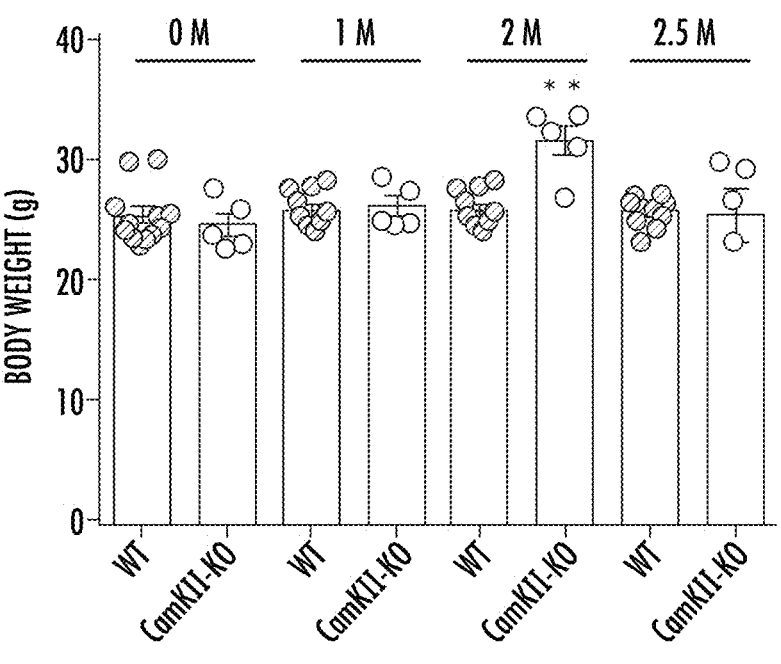
Figure 7L:
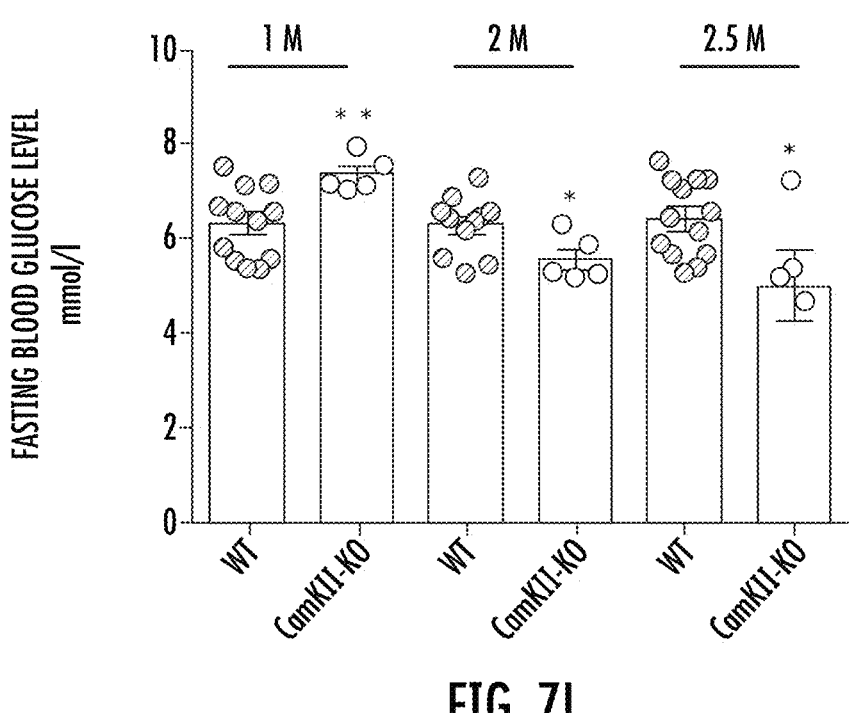
Figure 9A:
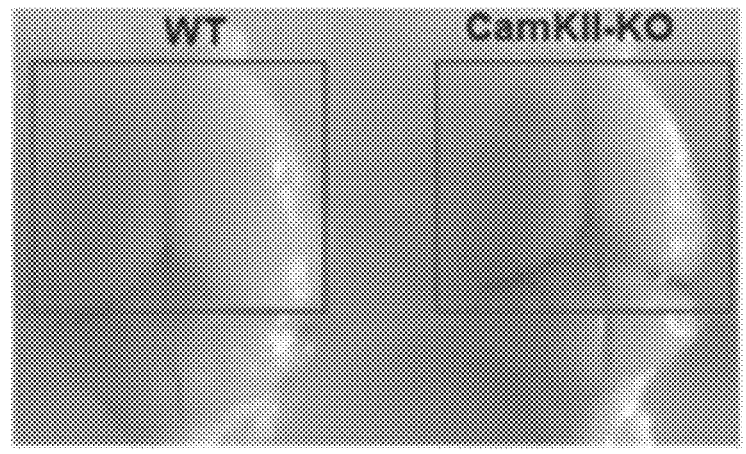
Figure 9B:
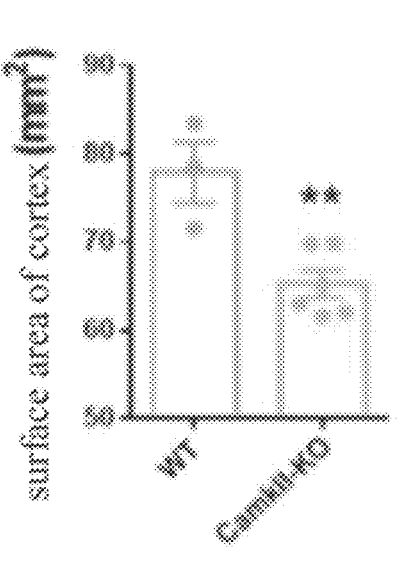
Figure 9C:
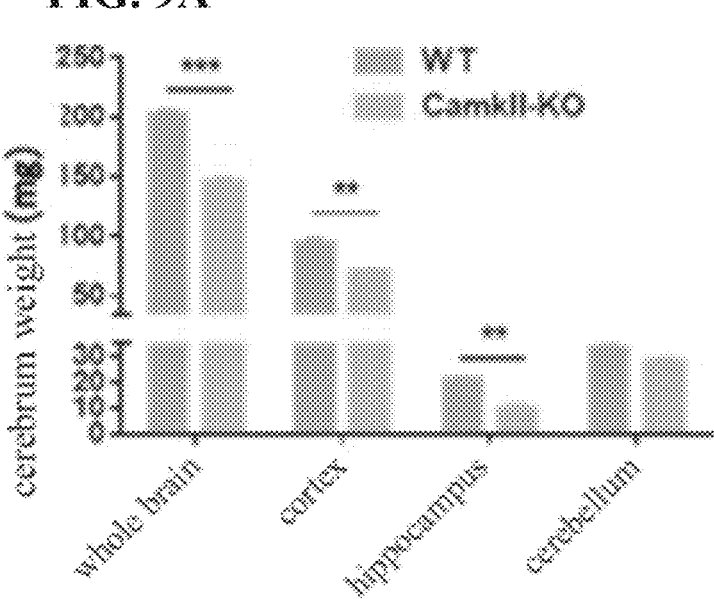
Figure 9D:
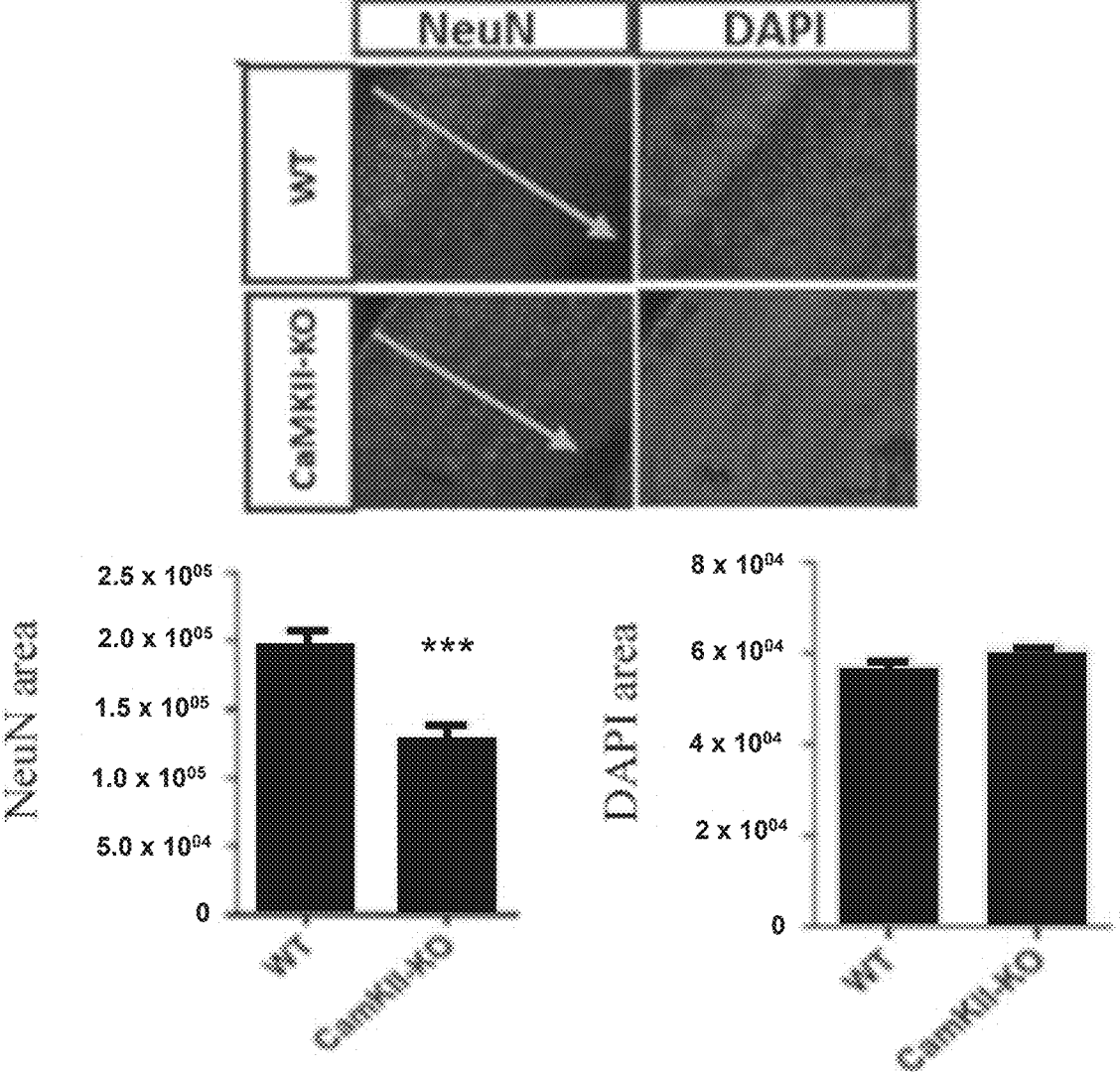
Figure 9E:
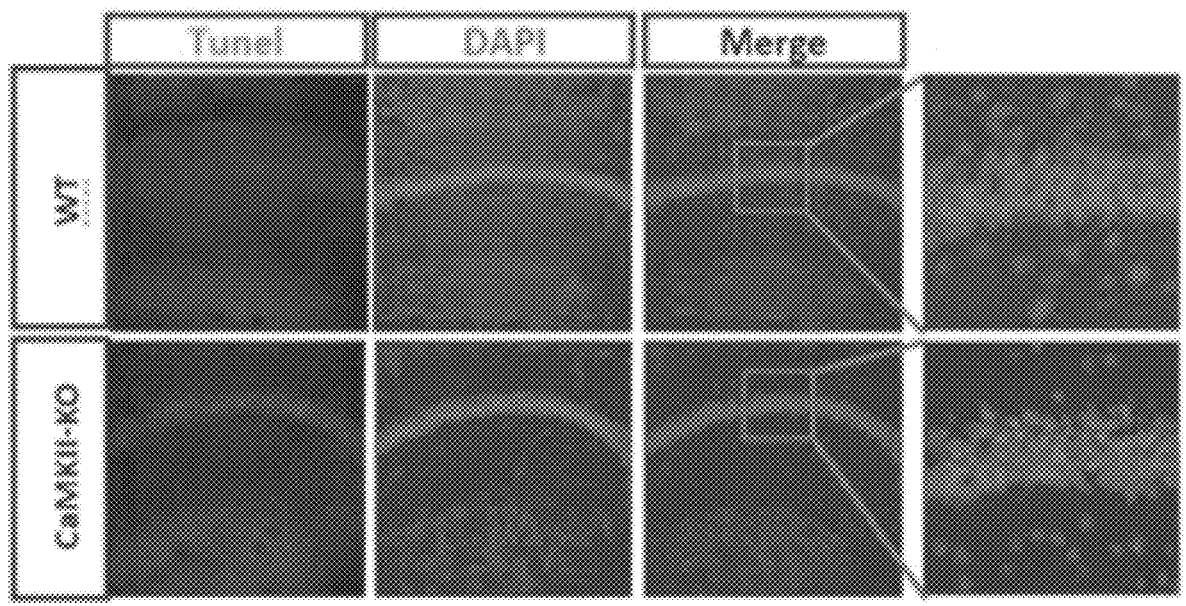
Figure 9F:
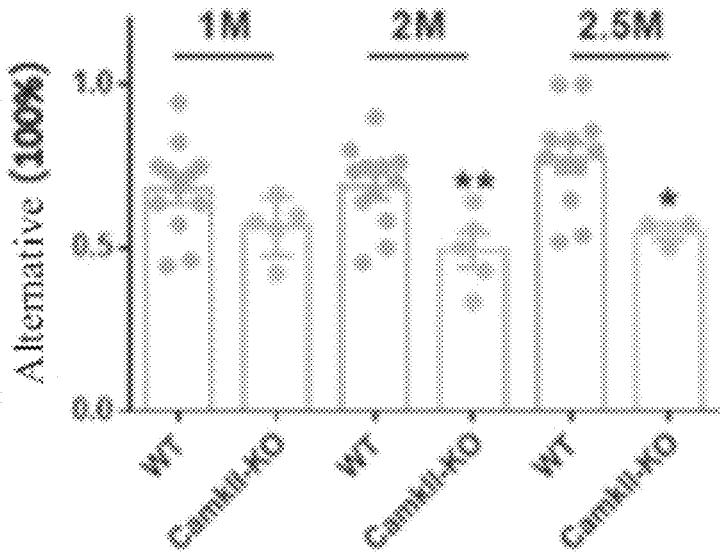
Figure 10A:
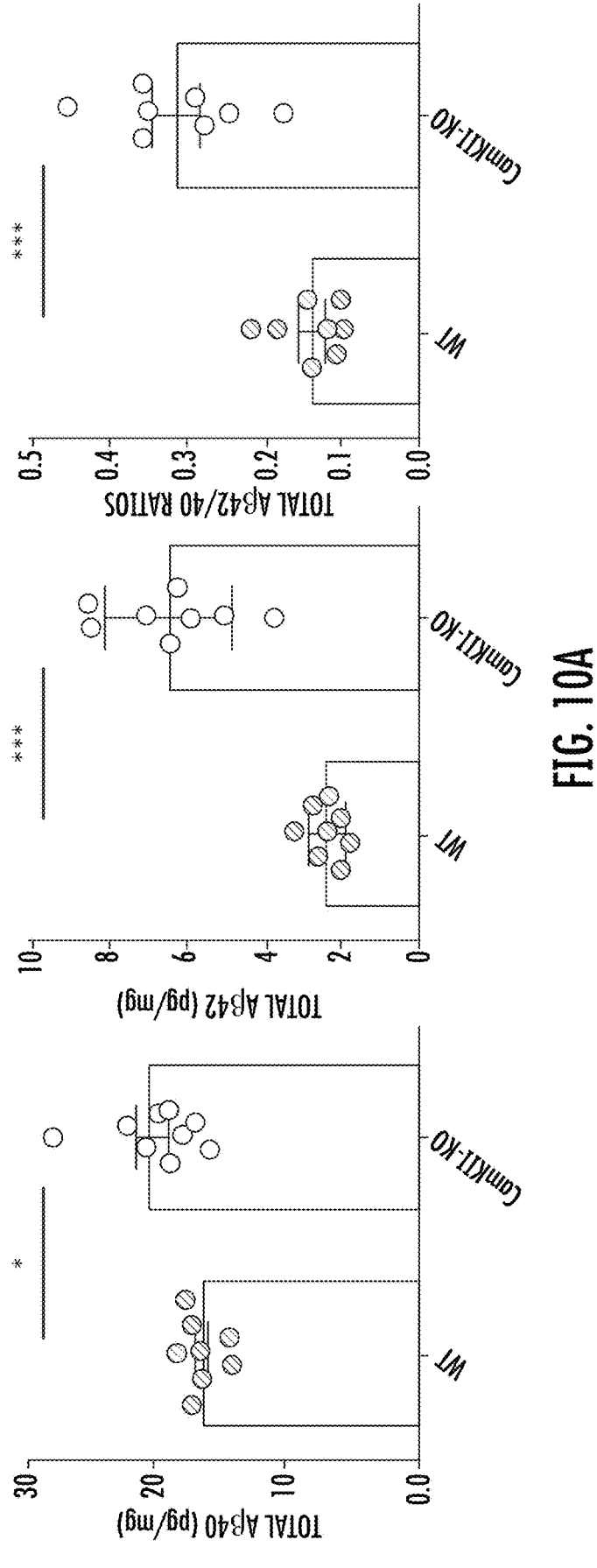
Figure 10B:
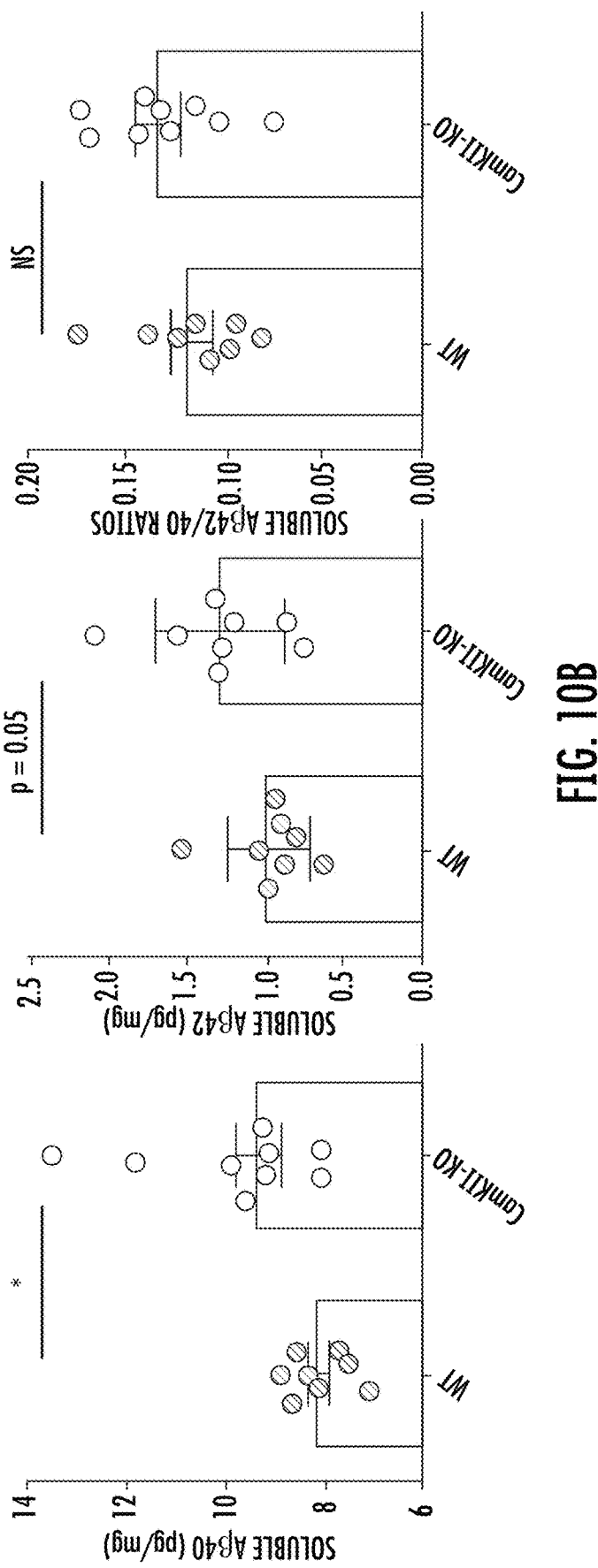
Figure 10C:
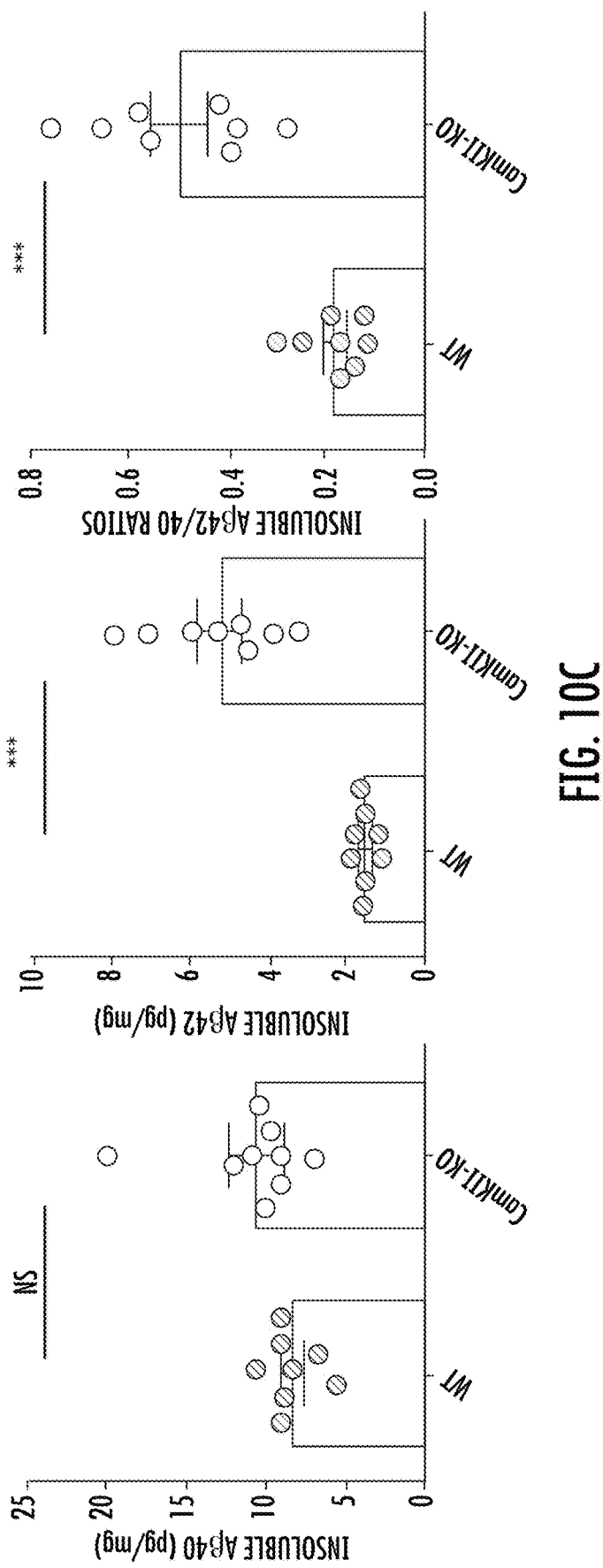
Figure 10E:
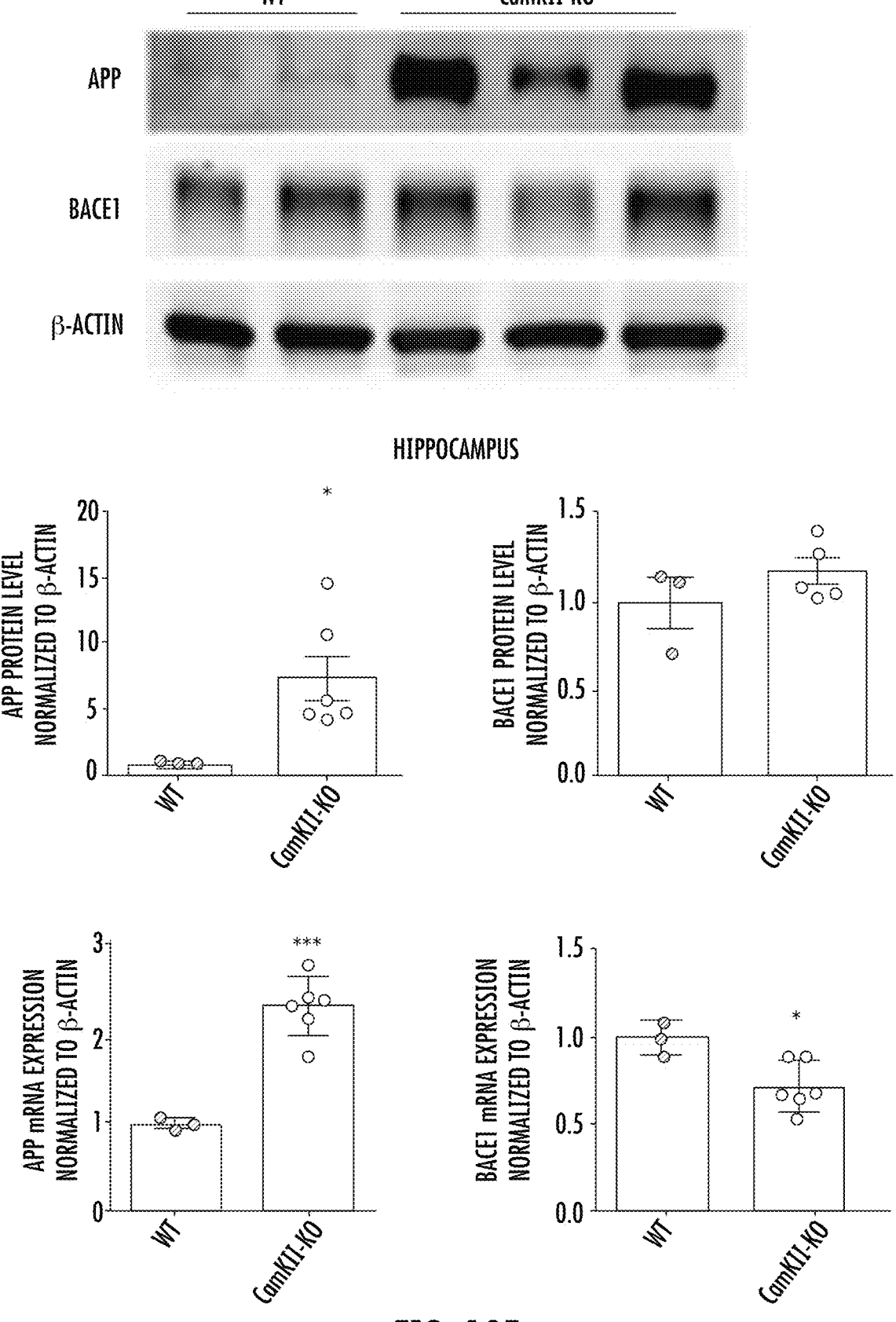
Figure 10F:
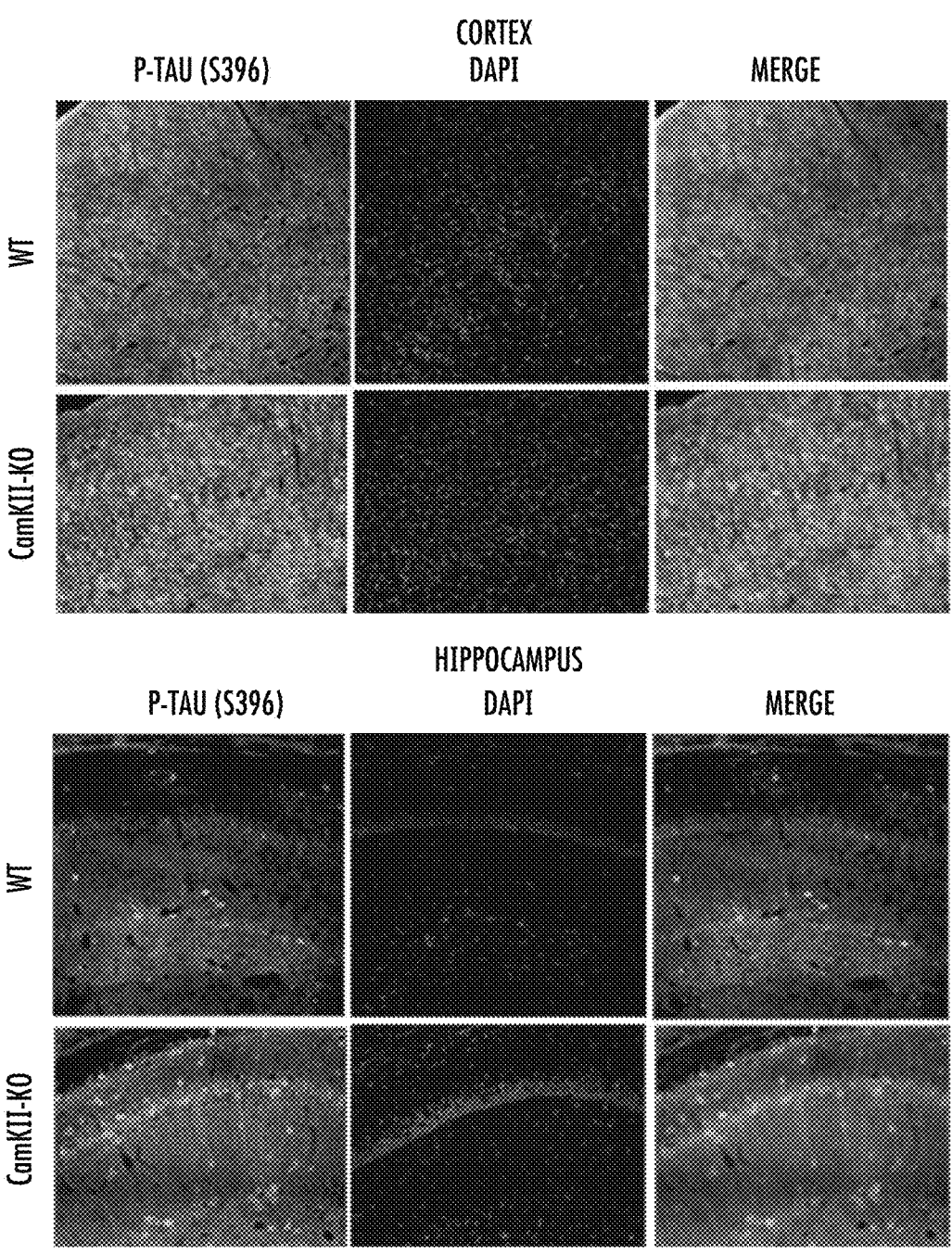
Figure 11A:
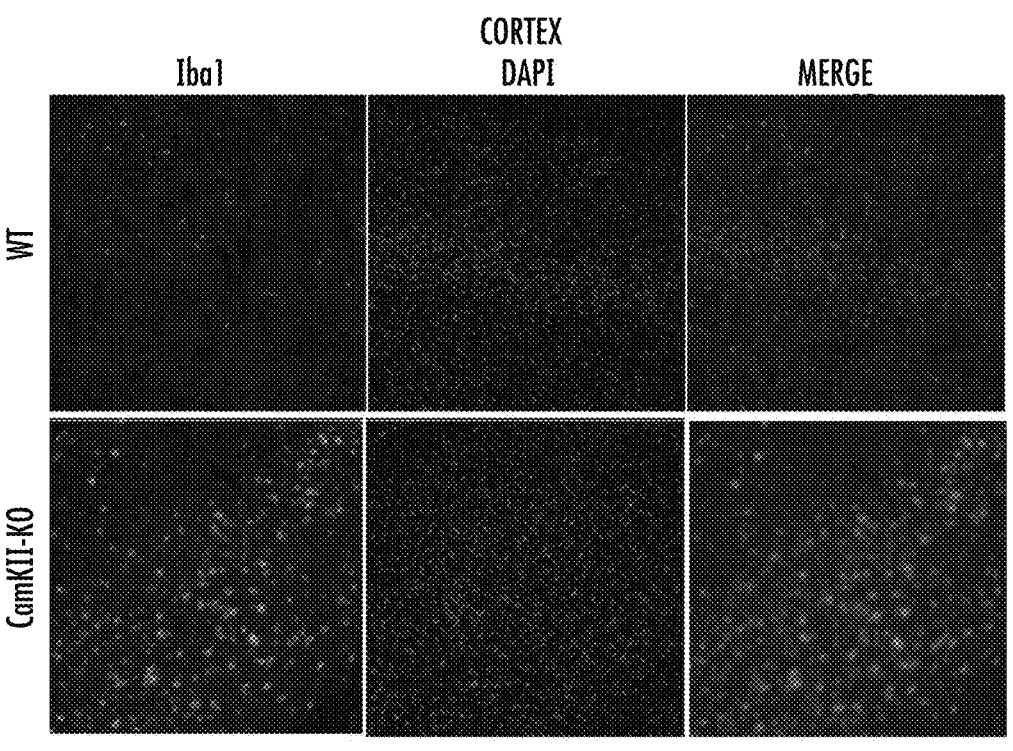
Figure 11B:
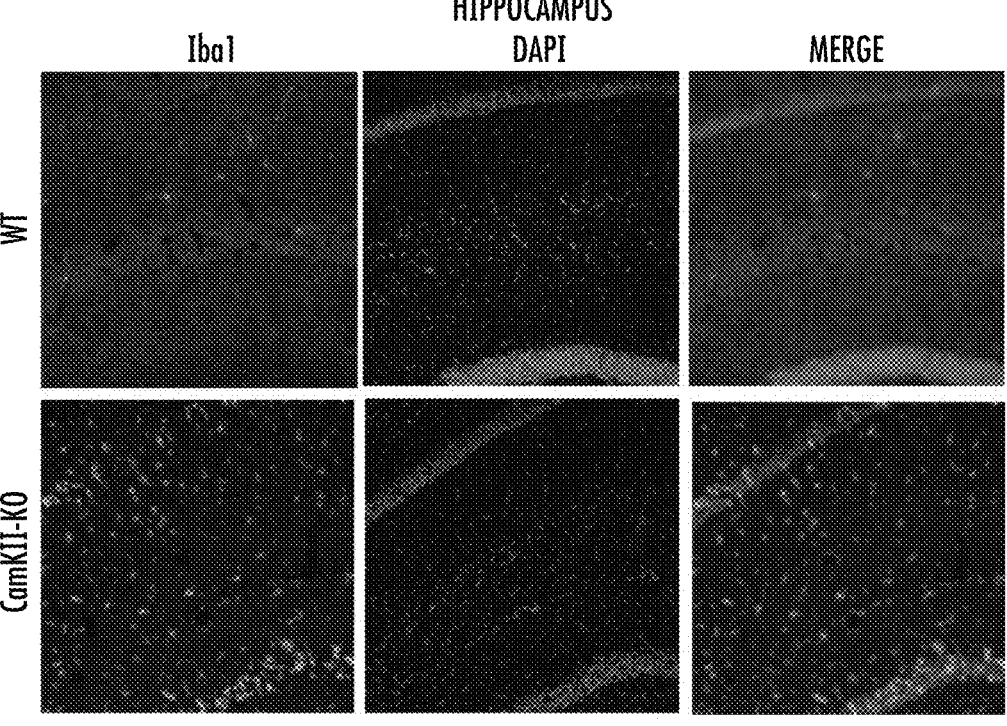
Figure 11C:
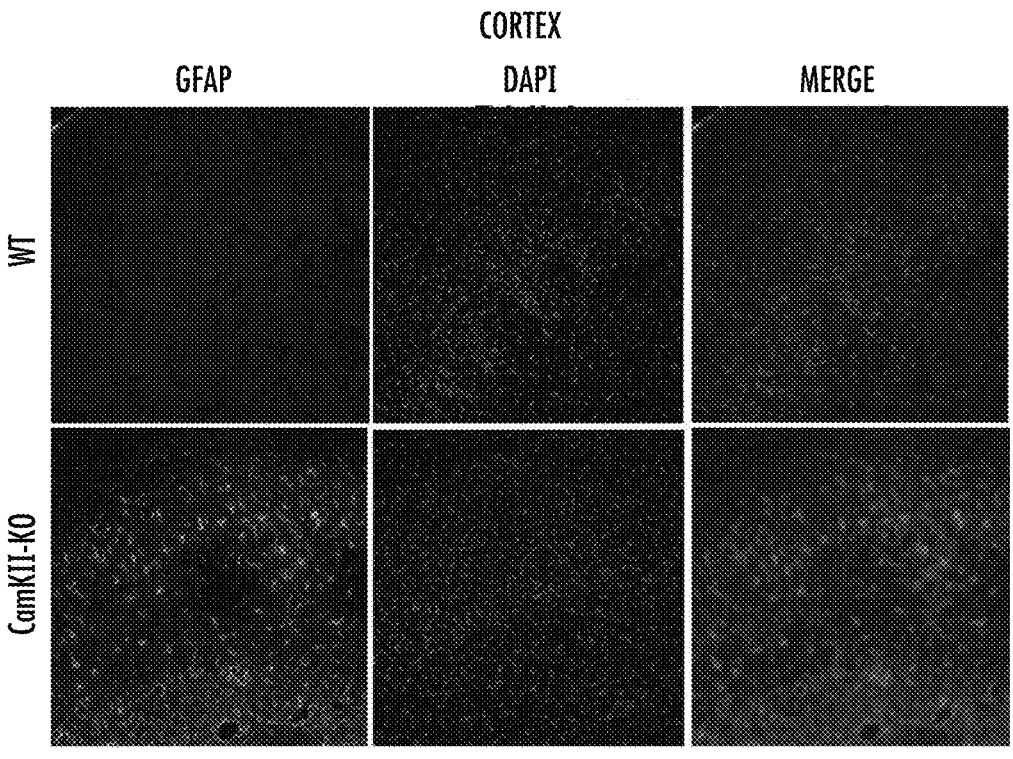
Figure 11D:
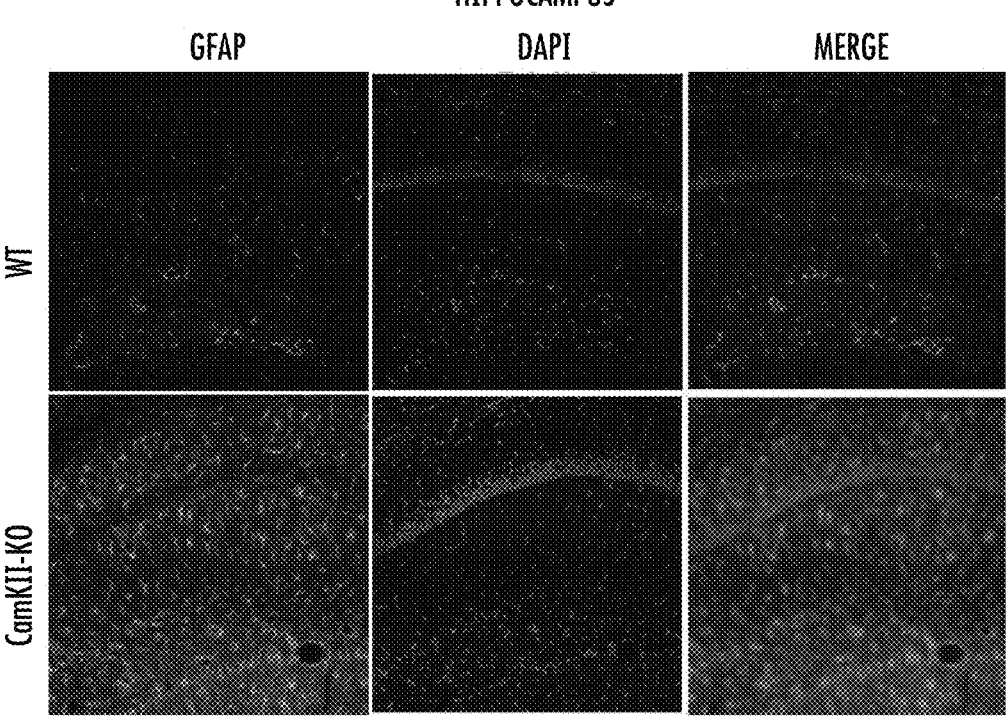
Figure 11E:
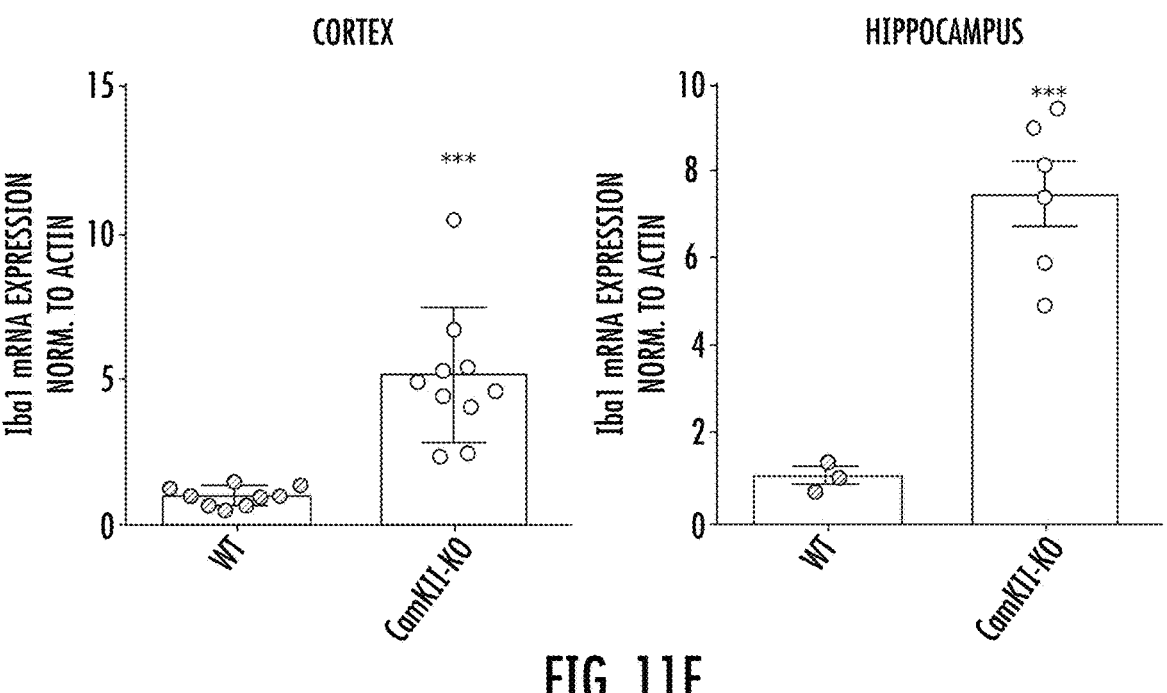
Figure 11F:
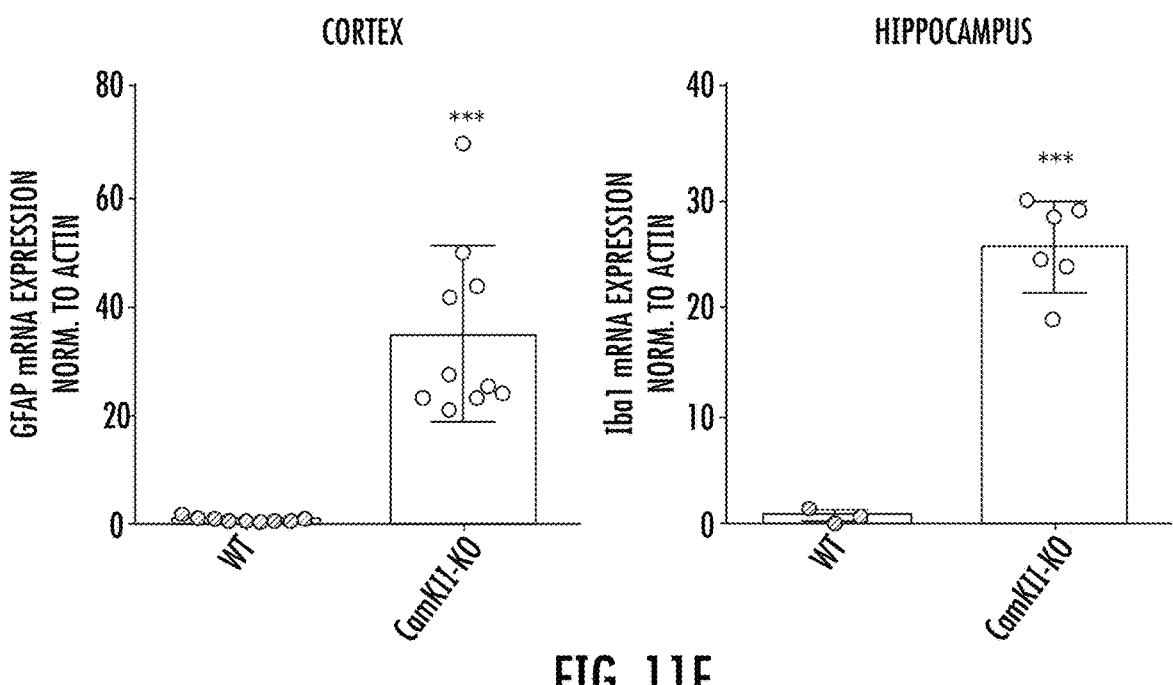
Figure 11G:
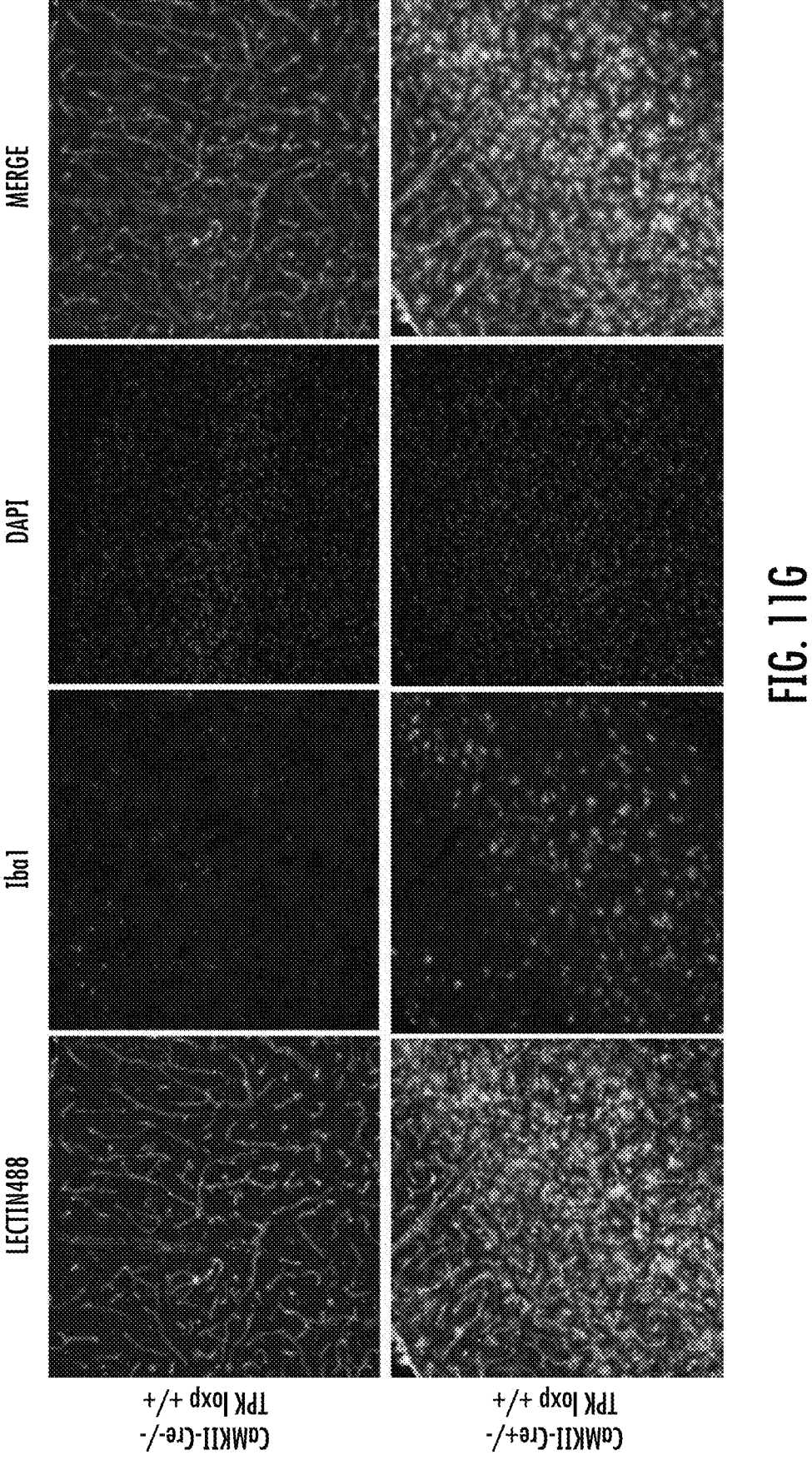
Figure 11H:
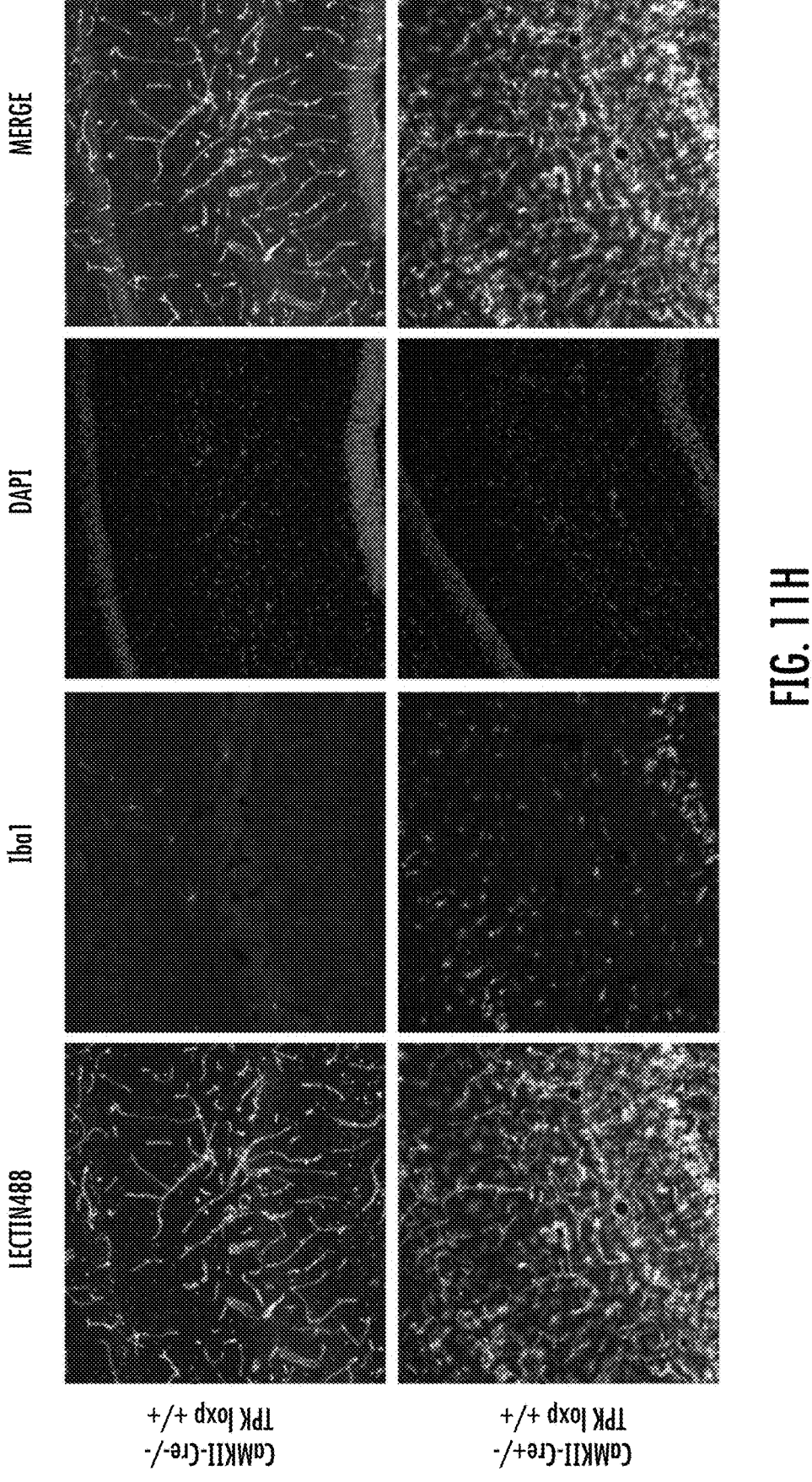
Figure 11I:
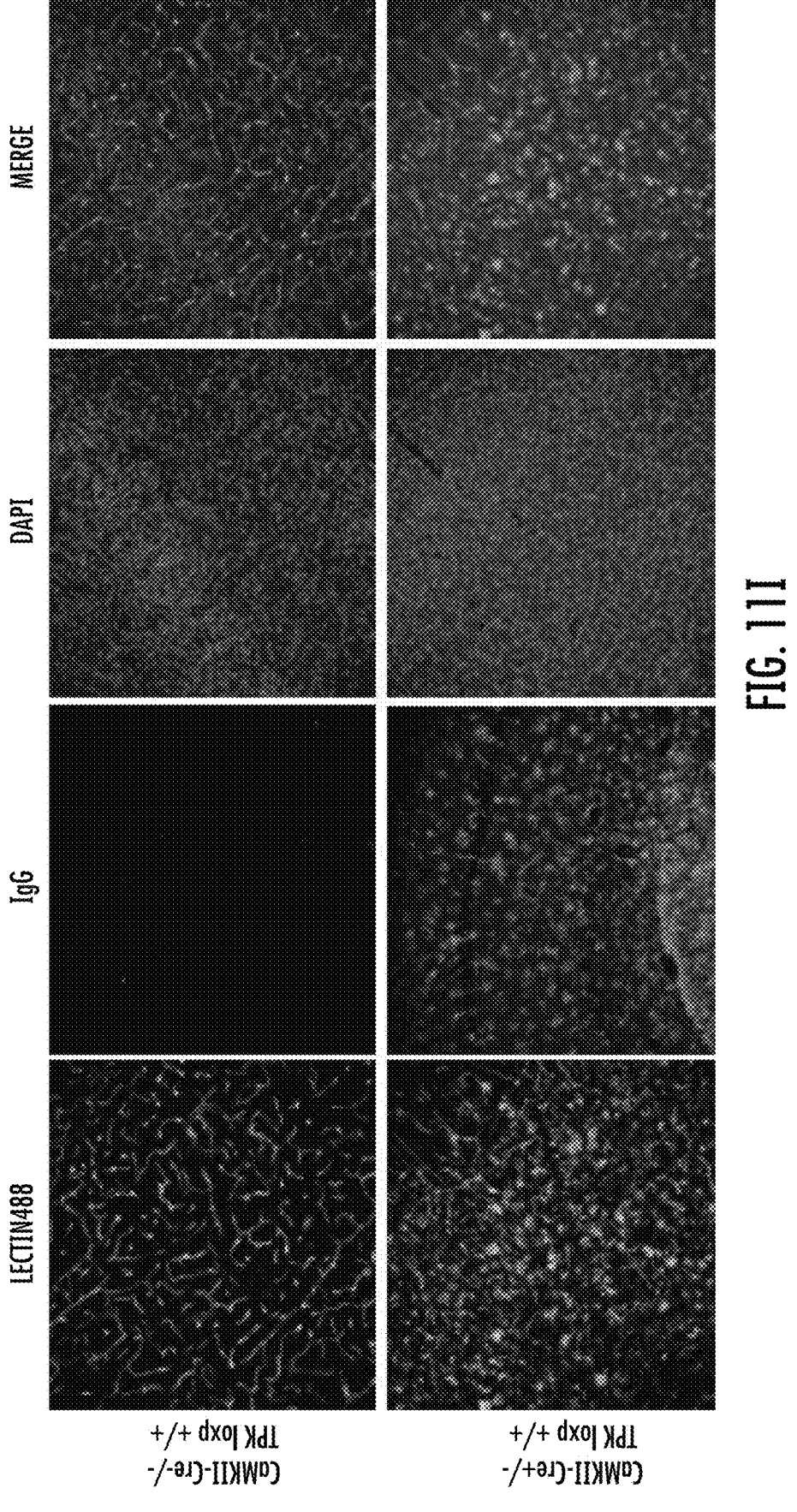
Figure 11J:
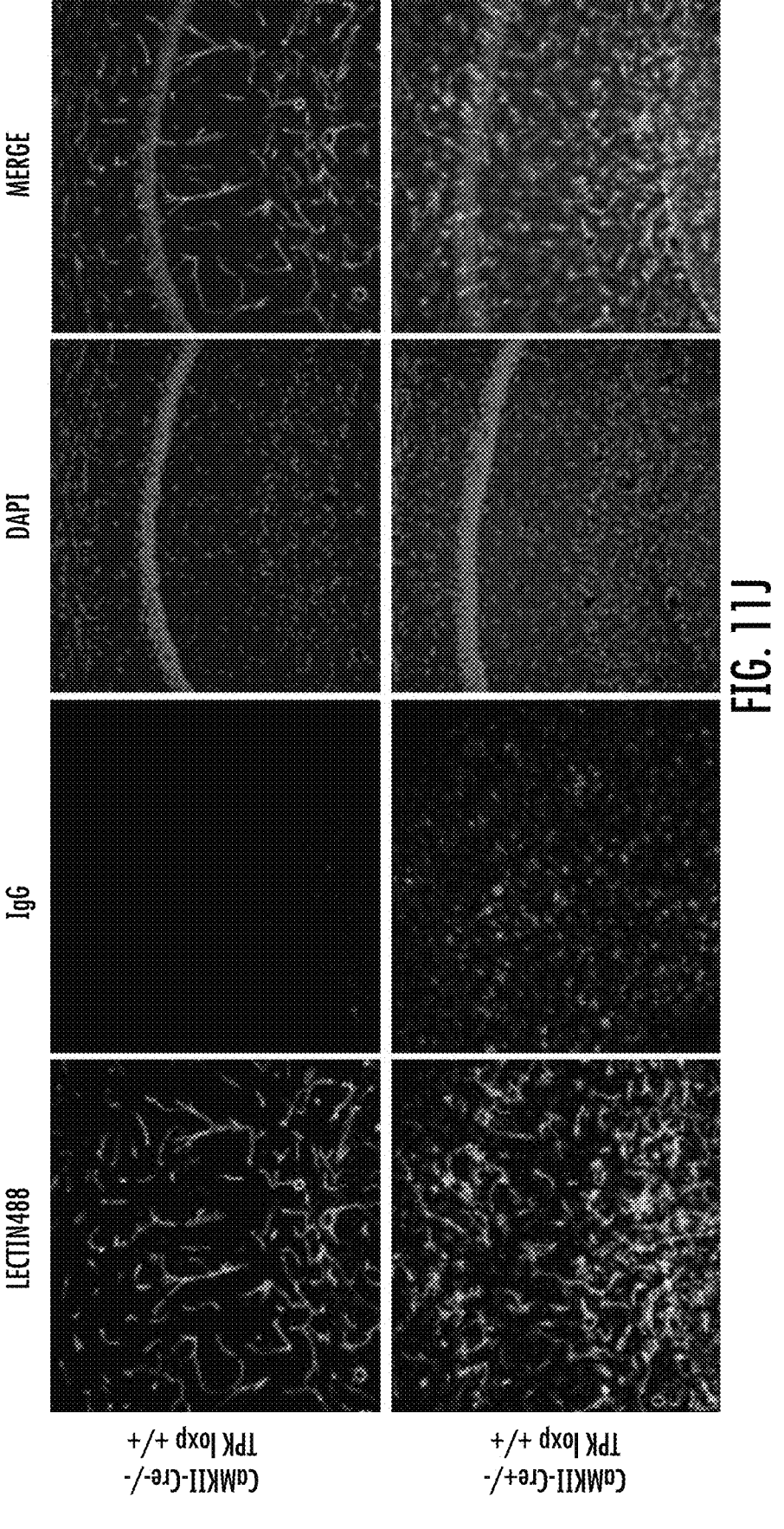

2. Construction of CamK2α-Cre/ERT2+/−; TPK-loxP+/+ Mice (See FIG. 5)

Obtaining and Acreening of TPK-floxP+/− Embryonic Stem Cell (1) Preparation of Mice Embryonic Stem (ES) Cell Primary mouse embryonic fibroblasts, as the trophoblasts, were inoculated into dishes treated with 0.1% gelatin on the day before the ES cells were thawed and cultured in cell culture broth with LIF added at a concentration of 1000 U/mL.

(2) Electro-Transformation of ES Cells (a) ES cells were digested with pancreatin, followed by resuspended in PBS (approximately 2×10⁷/mL), and placed on ice;

(b) linearized targeting vector (45 μg) was mixed with 1 mL cell, and loaded into electroporation tank, and electro-transformed with parameters of 600 V, 25 g, 10 ms;

(c) cells after electro-transformation were inoculated into dishes with trophoblasts of full confluency, and placed in a 37° C. incubator, cell screening broth containing G418 (280 μg/mL) was added for replacement after 24 hours.

(3) Picking up and Amplification of ES Positive Clone

The selection of clones was started several days after culturing, single undifferentiated ES clones were selected under low-magnification microscope and placed in 96-well plate for the following culture; each clone was divided into two, one was cryopreserved, and the other was transferred to 24-well plate for amplification and passaging.

(4) PCR and Southern blot Identifications of Targeted ES Cell

Positive clones resistant to G418 were selected and amplified, and genomic DNA was extracted, enzymatically digested, and analyzed for the bands of electrophoresis with agarose gel. Southern blot was then performed with probes targeting the 5' and 3' ends of Tpk exon 4, identification was conducted according to distinguishing bands between control and targeted ES cell. In which, Primers for PCR identification were:

| Primers | | Sequence(5'-->3') |
|---|---|---|
| TpkloxP | Forward | GTCACTTGAATATACCACAGTTC CCAG (SEQ ID NO: 2) |
| | Reverse | CATATTGGCACACTACCCTGGAT (SEQ ID NO: 3) |
| TpkloxP-1 | Forward | GCTGACCGCTTCCTCGTGCTTTA (SEQ ID NO: 4) |
| | Reverse | GACCACCAAACAGCATACACCAG CT (SEQ ID NO: 5) |

Primers for preparing 5' and 3' probes for Southern blot were:

| Primers | | Sequence(5'-->3') |
|---|---|---|
| 5' probe primer | Forward | ATCTTTCCAGTGTCTCAT TC (SEQ ID NO: 6) |
| | Reverse | TACTTCTTGTTTCGGTCT T (SEQ ID NO: 7) |
| 3' probe primer | Forward | GGATGTTGGCATTGAAGC (SEQ ID NO: 8) |
| | Reverse | GATTTTAGGAGACGAGCA (SEQ ID NO: 9) |

3. Construction of TPK-floxP Chimeric Mouse by Blastocyst Microinjection (1) Preparation of Mouse Blastocyst 4-week old C57BL/6 female mice were selected, and intraperitoneally injected with 10 IU gonadotropin at noon. 10 IU human chorionic gonadotropin was injected 48 hours later, and the female mice were caged together with the male mice. On the morning of the next day, the female mice were checked for vaginal plugs (recorded as 0.5 day), and female mice with vaginal plugs were sacrificed after 3 days, and the uteri were removed and the blastocysts were rinsed out with BMOC-3 broth. The blastocysts were transferred to drops broth dripped on 60 mm dish, which were covered with mineral oil. The microinjection was performed after the blastocoele was expanded.

(2) Blastocyst Microinjection

Holding pipettes and injection pipettes for microinjection were prepared. Fresh broth was added for replacement to the ES cells for injection 3 hours before injection. Single-cell suspension was prepared upon pancreatin digestion. Small and round ES cells with bright surface were selected for injection, each embryo was injected with about 12~15 ES cells, injected blastocysts generally recovered their normal morphology after 1 h culture, blastocysts having intact morphology were selected for transplant.

(3) Blastocyst Transplant

Preparation of pseudopregnant mice: female mice of white Kunming breed were mated with vasoligated male mice, and were checked for vaginal plugs on the next day (recorded as 0.5 day). The pseudopregnant mice can be used for embryo transplantation two days later. The pseudopregnant mice were anesthetized with isoflurane, back surgery was conducted to transfer 10 injected blastocysts into unilateral uterus. If the surgical transplant was successful, neonatal mice may be born 17 days later, it is possible to visually determine, according to hair color several days later, whether TPK-floxP chimeric mice with targeted ES cell integrated were obtained, and the chimeric degree was estimated according to the ratio of brown hair to total hair.

(4) Obtaining of TPK-loxP+/+ Chimeric Mouse

The obtained TPK-floxP chimeric mice were crossed with Flp tool mice, Flp tool enzyme can induce cleavage of Neo sequence at Frt site, and Tpk-loxP+/+ homozygous mice with knockout potential can be obtained upon purification.

(5) Obtaining of CamK2α-Cre/ERT2+/−; Tpk-loxP+/+ Mouse (A) Tpk-loxP+/+ mice obtained by the above-mentioned operation and confirmed can achieve Tpk knockout;

(B) Tpk-loxP+/+ mice were crossed with CamK2α-Cre/ERT2+/− mice to obtain CamK2α-Cre/ERT2+/−; Tpk-loxP+/+ mice, which were genetically identified, and then, bred.

Primers for Identification:

| Primers | | Sequence (5'-->3') |
|---|---|---|
| JD-TPK | Forward | GAA TTC CAA AGC CAG CAT GT (SEQ ID NO: 10) |
| | Reverse | CCA CTC ACA GAC CCT TTG CA (SEQ ID NO: 11) |
| JD-CamK2α | Forward | GAC AGG CAG GCC TTC TCT GAA (SEQ ID NO: 12) |
| | Reverse | CTT CTC CAC ACC AGC TGT GGA (SEQ ID NO: 13) |

(6) Phenotype of Mouse Possessing Conditional TPK Gene Conditional Knockout

TPK gene knockout specifically in cortex and hippocampus was achieved by crossing with CamkII-Cre/ERT2+/− mice, and 3-month-old mice were intraperitoneally injected with Tomaxifen to induce TPK gene knockout. Phenotyping of TPK gene knocked out mice were performed, of which the results were shown in FIGS. 6-11.

By reference to FIG. 6, cerebral TPK protein level and TDP level can be significantly decreased 2.5 months after Tomaxifen inducing TPK gene knockout, without affecting thiamine level. By reference to FIG. 7, FDG-PET was performed 1, 2, 2.5 months after Tomaxifen inducing TPK gene knockout, respectively, it was found by blood glucose assay and glucose tolerance test, that TPK knockout mice exhibited significant cerebral glucose metabolism disorder, peripheral glucose dyshomeostasis, and glucose tolerance disorder. By reference to FIG. 8, metabonomic study demonstrated that TPK gene knockout caused glycolysis and tricarboxylic acid cycle disorder. By reference to FIG. 9, pathological detection demonstrated that TPK gene knockout can significantly cause cerebral atrophy, a great loss of synapses and neurons, increase of Tunel positive cells, chromosome condensation and karyopyknosis. By reference to FIG. 10, pathological studies on Aβ and tau which are essential for AD showed that TPK gene knockout can significantly increase the production of Aβ40 and Aβ42, the increase was mainly achieved by increasing APP expression and Bace1 protein level and increasing Tau protein phosphorylation. By reference to FIG. 11, inflammatory response played an important role in the occurrence and development of AD, and it was also found that there were significant activation of astrocytes and microglial cells and increased expression of inflammatory factor in brain cortex and hippocampus in TPK gene knockout mice; meanwhile, TPK gene knockout led to neurovascular disorder and increased vascular permeability. In conclusion, the knockout of TPK, the key enzyme for brain TDP homeostasis regulation, gene can significantly result in thiamine metabolism disorder, glucose metabolism disorder, and more importantly, can surprisingly induce AD-like neurodegenerative disease, encephalatrophy, pathological changes in Aβ and tau, neuroinflammation and neurovascular disorder.

Example 3

Information of antibodies in this Example was as follows:

| Antibody name | Origin | Company | Catalog# | Dilution |
| --- | --- | --- | --- | --- |
| Purified (Azide-free) anti-β-amyoid H6, clone: 6E10 (Primary antibody) | Mouse | Biolegend | 803003 | 1:2000 |
| GAPDH Antibody (Primary antibody) | Rabbit | Wabways | 1:2000 | 1:3000 |
| HRP labelled goat anti-mouse (Secondary antibody) | Goat & Mouse | Beyotime | A0216 | 1:1000 |
| HRP labelled goat anti-rabbit (Secondary antibody) | Goat & Rabbit | Beyotime | A0208 | 1:1000 |

Information of reagents in this Example was as follows:

| Reagent name | Company | Catalog# | Batch# |
| --- | --- | --- | --- |
| PMSF (100 mM) | Beyotime | ST506 | / |
| SDS-PAGE protein loading buffer (5X) | Beyotime | P0015L | / |
| Prestained protein marker (19-117KD) | Beyotime | P0066 | / |
| PageRuler ™ Prestained Protein Ladder | Thermo | 26616 | 00766861 |
| BCA Protein Concentration Assay Kit (including protein marker) | Beyotime | P0012S | 080719191115 |
| SDS-PAGE gel rapid preparation kit | Beyotime | P0012AC | P0012AC |
| Heat shock bovine seurm/ Albumin powder | Equitech-Bio. Inc | BAH67-0500 | #1367 |
| Western and IP cell lysis buffer | Beyotime | P0013 | 092919200101 |
| DMEM | Gibco | 11965-092 | 1967762 |
| 0.25% Trypsin-EDTA | Gibco | 25200-056 | / |
| Opti-MEM I Reduced Serum Medium, no phenol red | Gibco | 11058-021 | 1967656 |
| Lipofextamine2000 | Invitrogen | 11668-019 | 2001808 |
| FBS | Gibco | 10099-141 | 1932595 |
| ECL Western Blotting Substrat | Pierce | 32109 | UA277602 |

1. Construction of TPK Overexpression Plasmid

Figure 12:
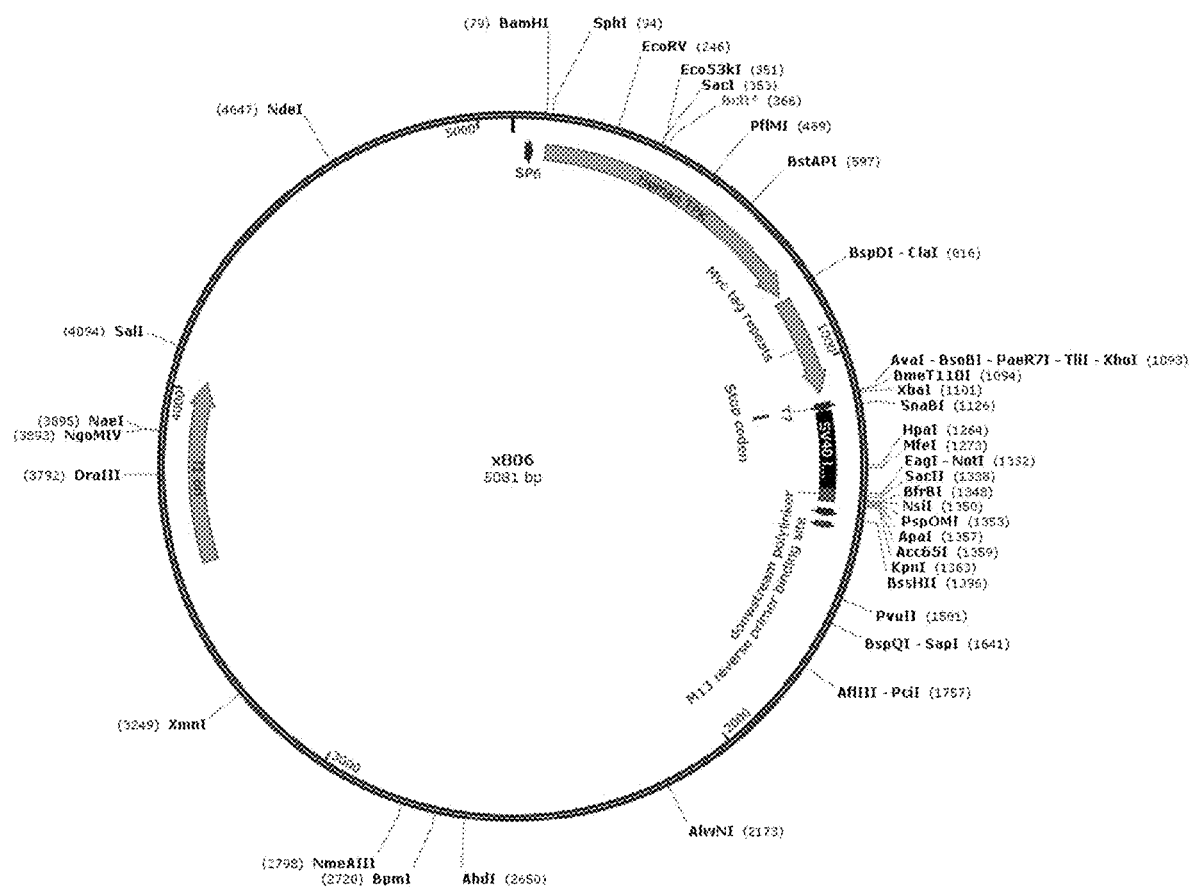
FIG. 12 shows the TPK overexpression plasmid in Example 3.

Human TPK sequence was amplified by PCR from cDNA produced by reverse transcription from HEK 293 cells of human origin, and the product of PCR amplification was digested with restriction endonucleases (5': BamHI-HF (Buffer 4), 3': ClaI (Buffer 4+BSA)), and the target gene sequence fragment TPK1 of 732 bp (NM_022445)(SEQ ID NO: 14). Eight repeats of Myc tag were inserted to the C terminal of the coding sequence to generate TPK1-Myc, the target fragment was cloned into pCS2 vector, and thus, TPK overexpression plasmid was constructed (see FIG. 12).

Primers for PCR Amplification:

```
Forward primer:
                                  (SEQ ID NO: 15)
AT-GGATCC(BamHI)-ACCATGGAGCATGCCTTTACCCCG;

Reverse primer:
                                  (SEQ ID NO: 16)
AT-ATCGAT(ClaI)-GGCTTTTGATGGCCATGGTCCA.
```

2. HEK293-APP Cell and Culture

1) HEK293-APP cells were cultured in 10 cm dishes, and the medium in the dish was removed until at least 90% confluency of adherent cells. The adherent cells were gently washed with 1 mL 37° C. preheated 1×PBS buffer, followed by removing the PBS, and then, 1 mL 37° C. preheated Trypsin-EDTA with a mass-volume percentage concentration of 0.25% was added to the dish, which were then gently shaken, to fully contact the digestive solution with the adherent cells. HEK293-APP cells were placed at room temperature, only about 2-4 minutes were needed for the digestion.

2) 4 mL 37° C. preheated DMEM medium containing 10% FBS (volume percent concentration) was added to terminate the digestion, followed by gently pipetting up and down. HEK293-APP cell suspension was collected, and centrifuged at 1000 rpm for 5 minutes.

3) Supernatant was discarded, and the of HEK293-APP cells were gently pipetted up and down for dispersion with a 1 ml tip, respectively.

4) According to experimental requirements, HEK293-APP cells from 3) were inoculated into 12-well plates at 150,000 cells/well, after 2-day culture, cells adherently grow to 75-85% confluency, and then, the following liposome transfection experiment was performed.

3. Liposome Transfection Experiment

1) The plasmid was removed from –20° C., dissolved at normal temperature, and centrifuged at 13,000 rpm, room temperature for 3 minutes.

2) Formulating plasmid solution: X806 (TPK overexpression plasmid (1.218 µg/µl)) and Ctrl plasmid (empty control plasmid (1.21 µg/µl)) were premixed with opti-MEM medium, respectively, at a mass-volume ratio of 1:50.

3) Formulating liposome solution: Lipofectamine 2000 was mixed with opti-MEM medium according to 1:50 mass volume ratio.

4) Equal volumes of plasmid solution and liposome solution were mixed, and placed at room temperature for 20 minutes to form the complex of the plasmid and liposome. The mixture was stable in 6 hours.

5) The mixture was added to a 12-well cell culture plate, 150 µl per well in total. The mixture was pipetted up and down or the plate was shaken back and forth, to avoid accumulation.

6) HEK293-APP cells with plasmid-liposome mixture added were placed in carbon dioxide incubator for 24 hours and 48 hour, followed by the collection, treatment and test of protein samples from the cells.

4. Collection and Treatment of Protein Samples of HEK293-APP Cells

HEK293-APP cells transfected with liposome were cultured for 24 hours and 8 hours, followed by washing the cells for 3 times with 37° C. preheated 1×PBS. The PBS was discarded, and 100 µl RIPA lysis solution (containing protease inhibitor PMSF) was added to each well of the 12-well cell culture plate. The RIPA lysis solution was fully contacted with the cells, followed by placing on ice for 5 min.

The cells were scraped with a cell scraper or a tip, and then, collected in tube, which was centrifuged at 4° C., 13,000 rpm for 15 min. The precipitate was discarded, the protein supernatant was collected, the protein concentration thereof was determined with BCA kit, and then, the expression of target protein was detected by Western blot.

5. Western Blot Detection

Overexpression of TPK plasmid in HEK293-APP cell line for 24 hours (TPK OVER-1) and 48 hours (TPK OVER-1) was detected by WB. The particular method for detection was as follows.

1) Preparing gel: the top gel (mass-volume percentage concentration was 5%); the lower gel (mass-volume percentage concentration was 10%).

2) Electrophoresis: 1× running buffer, running at 90 V for 20-30 min, and then, running at 120 V for 60-90 minutes.

3) Membrane transfer: PVDF membrane was placed in methanol for activation, followed by transferring protein from the polyacrylamide gel to the solid support, PVDF membrane, at constant current of 400 mA for 100 minutes.

4) Antibody reaction: the PVDF was blocked with 5% BSA (mass-volume percentage concentration in TBST) for 2 hours, and primary antibody was added, followed by placing at 4° C. overnight. After 3 washes with 1×TBST for 10 min, the PVDF membrane was incubated with the secondary antibody which is diluted with 5% BSA (in TBST) for 2 hours at room temperature, followed by 3 washes with 1×TBST for 10 minutes.

5) ECL developing solution: the development was carried out with CLiNX luminescence instrument (CLiNX, Chemiscopeseries 6000).

Figure 13:
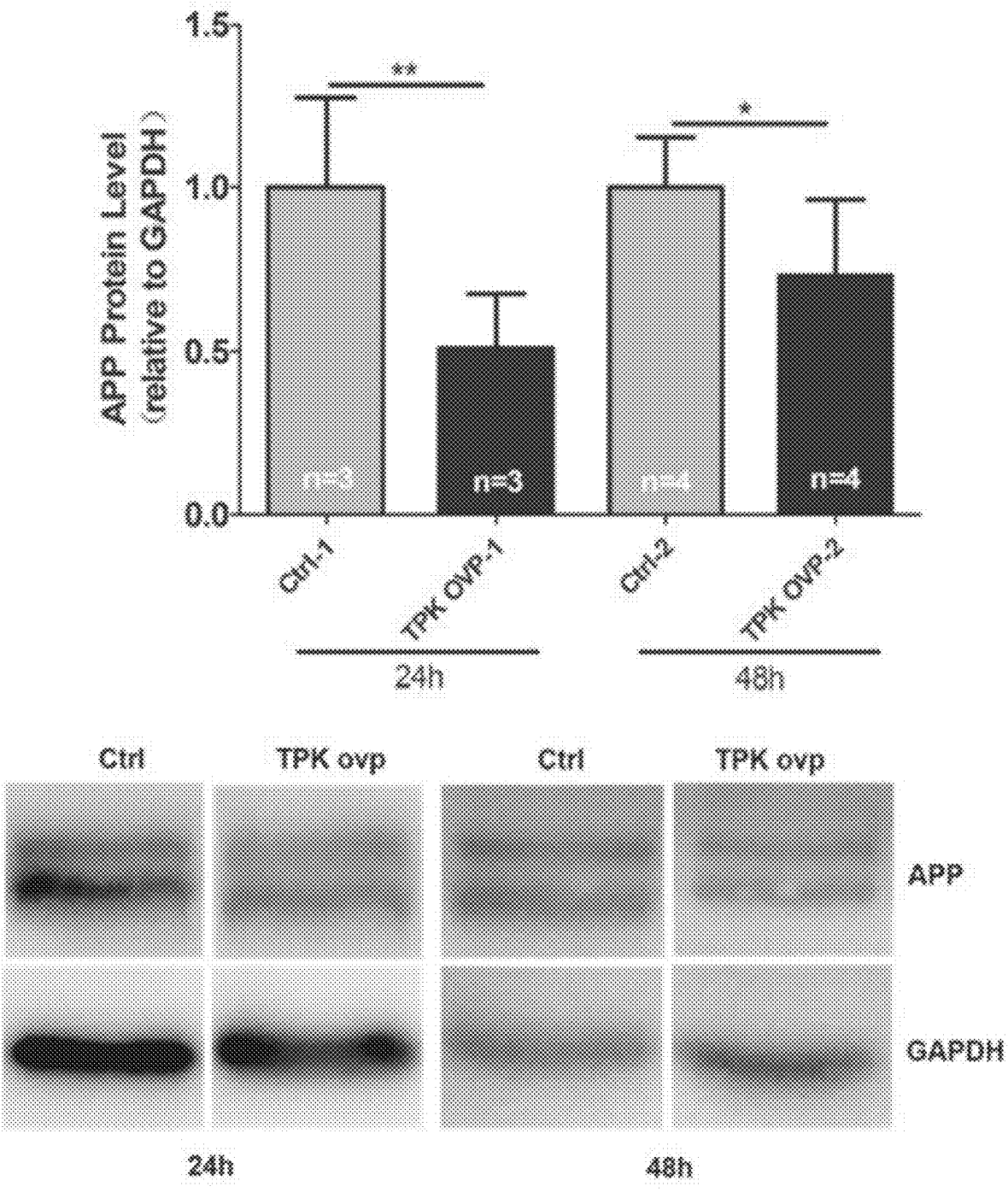
FIG. 13 shows WB detection results of TPK overexpression plasmid and control group thereof on HEK293-APP cell line after 24 hours and 48 hours in Example 3.
Figure 14A:
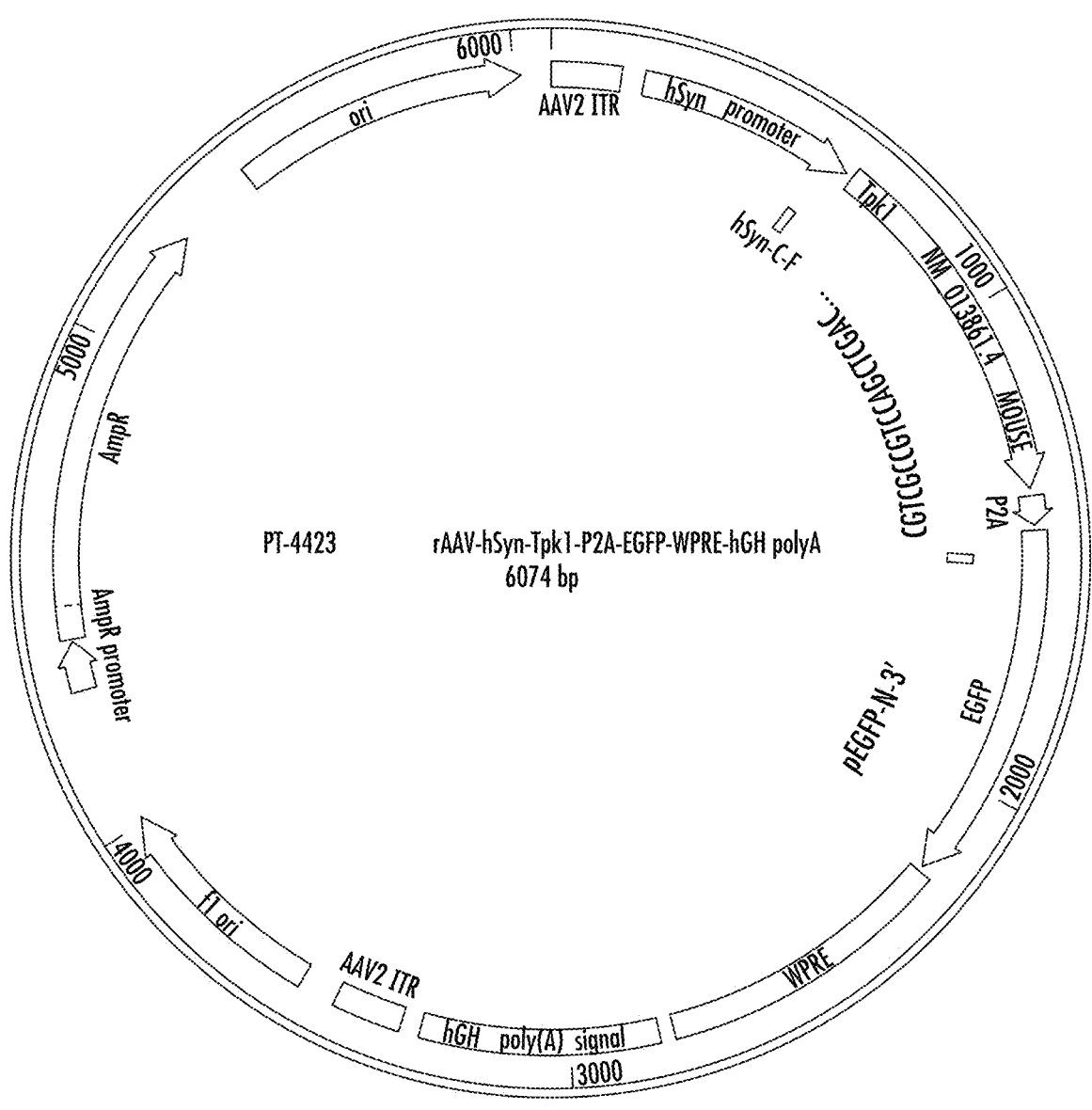
FIGS. 14A and 14B show the map of the plasmid containing the genome of AAV-TPK (FIG. 14A) and the map of the plasmid containing the genome of TPK Lentivirus (FIG. 14B).
Figure 14B:
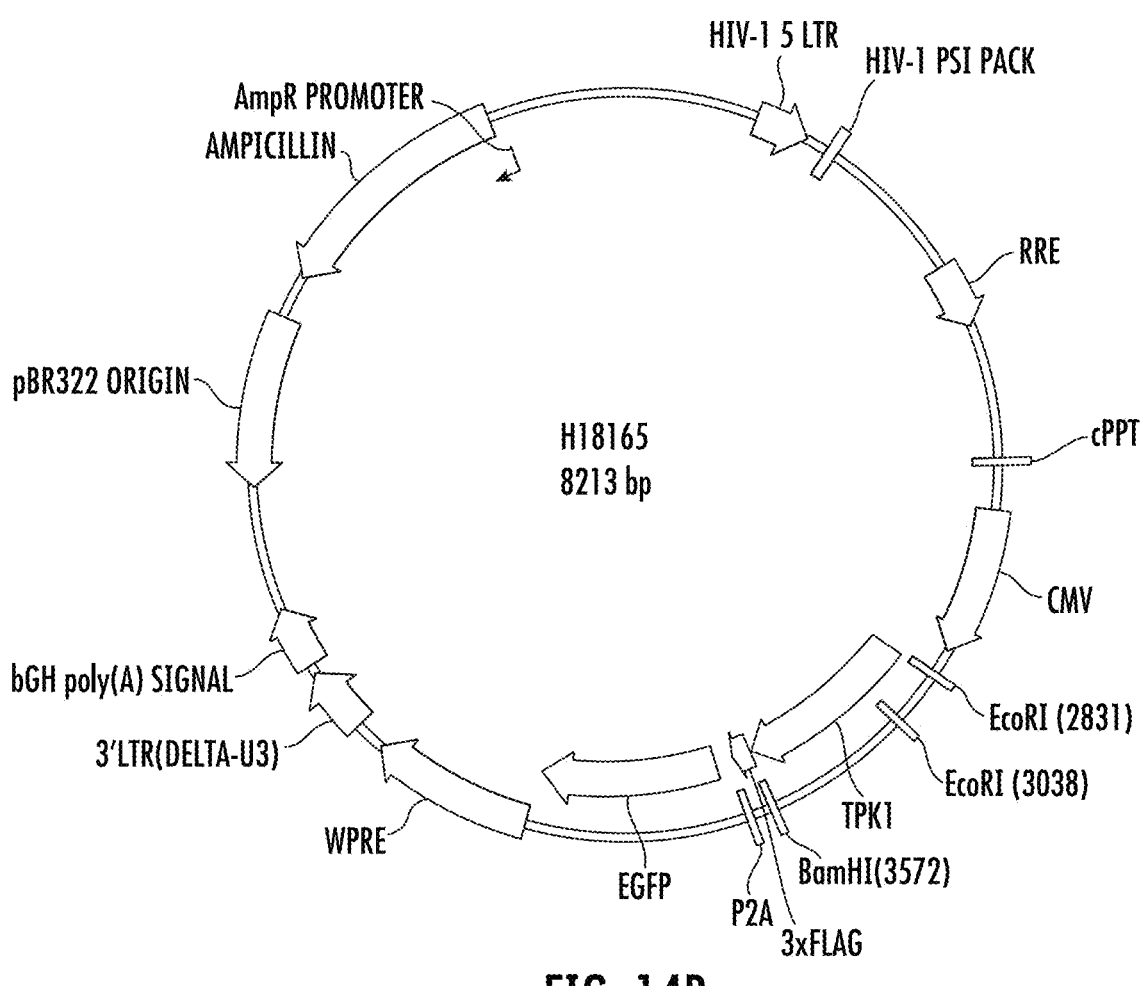

T-Test was employed by statistic analysis. The results of WB test showed that the expression of APP protein in HEK293-APP cells was significantly decreased, and significant differences were observed in all comparisons ($*p<0.05$; $**p<0.01$) (see FIG. 13).

It can be seen that the overexpression of TPK may reduce the expression levels of APP protein in HEK293-APP cells, APP protein levels were reduced with significant difference in both 24 hour and 48 hour groups as compared to the blank control group, showing that TPK overexpression plasmid can inhibit the expression level of APP protein in HEK293-APP cells. Therefore, TPK overexpression can reduce expression level of APP protein in HEK293-APP cells.

The above mentioned are merely preferred embodiments of the invention. It should be noted that a person skilled in the art can further modify and polish the present invention without extend beyond the principle of the invention, which shall also be deemed to be within the scope of the invention.

Example 4

Preparation of rAAV and Recombinant Lentivirus

The CRO company BrainVTA (Wuhan) Co., Ltd. was entrusted with the preparation of the TPK-encoding rAAV (serotype AAV_PHP eB, laboratory-grade), hereinafter referred to as AAV-TPK, and its genome comprises: i) a neuron-specific promoter (SEQ ID NO: 19), ii) a nucleotide sequence encoding TPK (SEQ ID NO: 18) and a WPRE element (SEQ ID NO: 20). The plasmid comprising the rAAV genome is shown in FIG. 17A.

The CRO company OBiO Technology (Shanghai) Co., Ltd. was entrusted with the preparation of the TPK-encoding Lentivirus (laboratory-grade), hereinafter referred to as TPK Lentivirus, and its genome comprises: i) a eukaryotic expression promoter (SEQ ID NO: 23), ii) a nucleotide sequence encoding TPK (SEQ ID NO: 18) and a WPRE element (SEQ ID NO: 20). The plasmid comprising the Lentivirus genome is shown in FIG. 17B.

Example 5

Overexpression of TPK and Increased TPD Content in Neuronal Cells Infected with TPK Lentivirus This Example aims to preliminarily evaluate the effect of gene therapy by experiments at cell level in vitro.

Primary neurons were obtained by digesting the cortex of neonatal mice (purchased from Vital River Laboratory Animal Technology Co., Ltd. with trypsin (Thermofisher/Gibco Catalog 25200072) and cultured in 6-well plates ($1.5 \times 10^6$/ well) for 4 days with 10% FBS+10% F12+1% Glutemax+ 78% DMEM+1% 100× penicillin-streptomycin (5,000 U/mL) on the first day, and then, changed to 96% Neurobasal medium+2% B27+1% Glutemax+1% 100× penicillin-streptomycin (5,000 U/mL). All above reagents were formulated based on volume percentage, and purchased from Thermofisher/Gibco. The medium was removed, and the suspension of the Lentivirus prepared in Example 4 was added (1.5 mL, MOI of 5) for an 8-hr infection, and the Lentivirus encoding GFP but not comprising TPK coding sequence was used as control. The liquid was removed, fresh protein samples were denatured at 95° C. In brief, after the denaturation, the samples were separated by 12% SDS-PAGE and transferred to PVDF membranes. The areas corresponding to the size of the target proteins (25-35 KD for TPK, and 40-55 KD for β-Actin) were cut off according to the protein markers. The membranes were blocked with Western Blot Blocking Buffer (Takara, T7131A) for 1 hour at room temperature, and then, were incubated with the primary antibodies for Tpk1 (1:3000, Proteintech, 10942-1-AP, USA) and β-Actin (1:5000, Beyotime, AF0003, China) at 4° C. overnight. After the recovery of the primary antibodies, the membranes were washed with Tris-buffered saline containing 0.05% Tween-20 (TBST) for 3 times, each for 5 minutes, and then, incubated with a corresponding horseradish peroxidase-conjugated anti-rabbit or anti-mouse antibody (Beyotime, China, A0208 and A0216), respectively, for 2 hours at room temperature, followed by developing with enhanced chemiluminescence detection kit (ThermoFisher, 34095).

Figure 16A:
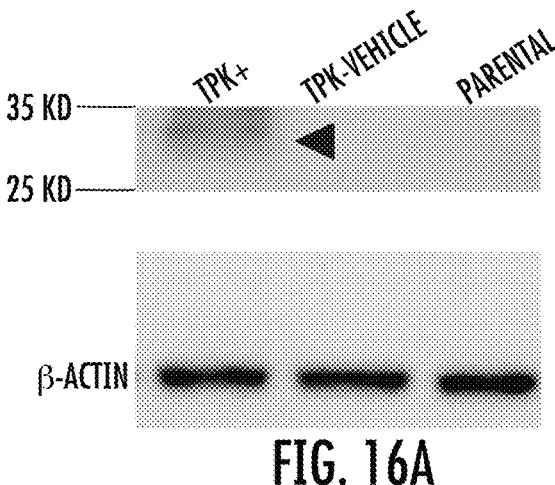
FIGS. 16A-16C show TPK expression (FIG. 16A, parental represents the blank cell that is not infected by virus), Thiamine diphosphate (TDP) content (FIG. 16B) and thiamine (TM) content (FIG. 16C) in cultured neurons infected with Lentivirus.

As shown in FIG. 16A, TPK was significantly overexpressed in cells infected with TPK Lentivirus.

100 μL of supernatant was taken, followed by adding an equal volume of pre-cooled 5.4% perchloric acid (PCA), shaking for blending, and centrifugation at 13,000 rpm and 4° C. for 15 min. The supernatant was analyzed by HPLC with the devices and conditions as shown in Table 1.

TABLE 1

| Equipment and software | Manufacturer | Model |
|---|---|---|
| Liquid chromatography | Thermo Fisher | Ultimate3000 |
| Four element infusion pump/column temperature box/automatic sampler/ | Thermo Fisher | Ultimate3000 |
| Data acquisition software | Thermo Fisher | ES Chromeleon 7.2.10 |
| Chromatographic column | Agilent Technologies | $C_{18}$ (4.6 × 150 mm) |
| Detector | Fluorescence detector (FLD) | |
| | HPLC conditions | |
| Detecting conditions | Ex = 367 nm, Em = 435 nm | |

Figure 15:
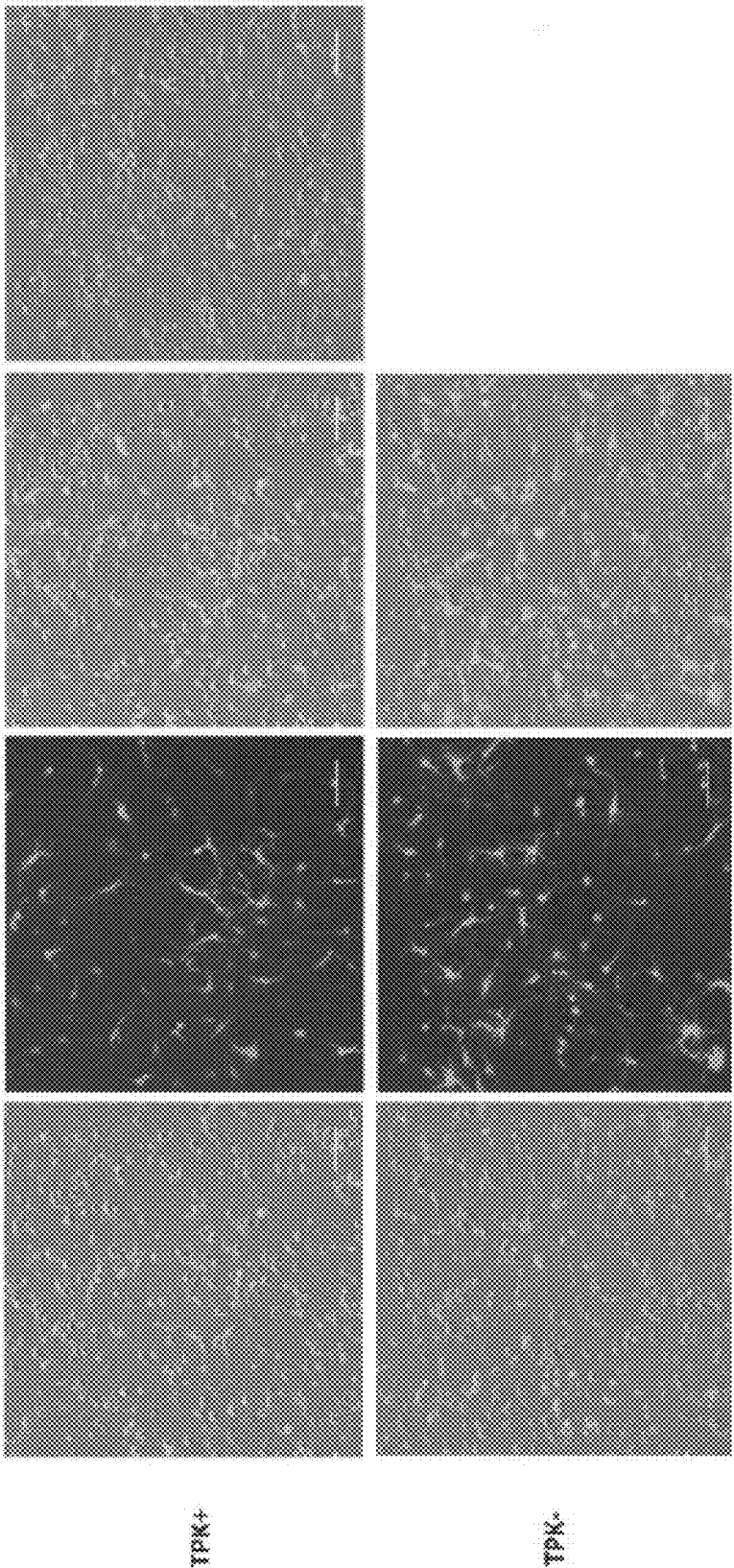
FIG. 15 shows the images of fluorescent microscopy of cultured neurons infected with Lentivirus.

| | | 20 mM Ammonium | |
|---|---|---|---|
| Mobile phase and flow rate | Time (min) | acetate aqueous | Methanol |
| | 0-1.3 | 90 | 10 |
| | 4.2-6.2 | 61 | 39 |
| | 8.6-9.6 | 12 | 88 |
| | 9.7-10 | 90 | 10 |
| | flow rate: 1 mL/min | | | medium was added, and the neurons were cultured for 7 days. GFP expression was observed by fluorescent microscopy. As shown in FIG. 15, a great number of infected cells expressed GFP, indicating the high infection rate of the virus.

The medium was removed, and the cells were washed for three times with pre-cooled PBS, 5 min/time. 100 μL of cell lysing solution comprising RIPA (purchased from Beyotime), phosphatase inhibitor (purchased from Bimake) and protease inhibitor (purchased from Sigma) at a volume ratio of 100:1:1 was added to each well, and all the cells were scraped off, and the cell suspensions were transferred to a 1.5 mL tube on ice; 50 μL of cell lysing solution was added to each well to rinse the bottom of the well, and transferred to the same tube. 2 grinding steel beads were added to each tube for grinding (60 Hz, 60 s, −10° C.); and the tubes were centrifuged at 13,000 rpm, 4° C. for 15 min, and the supernatants were collected and placed on ice.

Figure 16B:
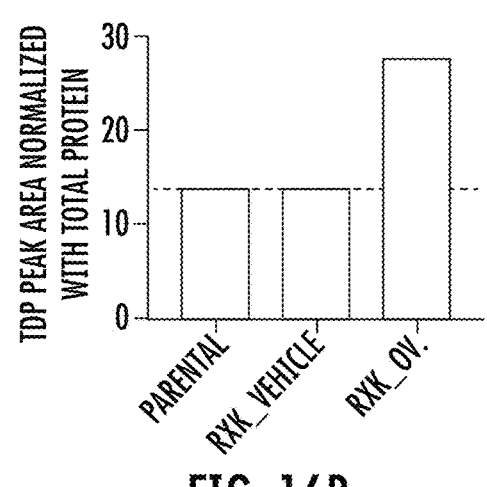
Figure 16C:
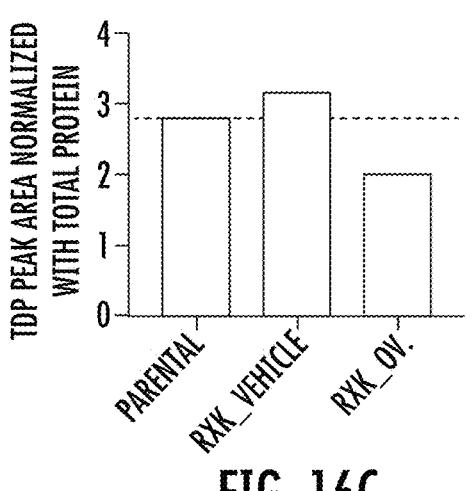

Total protein concentrations in the supernatants were determined by BCA assay; and the TPK levels in the samples were analyzed by Western Blot after the extracted As shown in FIG. 16B, the TDP contents in cells infected by TPK Lentivirus were significantly higher than that in uninfected cells and control virus infected cells, while the TM contents in cells infected by TPK Lentivirus were significantly lower than that in uninfected cells and control virus infected cells (FIG. 16C). The results showed that the overexpression of TPK in cells infected by TPK Lentivirus significantly promoted the conversion of TM to TDP, and the conversion rate was about two times higher than the control group.

Example 6

Overexpression of TPK and Increased TM/TDP Conversion Rate in the Brains of Mice with Tail Vein Injection of AAV-TPK This Example aims to verify whether gene therapy by tail vein injection of AAV virus to C57BL/6J mice could significantly improve the expression of TPK protein in the brains of mice, and increase the conversion rate of TM/TDP in the brains of the mice, to enhance glucose metabolism.

After 3 days of adaptive care, adult C57BL/6J mice (2-month-old) (purchased from Vital River Laboratory Animal Technology Co., Ltd.) were randomly divided into two groups (TPK group and control group, n=3), and were administered, by tail vein injection, with the suspensions of AAV-TPK prepared in Example 4 (TPK group) and control rAAV (same with AAV-TPK except the lack of TPK coding sequence) at a titer of $5.0 \times 10^{12}$ vg/mL (formulated in saline), respectively, 200 µL for each mice. In particular, the mouse was fixed on the tail vein injection fixture, and the mouse tail was wiped with alcohol wipes for disinfection, and 200 µL of the virus suspension was injected into the tail vein of the mouse with a 1 ml syringe. After injection, the injection site was pressed with a dry cotton ball for 30 seconds to prevent virus spillage. The mice were returned to their home cages, and the body weights and food intakes of the mouse were recorded weekly in the 4 weeks.

Figures 17, 18:
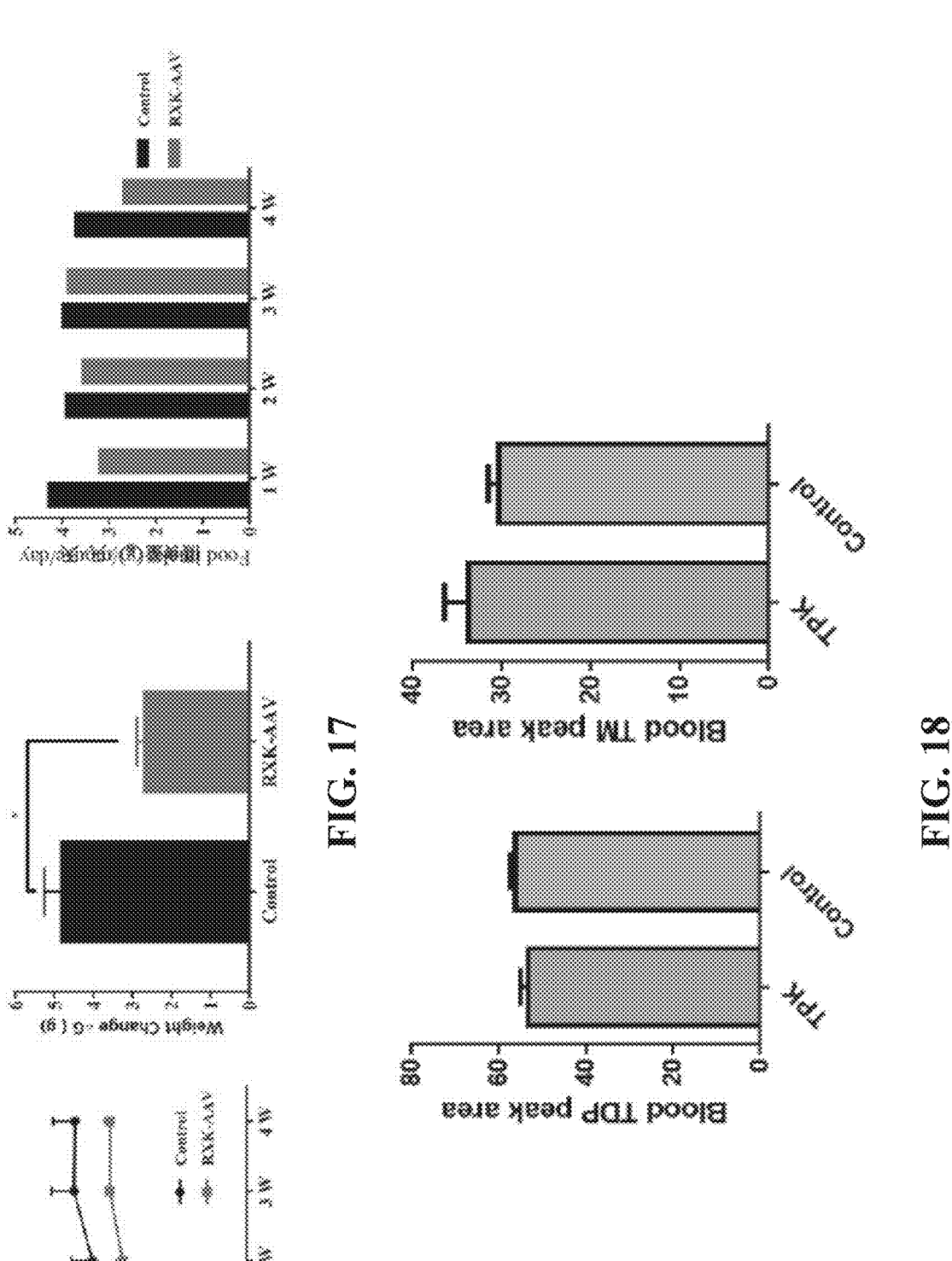
FIG. 17 shows the body weight (left and middle panels) and food intake (right panel) of mice with tail vein injection of rAAV.
FIG. 18 shows the TDP (left panel) and TM (right panel) contents in the blood of mice with tail vein injection of rAAV.

As shown in FIG. 17, after tail vein injections of AAV-TPK, the body weight gains of adult mice were significantly less than the control group, and the food intakes tended to decrease as compared with the control group.

After 4 weeks care, mice whole blood samples were collected using a 3 mL EDTA anticoagulant tubes, and then, placed on ice immediately. The following operations were carried out on ice: 0.3 mL of each whole blood sample was transferred to a 2 mL tube within 10 minutes, and 30 µL of pure water was added, followed by adding 0.3 mL of pre-cooled PCA (5.7%) to precipitate the proteins. After an ice bath of about 30 min, the samples were centrifuged at 12,000 rpm for 10 min at 4° C., and the supernatants were collected and analyzed for TDP and TM contents by HPLC as described in Example 5.

As shown in FIG. 18, 4 weeks after tail vein injection of AAV-TPK to adult mice, the TDP/TM content in peripheral blood was not significantly altered.

After the mouse was euthanized, the heart was perfused with pre-cooled PBS, and then, the mouse brain tissues were collected. The cerebellum, brain stem and olfactory bulb sections were removed, and the left and right hemispheres were separated.

The right hemispheres were fixed with 4% paraformaldehyde (PFA) for immunofluorescence staining. In particular, the right hemispheres were fixed in 4% PFA overnight, followed by immersion in 30% sucrose for at least 2 days for dehydration before being embedded with OCT and stored by freezing at −80° C. The embedded right hemispheres were sectioned into 30 µm thick sections, using a cryostat, along the longitudinal direction from the olfactory bulb to the cerebellum (coronal section). After sectioning, the sections were washed in PBS for 3-5 times to fully remove the OCT, and then, incubated in 0.5% Triton-X100 at room temperature for 30 min followed by blocking the sections with 3% BSA for 1 hour at room temperature. The sections were then incubated with GFP primary antibody dilutions (anti-GFP antibody, 1:2000, Avessellabs, GFP-1020) at 4° C. overnight. After the recovery of the primary antibody, the sections were washed in PBS for 3 time, each for 5 minutes, and then, incubated with the secondary antibody (Goat anti-Rabbit IgG (H+L) Cross-Adsorbed Secondary Antibody, Alexa Fluor 488 (1:1000, Invitrogen, A11008) for 2 hours at room temperature in the dark. Lastly, the sections were placed to the glass slides and imaged with inverted fluorescence microscope (Ti2E, Nikon).

Figure 19A:
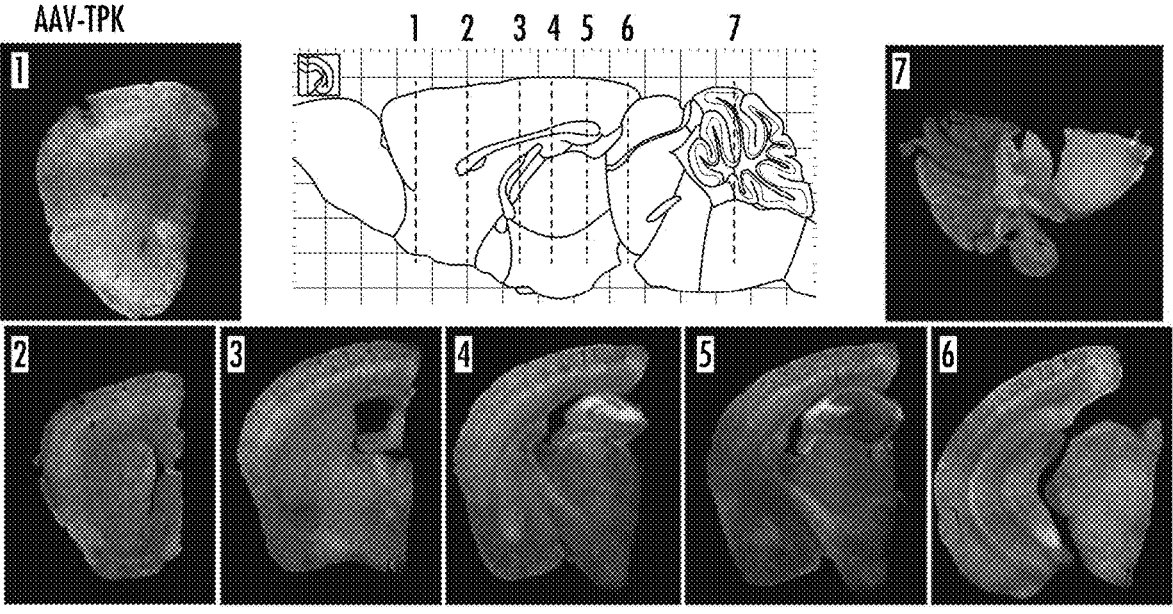
FIGS. 19A and 19B show the images of fluorescent microscopy for sections from various areas in the brains of mice with tail vein injection of rAAV.
Figure 19B:
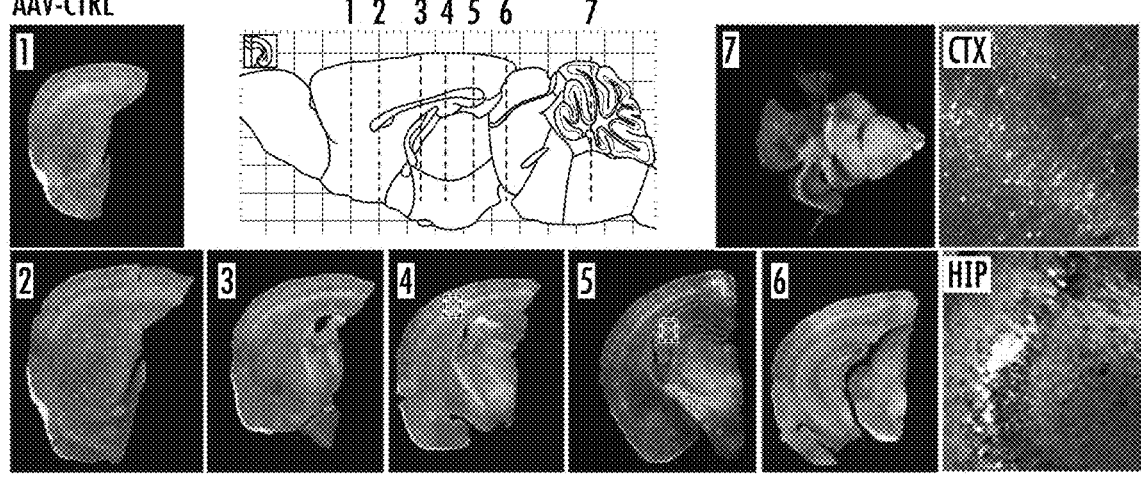

As shown in FIG. 19, 4 weeks after tail vein injection of AAV-TPK to adult mice, the polypeptide encoded by the rAAV viruses was expressed widely in brain tissues.

The left hemispheres and liver tissues were place in cell lysing solution (see Example 5), and lysed in a Freezing Grinder Machine (70 Hz, 60 seconds for two times with an interval of 20 seconds), and then, centrifuged at 13,000 rpm with 4° C. for 15 min. The supernatants were collected and analyzed by Western Blot and HPLC as described in Example 5 to detect TPK expressions in the brain and TDP and TM contents in the brain and liver.

As shown in FIG. 20, 4 weeks after tail vein injection of AAV-TPK to adult mice, in brain tissues, the expressions of TPK and the TDP contents significantly increased, while the contents of TM were comparable to the control group.

Figure 21:
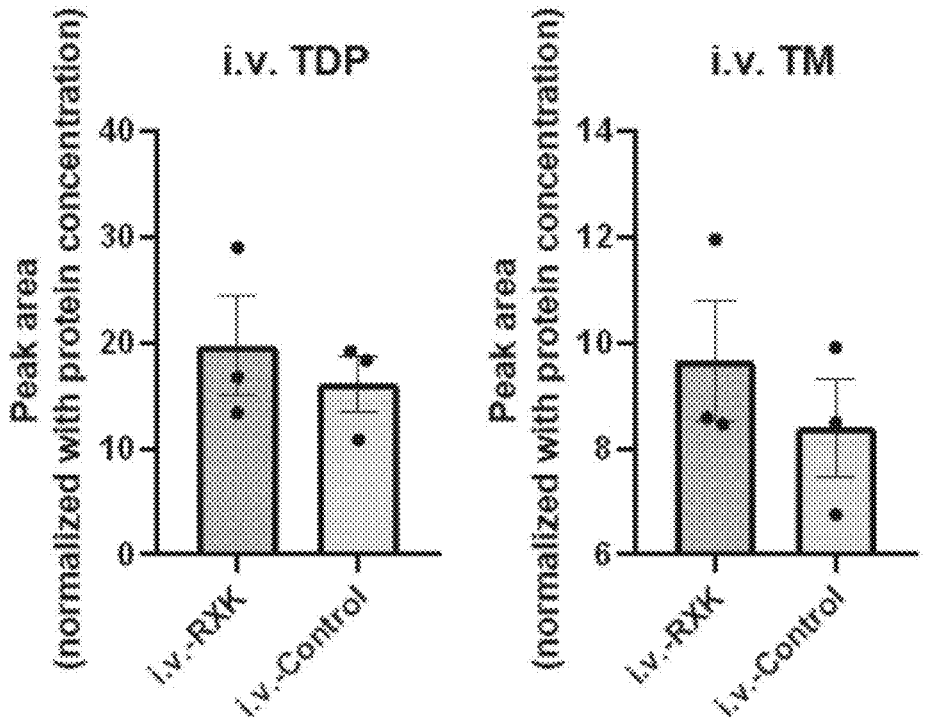
FIG. 21 shows the TDP (left panel) and TM (right panel) contents in the liver of mice with tail vein injection of rAAV.

As shown in FIG. 21, both TM and TDP in liver were not significantly altered, indicating that the virus is highly specific for brain, i.e., specifically target brain neurons without affecting the peripheral tissues, and that the peripheral side effect of the virus was fully controlled.

Example 7

Overexpression of TPK and Increased TM/TDP Conversion Rate in the Brains of Mice with Intracerebral Ventricular Injection of AAV-TPK This Example aims to verify whether intracerebral ventricular injection of AAV-TPK to C57BL/6J mice could significantly increase the expression of TPK protein in the brains of mice, and increase the conversion rates of TM/TDP in the brains of mice, to enhance glucose metabolism.

After 3 days of adaptive care, adult C57BL/6J mice (2-month-old; purchased from Vital River Laboratory Animal Technology Co., Ltd.) were randomly divided into two groups (TPK group and control group, n=5) for stereotaxically intracerebral ventricular injection of AAV. The concentration of the virus stock solution was $1.0 \times 10^{13}$ vg/1 mL, and the amount for the intracerebral ventricular injection to mouse was $4.0 \times 10^{10}$ vg/4 µL (2 µL for each of left ventricular and right ventricular)/mouse. Adult mice were anesthetized with Choutet 50, the hair between eyes and ears was shaved and the mice were fixed on the brain stereotaxic apparatus. The skin covering the brain area was wiped with alcohol wipes for disinfection, and cut with scissors to expose the skull. The surface of the skull was wiped with a dry cotton swab until the bregma could be clearly observed. The coordinate was positioned using the bregma as the origin (AP: −0.2 mm, L/R: ±1.0 mm, H: +2.5 mm). The drilling points were marked and the skull was drilled with a 0.5 mm drill head. 2 µL of AAV virus was pipetted with a 10 µL microinjection needle, and injected at a rate of 0.2 µL/min with a needle depth of 2.5 mm (with the skull surface as the origin of Z axis). The injection needle was left for 5 min, and then, pulled out slowly. After the skin was sutured, the mice were placed in a cage containing a heating pad until awaking, and then, returned to their home cage for 4 weeks' care. The body weights and food intakes were recorded weekly.

Figure 22:
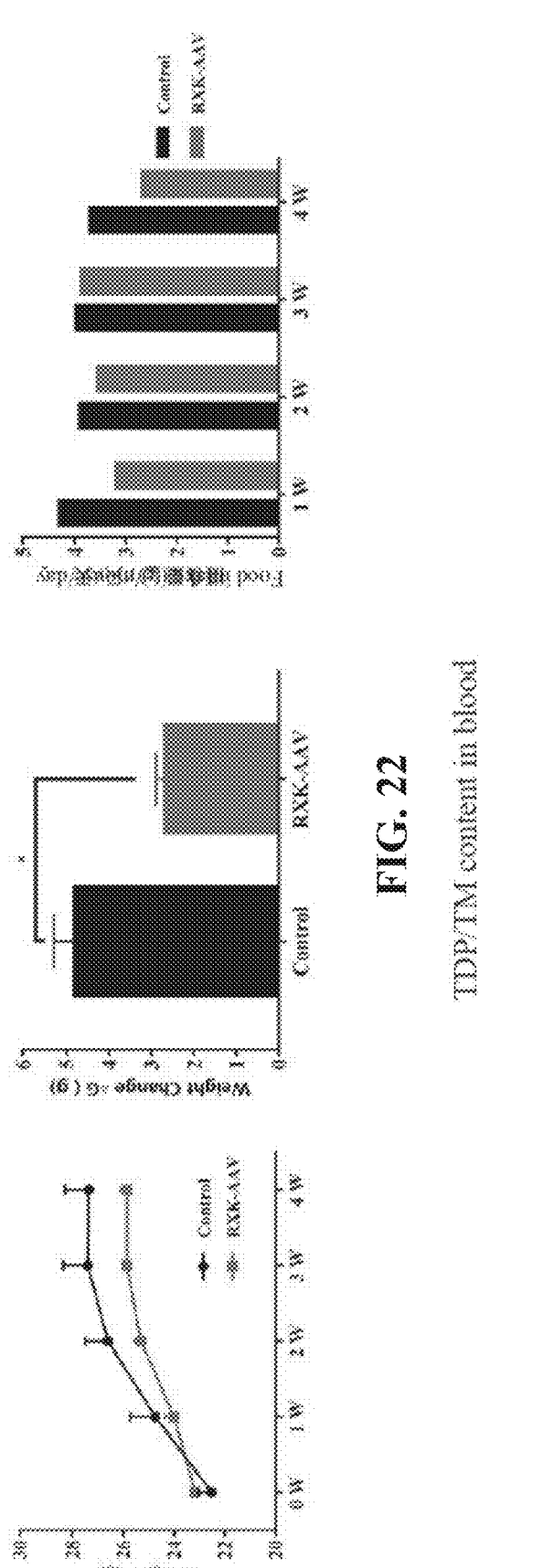
FIG. 22 shows the body weights (left and middle panels) and food intakes (right panel) of mice with intracerebral ventricular injection of rAAV.

As shown in FIG. 22, after intracerebral ventricular injection of AAV-TPK to adult mice, the body weights and food intakes were not significantly different from the control group.

After 4 weeks, blood samples were collected and detected for TDP and TM content. The brains and liver tissues were also collected and detected for TPK expression level and TDP and TM content in the brain and liver tissue, as described in Example 6.

Figure 23:
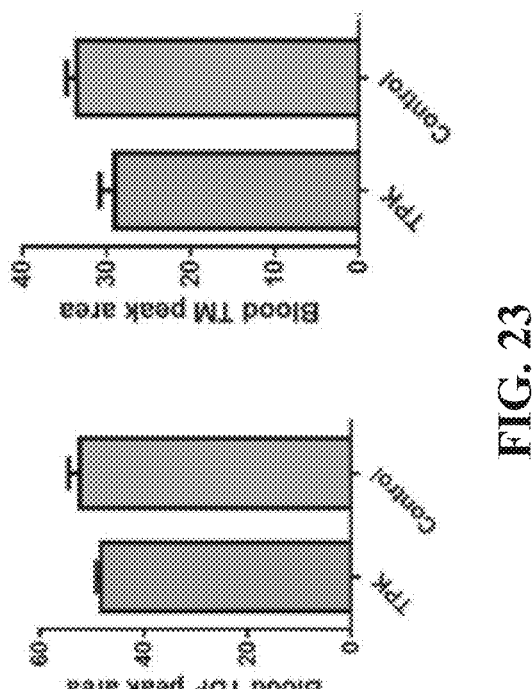
FIG. 23 shows the TDP (left panel) and TM (right panel) contents in the blood of mice with intracerebral ventricular injection of rAAV.

As shown in FIG. 23, 4 weeks after intracerebral ventricular injection of AAV-TPK to adult mice, the TDP/TM contents in peripheral blood were not significantly altered.

Figure 24A:
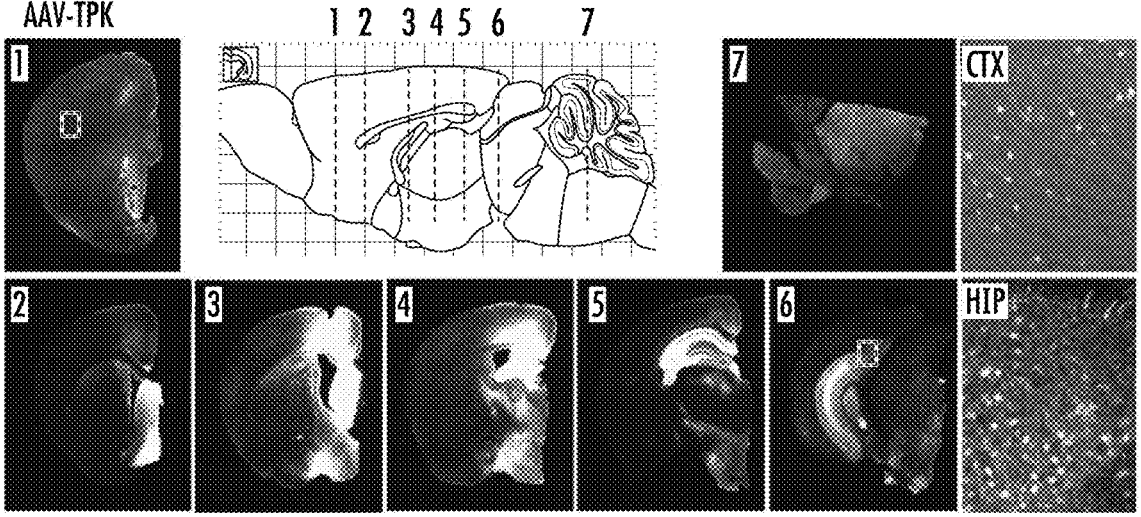
FIGS. 24A and 24B shows the images of fluorescent microscopy for sections from various areas in the brains of mice with intracerebral ventricular injection of rAAV.
Figure 24B:
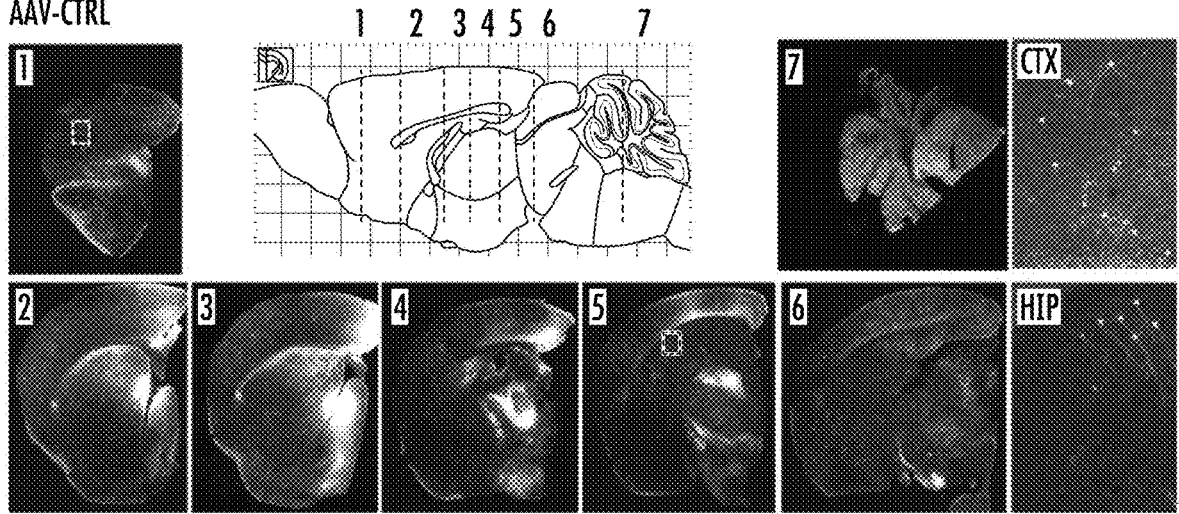

As shown in FIG. 24, 4 weeks after intracerebral ventricular injection of rAAVs to adult mice, the gene products encoded by the rAAV viruses were strongly expressed around the cerebral ventricular, and also expressed in some other brain areas.

Figure 25:
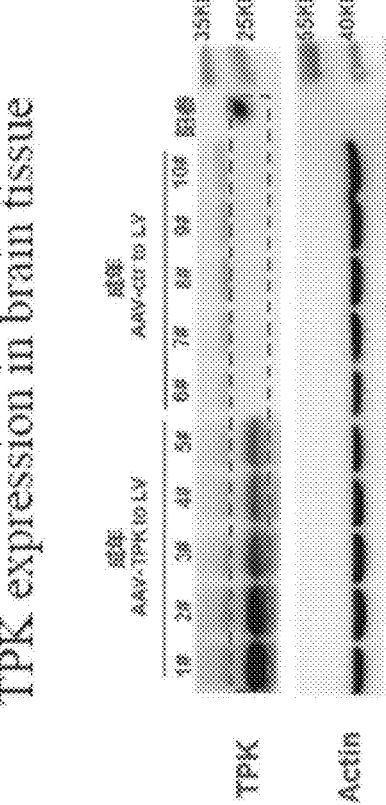
FIG. 25 shows the TPK expression (left panel) and TDP and TM contents (right panel) in the brains of mice with intracerebral ventricular injection of rAAV.

As shown in FIG. 25, 4 weeks after intracerebral ventricular injection of AAV-TPK to adult mice, as compared with the control, the expression of TPK in the brain tissues were significantly increased, the TDP contents significantly increased, while the TM contents decreased, indicating that the TM/TDP conversion rates increased.

As shown in FIG. 26, both TM and TDP in liver were not significantly altered, indicating that the virus is highly specific for brain, i.e., specifically target brain neurons without affecting the peripheral tissues, and that the side effect of the virus was fully controlled.

Example 8

The Overexpression of TPK and Increased TM/TDP Conversion Rate in the Brains of Mice Developed from Embryos with Intracerebral Ventricular Injection of AAV-TPK This Example aims to verify whether the gene therapy means of directly delivery of AAV into the intracerebral ventricular of C57BL6/J fetal mice can significantly increase the expression of TPK in the brains of mice, and improve the conversion rate of TM/TDP in brains, to enhance glucose metabolism.

C57BL6/J mice with 13.5 days of pregnancy (embryo 13.5 days, E13.5) purchased from Vital River Laboratory Animal Technology Co., Ltd. were adaptively cared for 1 day (E14.5), and randomly divided into two groups (n=3): TPK group (injected with AAV-TPK) and the control group (injected with control virus).

After deeply anesthetized, the pregnant mouse was placed belly up. The abdomen was wiped with a tissue dipped with 75% alcohol, and the hair in the center of the abdomen was cut off, and then, the abdomen of the pregnant mouse was wiped with a tissue dipped with PBS to remove the residual alcohol and hair pieces. Surgical instruments were by wiped with 75% alcohol for sterilization. The skin was cut with scissors along the middle of the abdomen of the pregnant mouse for about 1.5 cm, and the peritoneum of the pregnant mouse was cut along the linea alba to expose the abdominal cavity. The embryos were carefully removed from the abdominal cavity of the pregnant mouse with a tweezer and placed on the abdomen of the pregnant mouse (during the subsequent procedure, the abdominal cavity of the mouse and the surface of the embryos were kept moist with PBS). The embryonic brains were gently pierced with a glass electrode which absorbed the rAAV virus suspension, and the virus suspension was transferred to the intracerebral ventricular of the embryos by blowing, 0.5-1 µL (5.0× $10^9$~10×$10^{10}$ vg) of virus suspension for each side of cerebral ventricular of each embryo. The embryos were put back into the abdominal cavity of the pregnant mouse, and the peritoneum and the skin of the mouse was sutured successively with sutures. After the suture was completed, lincomycin-lidocaine gel was applied for alleviating pain and preventing the wound from inflammation and infection. Then, the mouse was placed on a heating pad until awaking, and then, transferred back to their home cages for care.

After birth, the offspring mice were irradiated with an excitation light of 480 nm to detect the virus injection results, and the mice which were successfully injected with the virus were retained. After 21 days of care, all the mice were ablactated 21 days after birth as standard. 3 mice of each group were treated as described in Example 6 for collecting samples, detecting TDP and TM contents in blood, TPK expression level in the brain and TDP and TM contents in the brain and liver tissue; and another 12 mice of each group were ablactated and recorded for body weight in two weeks.

As shown in FIG. 27, the body weights in two weeks post-ablactation of mice developed from embryos injected with AAV-TPK was not significantly different from the control group.

As shown in FIG. 28, TDP/TM contents in peripheral blood of mice developed from embryos injected with AAV-TPK were not significantly altered.

Figure 29A:
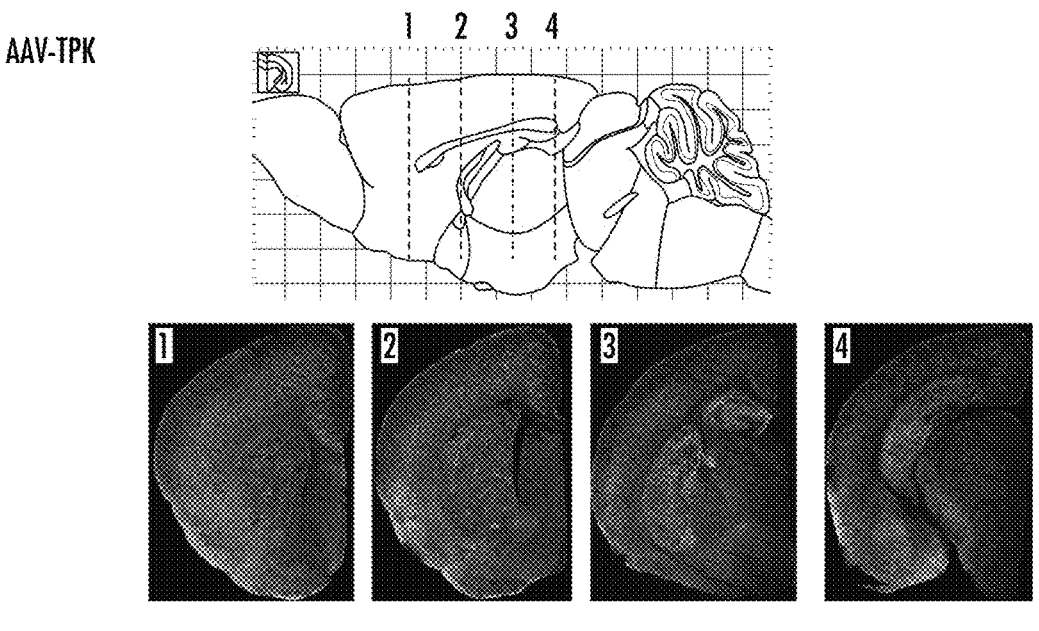
FIGS. 29A and 29B shows the images of fluorescent microscopy for sections from various areas in the brains of 21-day postnatal mice developed from embryos with intracerebral ventricular injection of rAAV.
Figure 29B:
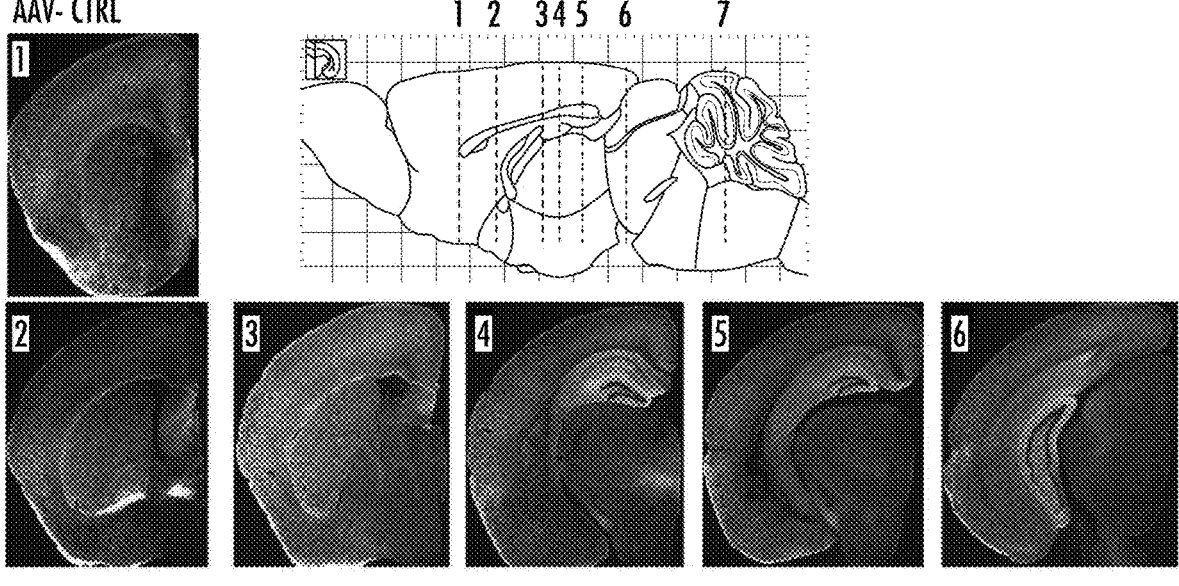

As shown in FIG. 29, in mice developed from embryos injected with the rAAVs, the gene products encoded by the rAAV virus were widely expressed in the cortex and hippocampus, as well as in some other brain areas.

As shown in FIG. 30, compared with the control group, the expressions of TPK in the brain tissues of mice developed from embryos injected with AAV-TPK were significantly increased, the TDP contents were significantly increased, and the TM contents were decreased, indicating that the TM/TDP conversion rate was increased.

As shown in FIG. 31, both TM and TDP in liver were not significantly altered, indicating that the virus is highly specific for brain, i.e., specifically target brain neurons without affecting the peripheral tissues, and that the side effect of the virus was fully controlled.

Example 9

The Overexpression of TPK and Increased TM/TDP Conversion Rate in the Brain of Neonatal Mice Stereotaxically Injected with AAV-TPK This Example aims to verify whether direct delivery of AAV-TPK into the intracerebral ventricular (ICV) and hippocampus (Intraparenchymal, IP) of neonatal mice (Postnatal day 0, P0) could significantly increase the expression of TPK in the brain of C57BL6/J mice, and improve the conversion rate of TM/TDP in neurons, to enhance glucose metabolism.

A total of 11 C57BL6/J mice (18.5 days of pregnancy (embryo 18.5 days, E18.5)) were purchased from Shanghai Jsj Laboratory Animal Co., Ltd. Experiments were performed after the birth of neonatal mice.

Intracerebral ventricular injection site: 1 mm forward, 1 mm left and right, respectively, and 1 mm deep from the lambda. Intracerebral ventricular injection was performed bilaterally, and 800 nL of virus suspension was injected into each side.

Hippocampal injection site i): 0.7 mm forward, 1.2 mm left and right, respectively, and 0.9 mm deep from lambda; hippocampal injection site ii): 0.1 mm forward, 2.2 mm left and right, and 1.4 mm deep from lambda. Both sides of the hippocampus were injected at two sites, with a total of four injections in each mouse, 200 nL of virus suspension per injection.

After filling the glass electrode with paraffin oil, the glass electrode was fixed on the microsyringe with a hot melt gun, and the needle of the microsyringe was inserted to about ⅓ of the glass electrode, and the microsyringe was fixed on the automatic injection pump.

The virus suspension was aspirated into the glass electrode by a syringe pump. The fully anesthetized neonatal mice were fixed on a horizontal vessel with a medical tape as long as its head was kept horizontal. Under the stereo microscope, the lambda of the mouse head was determined as the origin, the syringe was moved by the operating arm to the designated position, and the height of the syringe was adjusted with the vertical operating arm (Z-axis) and the needle was moved down to the designated position with the position where the needle slightly sunken after contacting the head set as the origin. Finally, the virus was automatically delivered into the brain of the neonatal mice through the controller for the syringe pump. After the injection, the needle was left in the brain of neonatal mouse for about 3 minutes, and then, the needle was pulled out slowly.

After the injection was completed, the neonatal mice were quickly transferred to a heating pad. After the recovery of the body temperature of the neonatal mouse and the starting of movement, they were put back into the cage of the mother mice, and the cage bedding was applied to the neonatal mouse for a period of time to left it with the smell. When the mother mice positively took the neonatal mice back to the nests, the stereotaxic experiment was completed.

After 21 days of care, all the mice were ablactated 21 days after birth as standard. 3 mice of each treatment were treated as described in Example 6 for collecting samples and detecting TDP and TM contents in blood, expression of polypeptide encoded by rAAV virus in the brain, and TPK expression level and TDP and TM contents in the brain and liver tissue; and other mice (n=11 of each group for intracerebral ventricular injection, and n=8 of each group for hippocampal injection) were ablactated and recorded for body weights, and then, cared and weighted in separate home cages for two weeks.

Figure 32:
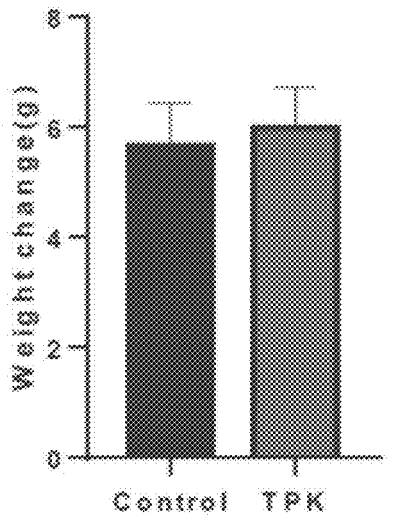
FIG. 32 shows the changed body weights of the mice which was infected at birthday with intracerebral ventricular injection of rAAV in two weeks after ablactation.
Figures 36, 37:
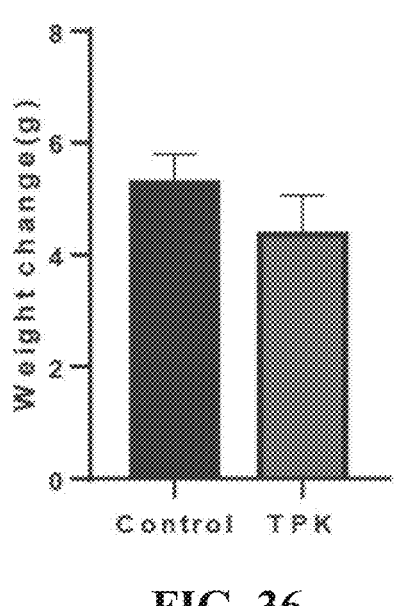
FIG. 36 shows the changed body weights in two weeks after the neonatal mice with hippocampal injection of rAAV were ablactated 21 days after birth.
FIG. 37 shows the TDP (left panel) and TM (right panel) contents in the blood 21 days after the hippocampal injection of rAAV to neonatal mice.

As shown in FIG. 32, the changed body weights of intracerebral ventricular injection of AAV-TPK to P0 mice in two weeks post-ablactation were not significantly altered compared with the control group; and the changed body weights of hippocampal injection of AAV-TPK to P0 mice in two weeks post-ablactation were not significantly altered as compared with the control group, either (FIG. 36).

Figure 33:
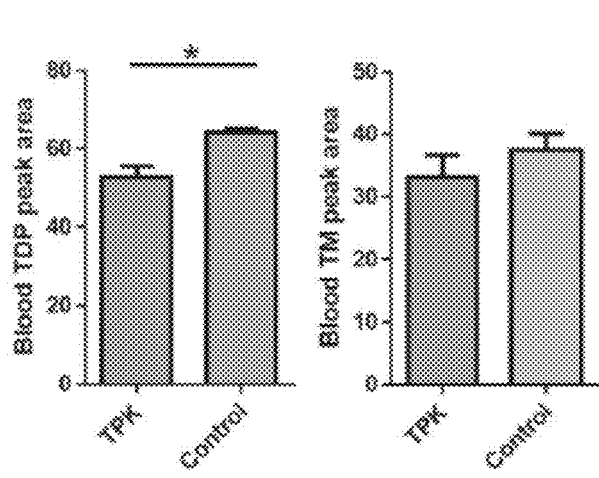
FIG. 33 shows TDP (left panel) and TM (right panel) contents in the blood of neonatal mice 21 days after the intracerebral ventricular injection of rAAV.

As shown in FIG. 33, 3 weeks after hippocampal injection of AAV-TPK to P0 mice, the TDP and TM contents in peripheral blood were not significantly altered.

Figure 34A:
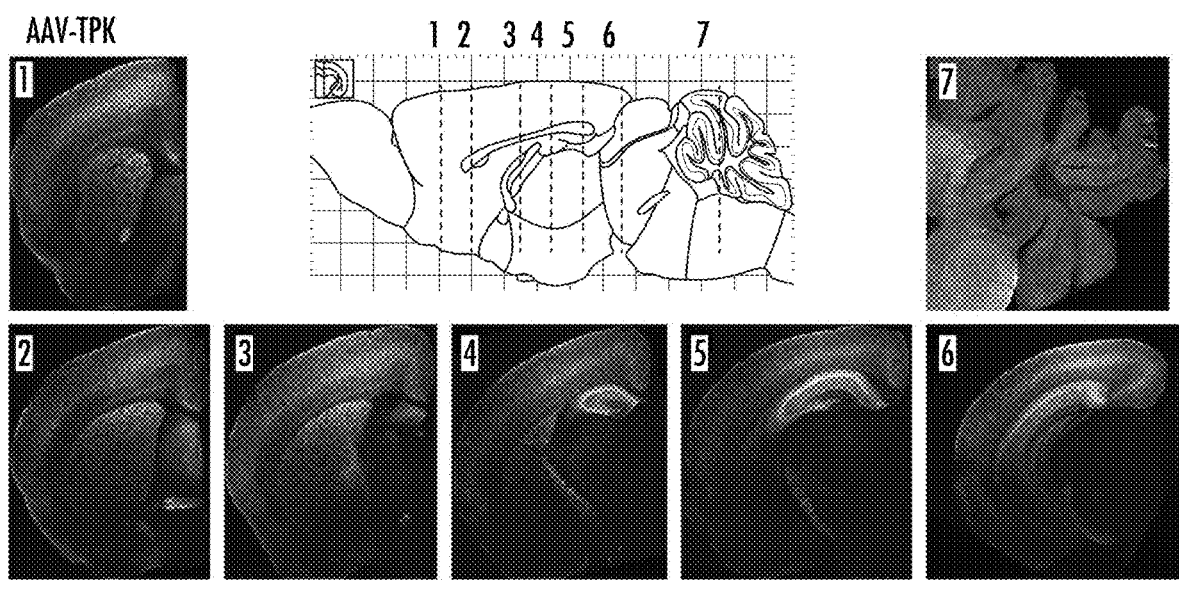
FIGS. 34A and 34B shows the images of fluorescent microscopy for sections from various areas in the brains 21 days after the intracerebral ventricular injection of rAAV to neonatal mice.
Figure 34B:
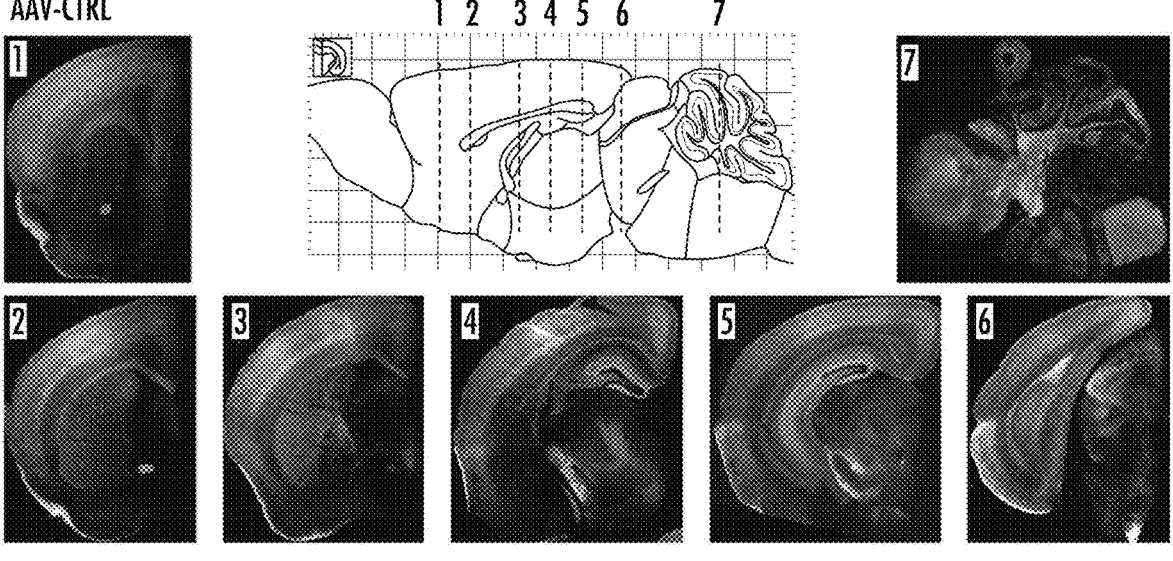
Figure 38A:
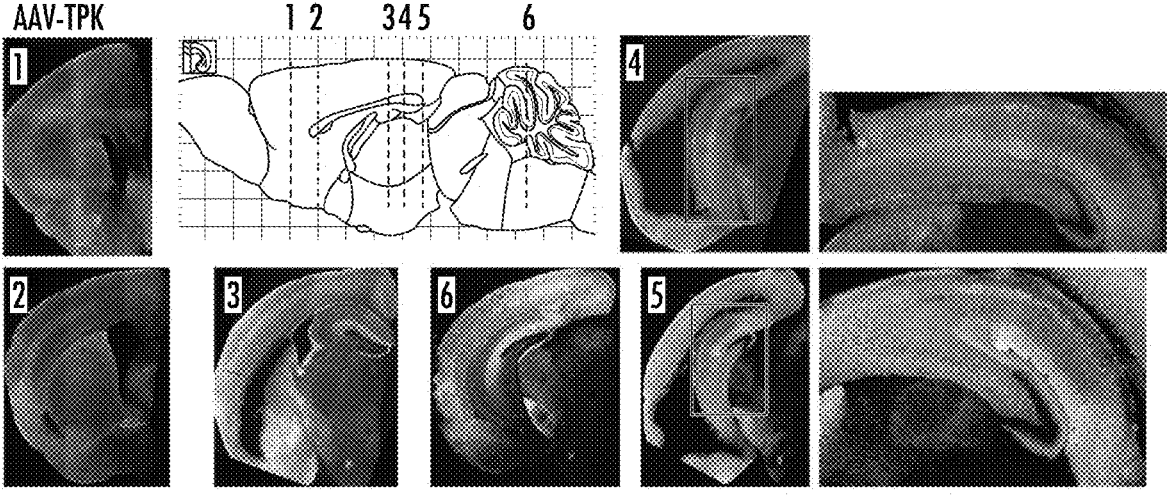
FIGS. 38A and 38B shows the images of fluorescent microscopy for sections from various areas in the brains 21 days after hippocampal injection of rAAV to neonatal mice.
Figure 38B:
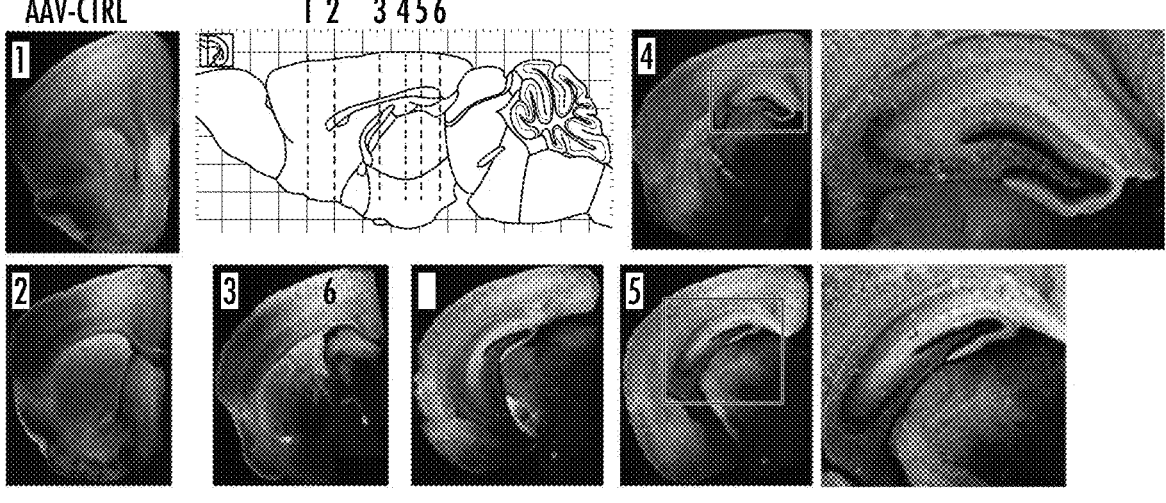

As shown in FIG. 34, 3 weeks after intracerebral ventricular injection of rAAV to P0 mice, the gene products encoded by the rAAV were widely expressed in the cortex and hippocampus, and also expressed in some other brain areas, and 3 weeks after hippocampal injection of rAAV to P0 mice, the gene products encoded by the rAAV were strongly expressed in the hippocampus and also expressed in some other brain areas (FIG. 38).

Figure 35:
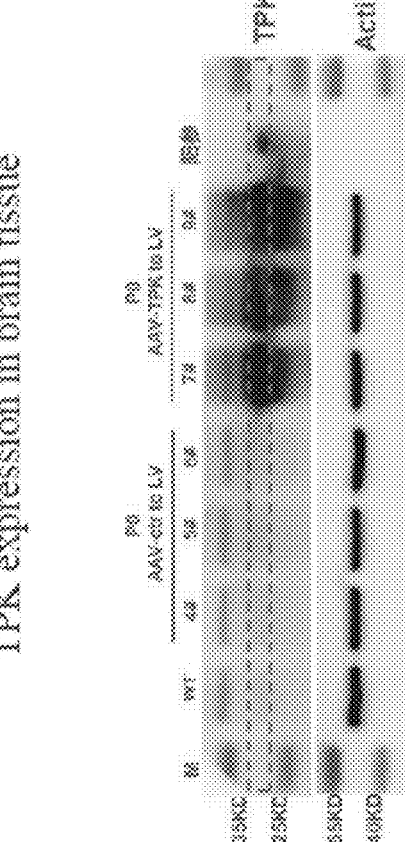
FIG. 35 shows the TPK expression (left panel) and TDP and TM contents (right panel) in the brains 21 days after the intracerebral ventricular injection of rAAV to neonatal mice.
Figure 39:
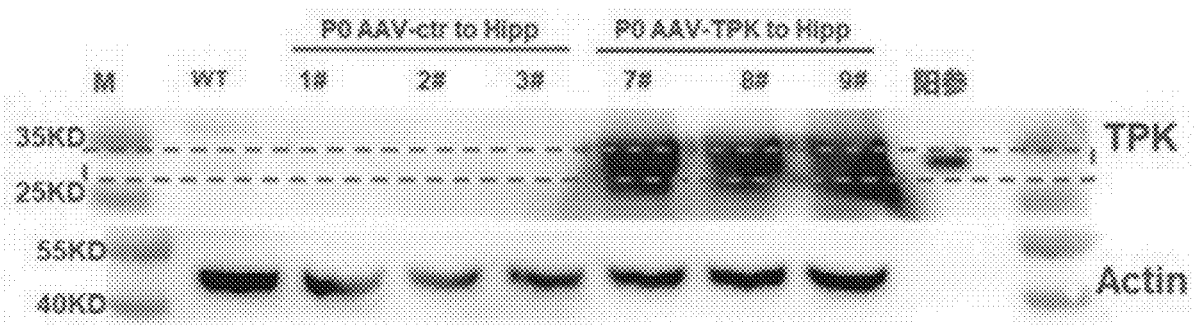
FIG. 39 shows the TPK expression in the brains 21 days after the hippocampal injection of rAAV to neonatal mice.

As shown in FIG. 35, 3 weeks after intracerebral ventricular injection of rAAV to P0 mice, compared with the control group, the expressions of TPK in brain tissues were significantly increased, the TDP contents were significantly increased, and the TM contents were decreased, indicating that the conversion rates of TM/TDP were increased. As shown in FIG. 39, 3 weeks after hippocampal injection of AAV-TPK to P0 mice, compared with the control group, the expression of TPK in brain tissues were significantly increased.

Figure 40:
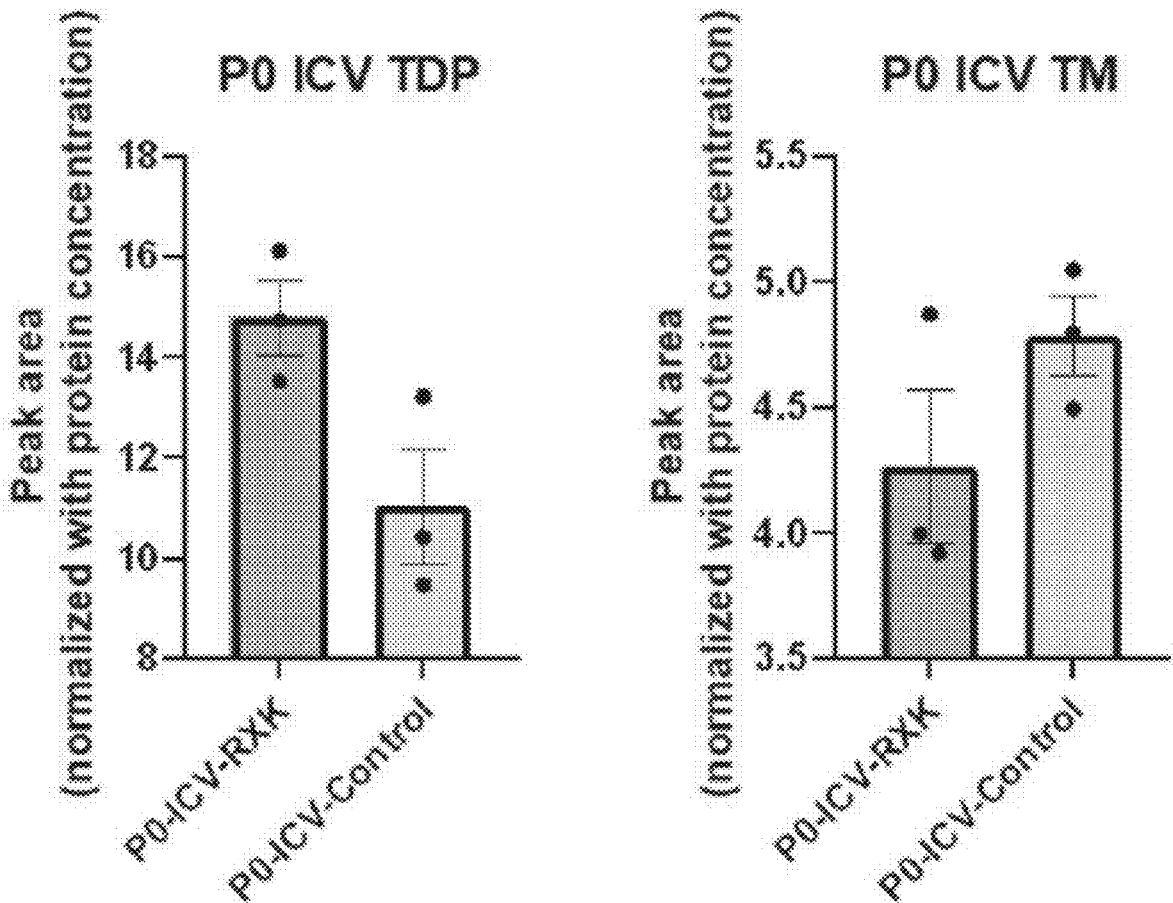
FIG. 40 shows the TDP (left panel) and TM (right panel) contents in the liver 21 days after the intracerebral ventricular injection of rAAV to neonatal mice.

As shown in FIG. 40, both TM and TDP in livers were not significantly altered, indicating that the virus is highly specific for brain, i.e., specifically target brain neurons without affecting the peripheral tissues, and that the side effect of the virus was fully controlled.

What is claimed is:

1. A recombinant adeno-associated virus (rAAV) or recombinant Lentivirus comprising a polynucleotide comprising an expression cassette comprising a polynucleotide encoding thiamine pyrophosphokinase (TPK) polypeptide operably linked to a neuron-specific promoter.

2. The rAAV or recombinant Lentivirus of claim 1, wherein the TPK polypeptide is a mouse TPK polypeptide or a human TPK polypeptide.

3. The rAAV or recombinant Lentivirus of claim 1, wherein the promoter is a eukaryotic promoter.

4. A pharmaceutical composition comprising the rAAV or recombinant Lentivirus of claim 1.

5. A method for promoting glucose metabolism, for preventing or treating a glucose metabolism disorder, or for increasing TPK activity in a subject, the method comprising administering to the subject the rAAV or recombinant Lentivirus of claim 1.

* * * * *

SEQUENCE LISTING

```
<160> NUMBER OF SEQ ID NOS: 23

<210> SEQ ID NO 1
<211> LENGTH: 13237
<212> TYPE: DNA
<213> ORGANISM: Artificial Sequence
<220> FEATURE:
<223> OTHER INFORMATION: Artifically synthesized vector sequence

<400> SEQUENCE: 1
ctaaattgta agcgttaata ttttgttaaa attcgcgtta aattttttgtt aaatcagctc      60 attttttaac caataggccg aaatcggcaa aatcccttat aaatcaaaag aatagaccga     120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt tttttggggt cgaggtgccg taaagcacta aatcggaacc ctaaagggag     300
cccccgattt agagcttgac ggggaaagcc ggcgaacgtg gcgagaaagg aagggaagaa     360
agcgaaagga gcgggcgcta gggcgctggc aagtgtagcg gtcacgctgc gcgtaaccac     420
cacacccgcc gcgcttaatg cgccgctaca gggcgcgtcc cattcgccat tcaggctgcg     480
caactgttgg gaagggcgat cggtgcgggc ctcttcgcta ttacgccagc tggcgaaagg     540
gggatgtgct gcaaggcgat taagttgggt aacgccaggt ttttcccagt cacgacgttg     600
taaaacgacg gccagtgaat tgtaatacga ctcactatag ggcgaattgg gtacgcggcc     660
gcgtttgggg gatgggagtc agtgaggaca tcctcttaga aacaggggaa gaggagtgga     720
ctgaggaaca gttggaggac agaacaaact ggaggggat agcgactggg ctggaaaaaa     780
gaagagatta aagtcaaaaa taatgactaa agccaaatgt agtgacacgt ttctgtagtc     840
```

```
ctataatgta ggaggctgat tctggaagat cacatattca aacaagtagc atactagtgt      900
atatagaaac aacttccttg gtggtaggat atgaggccta ttgaatagtc atcagtgttt      960
acatgatagt catgtatgca tgctatgttt ttttctatta ctatatgtat gcaataacaa     1020
ttatccttat gcttaccatc ttgtctatgt agacaagaat ttatattgtc tatctaggat     1080
ttctgcatca cagaggaagc acagtttaaa atactgtaat gtacagttgt ctgttcattt     1140
acacatattc ctcggcatct cccctcttgc tttatctaca ttgcctttct gtcatttctg     1200
gatatttatg ttaattggtg gcatacacca tagtaatttt ggtgattttc cattaaaatc     1260
agagctgtag ggattagttt aaaatcattg tgctagtcag aattcataga tactgggacc     1320
aaaatcgaac tccagtgttc ttttaagtca ctaaaatgtc gagatctttt ttttcttcct     1380
ctctacctcc tcctcttttt tttttcatat aaatacttgg aattacttta ataaatatact    1440 ttgcagtaag tgaaattatt tctcttcagt tttattcaac agaagatttt gaaatagcca     1500
atttacctgt agttgtaagt acagttcttt tttttgttgt tgttaatatt gctaaatgct     1560
gagttaaaaa acaacactta agatatcttt aacattctca gagttccttc gatagaacag     1620
ttgttccagt ggttttttagt gtgtttttagt tttcacatgt ttatcaacct gaagcacagt    1680
aaataattct tcaaccatta ccagacaatc tgcaaaaaat ttgctgtata agctaatgaa     1740
catttgacat taagagctaa ctcatgcagt aatgcttagg acaatgtaaa ttatgatgaa     1800
tggatatttt gggaccaatt tattgtgatt tatctgacgc ttcctttagc atgccctcca     1860
tttcggggtc tgttacatca tctttctctt tattggttat atgtattgca tgttttttaa     1920
attgcctcgt gtgaacctgt gctatcactg cttgctatat tcttcaaata ttttattttg     1980
caattaattt tatttatatg tttgtaaaat ttgaaaatag ttttttgaat aaagttttta     2040
aaaagtaaag aaaattttta tggtacctta taggaatcaa attgttctga aagcgaattc     2100
ttttcccttc agaaggaata tatccacatt tctaacttat gtgtaacaag aggatagtct     2160
gtacatttcc ttagttatta ttctcagttt ctacttataa ccttgataat atggataaat     2220
ttagttactg tttgtctttc ataagtttcc ctaaatctat tacataaaat atgttagaaa     2280
taatgtcttc aatttttttt gattgaaaaa ataatgggaa tgttatcaga gatgggtgtg    2340
ttgagtgcct tccggtgtct tcctttgatg ctgcctcttc tgctcattgc aaatgaagct     2400
tttgttagtc tagaggacat acatacattt gcttctcact ccattccctt ccacagcaac     2460
gtgtgcttgc ataacaacta aacgaaaata acctgtgtct tgtttatttt gttttgtttg     2520
tttgtctgtg atatcactgg ggacaaaacc atgcttcaca aatgctaggt cagcacttta    2580
tcacacatct ttacccccgg ctcttaaaat tacttaaacg ttgaattcag ctgatctttg    2640
ctatgtaata tagtatggaa attgatatca ttatacttgt taatttttac cagttaaaca     2700
ctatttcttt cattttatag tgctttagta aataaatttt tacataaaag atctcaaaaa    2760
cttgttaatt ttgtttatgg agaattactt tttatactct gagggtaatt actgatcgtt     2820
taccatctgt ttctattaat cagtcttttt atgctcccca atcagtgata tttgctattt     2880
tatgtgagtt catttttccc tctccactga tgatgatttt gatatgttgg aaatgtgcca    2940
caaattcaat gaacttctgt tgtattccta gcgtaatatg aacgtgggtt ctagtcatta     3000
taaagtgttt agggtggtta atgaaactag ccacccctct gagttgtttt tatataaact     3060
ctaatttcat ttaatatttt gtagtagctt gggctcttct tttctaaaat gtaaacttct     3120
catattttga aaaattctaa caaaaagcag agaaaactgt ttactgaatg cccagtgtgt     3180
```

```
tcatgtgttg tgactagatg taattactaa attactaatt gtttaatgac cctactctgt   3240
agtatagaag ctcaagctaa aacttagtgt tttaccccct tagcctgatt ttgtttcata   3300
tatgacaggg atcacagaat agatagactt tgatgagctt ttcagtctgt ccatagagtt   3360
tgatagctaa ccattgcatt ctctcttctg atgttagcat atcaaaaatt agagttgaat   3420
gttcgaaatc tacttaaata taggtaaatc tgcacacacg atggtgatag gatagttttg   3480
aaaatgaaga attaggtcaa cagagtagtt tgtttcttct gaagctattt ctgtcttagg   3540
catttgctca tgctatgact tagtgtggaa gacgttgaaa ttttggacta ggaaatcagt   3600
tgaatgctgt gagtggaact tattgggctg ttctatttgg agcctggaag agagtgctgt   3660
tgagagtaat acagacagtg gaaacccaca gataggaata aagactctat tagcatttgg   3720
gatacacgct attcatgaaa tattttggaa aaaaaccaat ctggctatat ttttccactt   3780
gcttgagatg taagtaatga actaatttat ttggtggagg aaatttcaag atagcatgaa   3840
tttggggttg tggcatcatt actaccgatt acacttgtat aaatctacaa tgaaaaagta   3900
accaatgtac ttaatagctt ggatcttaat agttgtatag gggcagaaga caagacattg   3960
gtctgttaaa gataaagaaa ttgccatgat atcctgttaa atcaccaata tcgtgcaacc   4020
attcctacac cataggataa aaaaattgat tattcttaac tcctagggca aggatttaaa   4080
aaaaaattaa acgaggccaa ggctctctaa atcaacatga tcgaatctca catgaactct   4140
cagagaacca ggcgctgttc tcagttctgc acaaggtttt ttacatatac attatgactt   4200
tcagtttagt gtttttaatg gaattcctaa gtgtaagaac tagtgggcct tttttcttgt   4260
gccttctctg gggcattttc tttctctctc tctttttttt ttgtctagct ccaatatatt   4320
aatttttgtt ttatctcatt ttattttatt ctaaaaacga agcattaaaa agtagcaaca   4380
aaatgccata aagatccttt cttgaaaatt gatttaatag tttaaaaaca gtaatcttaa   4440
ctactaatat taacacccaa ttattaacat aatattgatg tttgacataa ttgaagagag   4500
gttttataaa ttgcaagaga gttgaaggaa ggtcacatac agaagaaaga caagaatgaa   4560
acatctggag aaaggtcgag ggaaggtaag actgtcccca gaaatgtttc agtggaattc   4620
ccagagacag acaggtaaac aggacagagg atggaaagta attgacttaa gatgacttag   4680
attcatgaga acttgagaga tccgcttcct cagctgtggg gagcacagtc tgcttaggca   4740
taattttgaa gttcaagaca tcagagaaaa ggaagatctt caatgtttct agagggaaga   4800
caaacagagg cacagaactg tgaaacaggc tgtcacttga atataccaca gttcccagta   4860
gaattccaaa gccagcatgt taacatagtc aaagcaactg gctgtcagaa gctgtagcct   4920
gccgtcttta taagcctgaa cccagcttcg gtaataaaag agggagctag cgtcgacacg   4980
tataacttcg tataatgtat gctatacgaa gttattactg cgtacgaaaa ggtagaatgt   5040
agagcaggta gctccatatc ttctccacct ctgttcagat ggactggaga agatgcaaag   5100
ggtctgtgag tggttctgtc ttccaatgta gagtcacctg taataacaat agacacgcca   5160
taaggtaaat gtcatgatcc agggtagtgt gccaatatgc tctgagtgtt tgctctttag   5220
tgatgctcac atgacacact gtgctttgct atctctactg acataagatt tgtattcttt   5280
ttgtttgaag ctctcttaag agcctgtgct gatgggggtg ccaaccactt atatgatctc   5340
actgaaggag agagagaaag gtaagctcca gcgagtcagg gtctacatgg tcctcacttc   5400
tgctgctcct tgcttttaat tattctgtgg tgactagttc ttttttcttca tattcatcat   5460 aggaaaccac ctctgtgaga gggctgggct gtataaccat gatgcattac ttctttctat   5520
gaatgagatc tcttagaatt aggatcatgt tttgtcttgt ttttaaatct gtattctatt   5580
```

-continued

```
actttaaagc ctagctaagt cacattatca tgtattgaaa tttatcgata agcttgatat    5640
cgaattccga agttcctatt ctctagaaag tataggaact tcaggtctga agaggagttt    5700
acgtccagcc aagctagctt ggctgcaggt cgtcgaaatt ctaccgggta ggggaggcgc    5760
ttttcccaag gcagtctgga gcatgcgctt tagcagcccc gctgggcact tggcgctaca    5820
caagtggcct ctggcctcgc acacattcca catccaccgg taggcgccaa ccggctccgt    5880
tctttggtgg ccccttcgcg ccaccttcta ctcctcccct agtcaggaag ttcccccccg    5940
ccccgcagct cgcgtcgtgc aggacgtgac aaatggaagt agcacgtctc actagtctcg    6000
tgcagatgga cagcaccgct gagcaatgga agcgggtagg cctttggggc agcggccaat    6060
agcagctttg ctccttcgct ttctgggctc agaggctggg aaggggtggg tccgggggcg    6120
ggctcagggg cgggctcagg ggcggggcgg gcgcccgaag gtcctccgga ggcccggcat    6180
tctgcacgct tcaaaagcgc acgtctgccg cgctgttctc ctcttcctca tctccgggcc    6240
tttcgacctg cagcctgttg acaattaatc atcggcatag tatatcggca tagtataata    6300
cgacaaggtg aggaactaaa ccatgggatc ggccattgaa caagatggat tgcacgcagg    6360
ttctccggcc gcttgggtgg agaggctatt cggctatgac tgggcacaac agacaatcgg    6420
ctgctctgat gccgccgtgt tccggctgtc agcgcagggg cgcccggttc tttttgtcaa    6480
gaccgacctg tccggtgccc tgaatgaact gcaggacgag gcagcgcggc tatcgtggct    6540
ggccacgacg ggcgttcctt gcgcagctgt gctcgacgtt gtcactgaag cgggaaggga    6600
ctggctgcta ttgggcgaag tgccggggca ggatctcctg tcatctcacc ttgctcctgc    6660
cgagaaagta tccatcatgg ctgatgcaat gcggcggctg catacgcttg atccggctac    6720
ctgcccattc gaccaccaag cgaaacatcg catcgagcga gcacgtactc ggatggaagc    6780
cggtcttgtc gatcaggatg atctggacga agagcatcag gggctcgcgc cagccgaact    6840
gttcgccagg ctcaaggcgc gcatgcccga cggcgatgat ctcgtcgtga cccatggcga    6900
tgcctgcttg ccgaatatca tggtggaaaa tggccgcttt tctggattca tcgactgtgg    6960
ccggctgggt gtggcggacc gctatcagga catagcgttg gctacccgtg atattgctga    7020
agagcttggc ggcgaatggg ctgaccgctt cctcgtgctt tacggtatcg ccgctcccga    7080
ttcgcagcgc atcgccttct atcgccttct tgacgagttc ttctgagggg atcaattctc    7140
tagagctcgc tgatcagcct cgactgtgcc ttctagttgc cagccatctg ttgtttgccc    7200
ctcccccgtg ccttccttga ccctggaagg tgccactccc actgtccttt cctaataaaa    7260
tgaggaaatt gcatcgcatt gtctgagtag gtgtcattct attctggggg gtggggtggg    7320
gcaggacagc aagggggagg attgggaaga caatagcagg catgctgggg atgcggtggg    7380
ctctatggct tctgaggcgg aaagaaccag ctggggctcg actagagctt gcggaaccct    7440
tcgaagttcc tattctctag aaagtatagg aacttcatca gtcaggtaca taatataact    7500
tcgtataatg tatgctatac gaagttatta ggtggatcca ctaggcgcgc ctgaggactt    7560
gaagattggc taaataaacc taaaatggct atttatattg ggattaatac actttaagtg    7620
aaaaaaaaaa aaaaaagcaa ctggactcct agaaaagaaa tagtctgctg tagaaatgtg    7680
aggttttata ttagtgttga ataaatctta gtgtgactta ctgtttctta attacttctg    7740
agttacagac gtatattttt gagacttcat ctaaagaatt gctctctgca atatcttggt    7800
ttcctgacct ttgatggtg agatattttt cagtgagaga acacatttga tagagataga    7860
ttttcaaact agtttagatg tgaaggtgtt tgtggcccaa ctcttttggg aaacacaaga    7920
```

-continued

```
tttcatggta tagttttgtg tgcagtttgt gaaaactcag tgtttgtaaa tacactgttc   7980
agtcattctc attctcgtat gtgttagtag ctattttgaa agggctggta tttgagaaat   8040
cgcctacttg gcttccaaaa caaaaataaa aatattatgg cataacaggc cctgtgtggg   8100
cactaaacat atgtactttg aaatcatgta tttttctttg taacatcaga atgtctaaca   8160
tcagctttct aatactggaa gtgctgttga gagcagctgg ttgcacgttg tggagaagtc   8220
atgtttcctt tgagatcaga tgctattgct aatgtctgga gactggctgc agttatcaaa   8280
aaggcaataa tagtgacagc ctaggacagt taaatttcat ttgcttattt actgcacaac   8340
tttgcaagtt tctctaccga atacctcaca tggacaatgc ctgaaaaaca tgcaagttgt   8400
tttaaaaagt gccgtggcac atagttcaga acagggaggc atgccatggg gcccagatta   8460
taaagtgggc actgtttgac tcgtgcctac agcctggttg ctaccaagta gttggcactt   8520
aaacactttt tccataatgg tagacacagc tccggaacgt ggcagttgaa catgacctct   8580
ctaatggtag atacaactca agaacataat taaaagcagg acttagcaag cattaactca   8640
gcactttcca cctacttcat gattatgaga accgtctgaa atgattatga aaaattacac   8700
atctttatac tgggtatttt atttagttga gccaagcact ggtagcaaag aaaaaaggga   8760
acacttttat tcatatttca aagcaaaaca ttagtgattt tggaaacaag taacattagt   8820
tttgatatta ttttaattaa tttcaaaata acaatcacat tataaataat ttgttttttt   8880
tttttggctt tcttgttttg tttttgaga caggttctca ctatatagcc ctggttgtcc   8940
tggaactcac tatgtagacc agtctgactt caaactcaca agctctctgc ctcctgagta   9000
ctgggatcac aggtgttatg cccagtcaaa tttacaaata atcttattga acgcattgag   9060
gaatgtagat aatgtgtctt acaattgttt gtctacacat gaagatgttt agtgaagcaa   9120
tgcagttact actcattgat tttcaggttg gaccgatgct tgcagtgatt cttgctctga   9180
ctcctttgga catggttggc ctggggaagg gtagagtccc tagaagtgac aagtgaaact   9240
aactgctttg catgggaata aaatcctttg aataaatctc attacttcta cgccctaacc   9300
agtaaaacta attggataca ggtgactaca cataattcct cttaattgta ttttttaaca   9360
aaaagccctc acaatgaaaa acaaaataaa caccaacaaa atcctgagct ttaaaaggcc   9420
aaattacaga ttgtgggctg aggctggtct ctcttttttt tttttttttc ttaaatttga   9480
ttttattttt ttcacattcc atattccatt ccccgccccc cccacatcca ccctccaact   9540
gatccacatc ccacacctcc taggatcgcc cgggttgatt cgaggctgct aacaaatcga   9600
gtcgagcatc gagcagtgtg gttttcaaga ggaagcaaaa agcctctcca cccaggcctg   9660
gaatgtttcc acccaatgtc gagcagtgtg gttttgcaag aggaagcaaa aagcctctcc   9720
acccaggcct ggaatgtttc cacccaatgt cgagcaaacc ccgcccagcg tcttgtcatt   9780
ggcgaattcg aacacgcaga tgcagtcggg gcggcgcggt cccaggtcca cttcgcatat   9840
taaggtgacg cgtgtggcct cgaacaccga gcgaccctgc agcgaccgc ttaacagcgt    9900 caacagcgtg ccgcagatct tggtggcgtg aaactcccgc acctcttcgg ccagcgcctt   9960
gtagaagcgc gtgccatgga tcctgatgat gttgttgatt cttctaaatc ttttgtgatg   10020
gaaaactttt cttcgtacca cgggactaaa cctggttatg tagattccat tcaaaaaggt   10080
atacaaaagc caaaatctgg tacacaagga aattatgacg atgattggaa agggtttat    10140 agtaccgaca ataaatacga cgctgcggga tactctgtag ataatgaaaa cccgctctct   10200
ggaaaagctg gaggcgtggt caaagtgacg tatccaggac tgacgaaggt tctcgcacta   10260
aaagtggata atgccgaaac tattaagaaa gagttaggtt taagtctcac tgaaccgttg   10320
```

```
atggagcaag tcggaacgga agagtttatc aaaaggttcg gtgatggtgc ttcgcgtgta   10380
gtgctcagcc ttcccttcgc tgaggggagt tctagcgttg aatatattaa taactgggaa   10440
caggcgaaag cgttaagcgt agaacttgag attaattttg aaacccgtgg aaaacgtggc   10500
caagatgcga tgtatgagta tatggctcaa gcctgtgcag gaaatcgtgt caggcgatct   10560
ctttgtgaag gaaccttact tctgtggtgt gacataattg gacaaactac ctacagagat   10620
ttaaagctct aaggtaaata taaaattttt aagtgtataa tgtgttaaac tactgattct   10680
aattgtttgt gtattttaga ttccaaccta tggaactgat gaatgggagc agtggtggaa   10740
tgcagatcct agagctcgct gatcagcctc gactgtgcct tctagttgcc agccatctgt   10800
tgtttgcccc tccccgtgc cttccttgac cctggaaggt gccactccca ctgtcctttc     10860
ctaataaaat gaggaaattg catcgcattg tctgagtagg tgtcattcta ttctggggggg  10920 tggggtgggg caggacagca aggggggagga ttgggaagac aatagcaggc atgctgggga  10980
tgcggtgggc tctatggctt ctgaggcgga aagaaccagc ccgggcggtg gagctccagc   11040
ttttgttccc tttagtgagg gttaatttcg agcttggcgt aatcatggtc atagctgttt   11100
cctgtgtgaa attgttatcc gctcacaatt ccacacaaca tacgagccgg aagcataaag   11160
tgtaaagcct ggggtgccta atgagtgagc taactcacat taattgcgtt gcgctcactg   11220
cccgctttcc agtcgggaaa cctgtcgtgc cagctgcatt aatgaatcgg ccaacgcgcg   11280
gggagaggcg gtttgcgtat tgggcgctct tccgcttcct cgctcactga ctcgctgcgc   11340
tcggtcgttc ggctgcggcg agcggtatca gctcactcaa aggcggtaat acggttatcc   11400
acagaatcag gggataacgc aggaaagaac atgtgagcaa aaggccagca aaaggccagg   11460
aaccgtaaaa aggccgcgtt gctggcgttt ttccataggc tccgcccccc tgacgagcat   11520
cacaaaaatc gacgctcaag tcagaggtgg cgaaacccga caggactata aagataccag   11580
gcgtttcccc ctggaagctc cctcgtgcgc tctcctgttc cgaccctgcc gcttaccgga   11640
tacctgtccg cctttctccc ttcgggaagc gtggcgcttt ctcatagctc acgctgtagg   11700
tatctcagtt cggtgtaggt cgttcgctcc aagctgggct gtgtgcacga acccccccgtt  11760 cagcccgacc gctgcgcctt atccggtaac tatcgtcttg agtccaaccc ggtaagacac   11820
gacttatcgc cactggcagc agccactggt aacaggatta gcagagcgag gtatgtaggc   11880
ggtgctacag agttcttgaa gtggtggcct aactacggct acactagaag aacagtattt   11940
ggtatctgcg ctctgctgaa gccagttacc ttcggaaaaa gagttggtag ctcttgatcc   12000
ggcaaacaaa ccaccgctgg tagcggtggt tttttttgttt gcaagcagca gattacgcgc   12060
agaaaaaaag gatctcaaga agatcctttg atcttttcta cggggtctga cgctcagtgg   12120
aacgaaaact cacgttaagg gattttggtc atgagattat caaaaaggat cttcacctag   12180
atccttttaa attaaaaatg aagttttaaa tcaatctaaa gtatatatga gtaaacttgg   12240
tctgacagtt accaatgctt aatcagtgag gcacctatct cagcgatctg tctatttcgt   12300
tcatccatag ttgcctgact ccccgtcgtg tagataacta cgatacggga gggcttacca   12360
tctggcccca gtgctgcaat gataccgcga gacccacgct caccggctcc agatttatca   12420
gcaataaacc agccagccgg aagggccgag cgcagaagtg gtcctgcaac tttatccgcc   12480
tccatccagt ctattaattg ttgccgggaa gctagagtaa gtagttcgcc agttaatagt   12540
ttgcgcaacg ttgttgccat tgctacaggc atcgtggtgt cacgctcgtc gtttggtatg   12600
gcttcattca gctccggttc ccaacgatca aggcgagtta catgatcccc catgttgtgc   12660
```

-continued

```
aaaaaagcgg ttagctcctt cggtcctccg atcgttgtca gaagtaagtt ggccgcagtg    12720
ttatcactca tggttatggc agcactgcat aattctctta ctgtcatgcc atccgtaaga    12780
tgcttttctg tgactggtga gtactcaacc aagtcattct gagaatagtg tatgcggcga    12840
ccgagttgct cttgcccggc gtcaatacgg gataataccg cgccacatag cagaacttta    12900
aaagtgctca tcattggaaa acgttcttcg gggcgaaaac tctcaaggat cttaccgctg    12960
ttgagatcca gttcgatgta acccactcgt gcacccaact gatcttcagc atcttttact    13020
ttcaccagcg tttctgggtg agcaaaaaca ggaaggcaaa atgccgcaaa aaagggaata    13080
agggcgacac ggaaatgttg aatactcata ctcttccttt ttcaatatta ttgaagcatt    13140
tatcagggtt attgtctcat gagcggatac atatttgaat gtatttagaa aaataaacaa    13200 atagggggttc cgcgcacatt tccccgaaaa gtgccac                            13237
```

<210> SEQ ID NO 2
<211> LENGTH: 27
<212> TYPE: DNA
<213> ORGANISM: Artificial Sequence
<220> FEATURE:
<223> OTHER INFORMATION: Artifically synthesized oligonucleotide primer

<400> SEQUENCE: 2

```
gtcacttgaa tataccacag ttcccag                                              27
```

<210> SEQ ID NO 3
<211> LENGTH: 23
<212> TYPE: DNA
<213> ORGANISM: Artificial Sequence
<220> FEATURE:
<223> OTHER INFORMATION: Artifically synthesized oligonucleotide primer

<400> SEQUENCE: 3

```
catattggca cactaccctg gat                                                  23
```

<210> SEQ ID NO 4
<211> LENGTH: 23
<212> TYPE: DNA
<213> ORGANISM: Artificial Sequence
<220> FEATURE:
<223> OTHER INFORMATION: Artifically synthesized oligonucleotide primer

<400> SEQUENCE: 4

```
gctgaccgct tcctcgtgct tta                                                  23
```

<210> SEQ ID NO 5
<211> LENGTH: 25
<212> TYPE: DNA
<213> ORGANISM: Artificial Sequence
<220> FEATURE:
<223> OTHER INFORMATION: Artifically synthesized oligonucleotide primer

<400> SEQUENCE: 5

```
gaccaccaaa cagcatacac cagct                                                25
```

<210> SEQ ID NO 6
<211> LENGTH: 20
<212> TYPE: DNA
<213> ORGANISM: Artificial Sequence
<220> FEATURE:
<223> OTHER INFORMATION: Artifically synthesized oligonucleotide primer

<400> SEQUENCE: 6

```
atctttccag tgtctcattc                                                      20
```

```
<210> SEQ ID NO 7
<211> LENGTH: 19
<212> TYPE: DNA
<213> ORGANISM: Artificial Sequence
<220> FEATURE:
<223> OTHER INFORMATION: Artifically synthesized oligonucleotide primer

<400> SEQUENCE: 7
tacttcttgt ttcggtctt                                              19

<210> SEQ ID NO 8
<211> LENGTH: 18
<212> TYPE: DNA
<213> ORGANISM: Artificial Sequence
<220> FEATURE:
<223> OTHER INFORMATION: Artifically synthesized oligonucleotide primer

<400> SEQUENCE: 8
ggatgttggc attgaagc                                               18

<210> SEQ ID NO 9
<211> LENGTH: 18
<212> TYPE: DNA
<213> ORGANISM: Artificial Sequence
<220> FEATURE:
<223> OTHER INFORMATION: Artifically synthesized oligonucleotide primer

<400> SEQUENCE: 9
gattttagga gacgagca                                               18

<210> SEQ ID NO 10
<211> LENGTH: 20
<212> TYPE: DNA
<213> ORGANISM: Artificial Sequence
<220> FEATURE:
<223> OTHER INFORMATION: Artifically synthesized oligonucleotide primer

<400> SEQUENCE: 10
gaattccaaa gccagcatgt                                             20

<210> SEQ ID NO 11
<211> LENGTH: 20
<212> TYPE: DNA
<213> ORGANISM: Artificial Sequence
<220> FEATURE:
<223> OTHER INFORMATION: Artifically synthesized oligonucleotide primer

<400> SEQUENCE: 11
ccactcacag accctttgca                                             20

<210> SEQ ID NO 12
<211> LENGTH: 21
<212> TYPE: DNA
<213> ORGANISM: Artificial Sequence
<220> FEATURE:
<223> OTHER INFORMATION: Artifically synthesized oligonucleotide primer

<400> SEQUENCE: 12
gacaggcagg ccttctctga a                                           21

<210> SEQ ID NO 13
<211> LENGTH: 21
<212> TYPE: DNA
<213> ORGANISM: Artificial Sequence
<220> FEATURE:
```

-continued

```
<223> OTHER INFORMATION: Artifically synthesized oligonucleotide primer

<400> SEQUENCE: 13
cttctccaca ccagctgtgg a                                                 21

<210> SEQ ID NO 14
<211> LENGTH: 732
<212> TYPE: DNA
<213> ORGANISM: Artificial Sequence
<220> FEATURE:
<223> OTHER INFORMATION: Artifically synthesized TPK sequence

<400> SEQUENCE: 14
atggagcatg cctttacccc gttggagccc ctgctttcca ctgggaattt gaagtactgc      60
cttgtaattc ttaatcagcc tttggacaac tattttcgtc atctttggaa caaagctctt     120
ttaagagcct gtgccgatgg aggtgccaac cgcttatatg atatcaccga aggagagaga     180
gaaagctttt tgcctgaatt catcaatgga gactttgatt ctattaggcc tgaagtcaga     240
gaatactatg ctactaaggg atgtgagctc atttcaactc ctgatcaaga ccacactgac     300
tttactaagt gccttaaaat gctccaaaag aagatagaag aaaaagactt aaaggttgat     360
gtgatcgtga cactgggagg ccttgctggg cgttttgacc agattatggc atctgtgaat     420
accttgttcc aagcgactca catcactcct tttccaatta taataatcca agaggaatcg     480
ctgatctacc tgctccaacc aggaaagcac aggttgcatg tagacactgg aatggagggt     540
gattggtgtg gccttattcc tgttggacag ccttgtatgc aggttacaac cacaggcctc     600
aagtggaacc tcacaaatga tgtgcttgct tttggaacat tggtcagtac ttccaatacc     660
tacgacgggt ctggtgttgt gactgtggaa actgaccacc cactcctctg gaccatggcc     720
atcaaaagct aa                                                          732

<210> SEQ ID NO 15
<211> LENGTH: 32
<212> TYPE: DNA
<213> ORGANISM: Artificial Sequence
<220> FEATURE:
<223> OTHER INFORMATION: Artifically synthesized oligonucleotide primer

<400> SEQUENCE: 15
atggatccac catggagcat gcctttaccc cg                                     32

<210> SEQ ID NO 16
<211> LENGTH: 30
<212> TYPE: DNA
<213> ORGANISM: Artificial Sequence
<220> FEATURE:
<223> OTHER INFORMATION: Artifically synthesized oligonucleotide primer

<400> SEQUENCE: 16
atatcgatgg cttttgatgg ccatggtcca                                        30

<210> SEQ ID NO 17
<211> LENGTH: 243
<212> TYPE: PRT
<213> ORGANISM: Mus musculus

<400> SEQUENCE: 17

Met Glu His Ala Phe Thr Pro Leu Glu Pro Leu Leu Pro Thr Gly Asn
1               5                   10                  15

Leu Lys Tyr Cys Leu Val Val Leu Asn Gln Pro Leu Asp Ala Arg Phe
            20                  25                  30
```

-continued

```
Arg His Leu Trp Lys Lys Ala Leu Leu Arg Ala Cys Ala Asp Gly Gly
        35              40              45

Ala Asn His Leu Tyr Asp Leu Thr Glu Gly Glu Arg Glu Ser Phe Leu
    50              55              60

Pro Glu Phe Val Ser Gly Asp Phe Asp Ser Ile Arg Pro Glu Val Lys
65              70              75              80

Glu Tyr Tyr Thr Lys Lys Gly Cys Asp Leu Ile Ser Thr Pro Asp Gln
                85              90              95

Asp His Thr Asp Phe Thr Lys Cys Leu Gln Val Leu Gln Arg Lys Ile
            100             105             110

Glu Glu Lys Glu Leu Gln Val Asp Val Ile Val Thr Leu Gly Gly Leu
        115             120             125

Gly Gly Arg Phe Asp Gln Ile Met Ala Ser Val Asn Thr Leu Phe Gln
    130             135             140

Ala Thr His Ile Thr Pro Val Pro Ile Ile Ile Gln Lys Asp Ser
145             150             155             160

Leu Ile Tyr Leu Leu Gln Pro Gly Lys His Arg Leu His Val Asp Thr
                165             170             175

Gly Met Glu Gly Ser Trp Cys Gly Leu Ile Pro Val Gly Gln Pro Cys
            180             185             190

Asn Gln Val Thr Thr Thr Gly Leu Lys Trp Asn Leu Thr Asn Asp Val
            195             200             205

Leu Gly Phe Gly Thr Leu Val Ser Thr Ser Asn Thr Tyr Asp Gly Ser
    210             215             220

Gly Leu Val Thr Val Glu Thr Asp His Pro Leu Leu Trp Thr Met Ala
225             230             235             240

Ile Lys Ser
```

<210> SEQ ID NO 18
<211> LENGTH: 732
<212> TYPE: DNA
<213> ORGANISM: Mus musculus

<400> SEQUENCE: 18

```
atggagcatg cctttacccc gttggaaccc ctgctaccta cggggaactt gaaatactgc      60
cttgtggttc ttaatcagcc tttggatgca cgatttcgcc atctttggaa aaaagctctc     120
ttaagagcct gtgctgatgg gggtgccaac cacttatatg atctcactga aggagagaga     180
gaaagcttct tgcctgaatt cgtcagtggg gactttgatt ctattaggcc tgaagtcaaa     240
gagtactaca ccaagaaggg ctgtgatctt atttcaactc ctgaccaaga ccacactgac     300
tttaccaagt gtcttcaagt gctccaaagg aagatagagg aaaaggaact gcaggttgac     360
gtgattgtga cactgggagg tctcggtggg cgttttgacc aaatcatggc ctctgtgaat     420
acccttttcc aagccactca catcactcct gtgccgatta taataatcca aaaggactct     480
ctcatctacc tcctccaacc cgggaagcac aggctccatg tagacactgg aatggaaggg     540
agctggtgtg gcctgattcc tgttggacag ccttgcaacc aggtgacgac aacaggcctg     600
aaatggaacc tcacaaatga tgttcttggc tttggaacac tggtcagtac ttctaacacc     660
tacgatgggt ccggccttgt cactgtggaa actgaccacc cactcctctg gaccatggcc     720
atcaagagct aa                                                        732
```

<210> SEQ ID NO 19
<211> LENGTH: 448

<212> TYPE: DNA
<213> ORGANISM: Artificial Sequence
<220> FEATURE:
<223> OTHER INFORMATION: Artifically synthesized neuron-specific
      promoter sequence

<400> SEQUENCE: 19
agtgcaagtg ggttttagga ccaggatgag gcggggtggg ggtgcctacc tgacgaccga        60
ccccgaccca ctggacaagc acccaacccc cattccccaa attgcgcatc ccctatcaga       120 gaggggagg ggaaacagga tgcggcgagg cgcgtgcgca ctgccagctt cagcaccgcg       180
gacagtgcct tcgccccgc ctggcggcgc gcgccaccgc cgcctcagca ctgaaggcgc       240
gctgacgtca ctcgccggtc ccccgcaaac tcccctttccc ggccaccttg gtcgcgtccg       300
cgccgccgcc ggcccagccg gaccgcacca cgcgaggcgc gagatagggg ggcacgggcg       360
cgaccatctg cgctgcggcg ccggcgactc agcgctgcct cagtctgcgg tgggcagcgg       420
aggagtcgtg tcgtgcctga gagcgcag                                          448

<210> SEQ ID NO 20
<211> LENGTH: 589
<212> TYPE: DNA
<213> ORGANISM: Artificial Sequence
<220> FEATURE:
<223> OTHER INFORMATION: Artifically synthesized WPRE sequence

<400> SEQUENCE: 20
aatcaacctc tggattacaa aatttgtgaa agattgactg gtattcttaa ctatgttgct        60
ccttttacgc tatgtggata cgctgcttta atgcctttgt atcatgctat tgcttcccgt       120
atggctttca ttttctcctc cttgtataaa tcctggttgc tgtctcttta tgaggagttg       180
tggcccgttg tcaggcaacg tggcgtggtg tgcactgtgt ttgctgacgc aaccccccact       240 ggttggggca ttgccaccac ctgtcagctc ctttccggga ctttcgcttt cccctccct       300 attgccacgg cggaactcat cgccgcctgc cttgcccgct gctggacagg ggctcggctg       360
ttgggcactg acaattccgt ggtgttgtcg gggaaatcat cgtcctttcc ttggctgctc       420
gcctatgttg ccacctggat tctgcgcggg acgtccttct gctacgtccc ttcggccctc       480
aatccagcgg accttccttc ccgcggcctg ctgccggctc tgcggcctct tccgcgtctt       540
cgccttcgcc ctcagacgag tcggatctcc ctttgggccg cctccccgc                   589

<210> SEQ ID NO 21
<211> LENGTH: 225
<212> TYPE: DNA
<213> ORGANISM: Artificial Sequence
<220> FEATURE:
<223> OTHER INFORMATION: Artifically synthesized hGH polyA sequence

<400> SEQUENCE: 21
ctgtgccttc tagttgccag ccatctgttg tttgcccctc ccccgtgcct tccttgaccc        60
tggaaggtgc cactcccact gtcctttcct aataaaatga ggaaattgca tcgcattgtc       120
tgagtaggtg tcattctatt ctggggggtg gggtggggca ggacagcaag ggggaggatt       180
gggaagacaa tagcaggcat gctggggatg cggtgggctc tatgg                       225

<210> SEQ ID NO 22
<211> LENGTH: 130
<212> TYPE: DNA
<213> ORGANISM: Artificial Sequence
<220> FEATURE:
<223> OTHER INFORMATION: Artifically synthesized ITR sequence -continued

```
<400> SEQUENCE: 22
aggaacccct agtgatggag ttggccactc cctctctgcg cgctcgctcg ctcactgagg      60
ccgggcgacc aaaggtcgcc cgacgcccgg gctttgcccg ggcggcctca gtgagcgagc     120
gagcgcgcag                                                            130

<210> SEQ ID NO 23
<211> LENGTH: 204
<212> TYPE: DNA
<213> ORGANISM: Artificial Sequence
<220> FEATURE:
<223> OTHER INFORMATION: Artifically synthesized CMV promoter sequence

<400> SEQUENCE: 23
gtgatgcggt tttggcagta catcaatggg cgtggatagc ggtttgactc acggggattt      60
ccaagtctcc accccattga cgtcaatggg agtttgtttt ggcaccaaaa tcaacgggac     120
tttccaaaat gtcgtaacaa ctccgcccca ttgacgcaaa tgggcggtag gcgtgtacgg     180
tgggaggtct atataagcag agct                                            204
```